United States Patent
D'Alessandro et al.

(10) Patent No.: US 11,090,331 B2
(45) Date of Patent: *Aug. 17, 2021

(54) METHODS AND TREATMENT FOR REDUCING THE RISK OF AN INFLAMMATORY RESPONSE

(71) Applicant: Hemanext Inc., Lexington, MA (US)

(72) Inventors: Angelo D'Alessandro, Denver, CO (US); Rafael Cordero, Bedford, MA (US); Andrew Dunham, Tower Lakes, IL (US); Philip Keegan, Waunakee, WI (US); Tatsuro Yoshida, West Newton, MA (US)

(73) Assignee: Hemanext Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/875,482

(22) Filed: May 15, 2020

(65) Prior Publication Data

US 2020/0276234 A1 Sep. 3, 2020

Related U.S. Application Data

(63) Continuation of application No. 16/312,119, filed as application No. PCT/US2017/038859 on Jun. 22, 2017.

(60) Provisional application No. 62/354,041, filed on Jun. 23, 2016.

(51) Int. Cl.
| | |
|---|---|
| *A61K 35/14* | (2015.01) |
| *A61M 1/38* | (2006.01) |
| *A61M 1/02* | (2006.01) |

(52) U.S. Cl.
CPC .............. *A61K 35/14* (2013.01); *A61M 1/38* (2013.01); *A61M 1/0272* (2013.01)

(58) Field of Classification Search
None
See application file for complete search history.

(56) References Cited

U.S. PATENT DOCUMENTS

| | | | |
|---|---|---|---|
| 5,120,659 A | 6/1992 | King et al. | |
| 5,789,152 A | 8/1998 | Black et al. | |
| 6,162,396 A | 12/2000 | Bitensky et al. | |
| 8,071,282 B2 | 12/2011 | Bitensky et al. | |
| 2015/0284682 A1* | 10/2015 | Yoshida | A61M 1/342 435/2 |
| 2019/0388467 A1* | 12/2019 | D'Alessandro | A61P 7/00 |
| 2020/0276234 A1* | 9/2020 | D'Alessandro | A61K 35/14 |

FOREIGN PATENT DOCUMENTS

| | | |
|---|---|---|
| WO | WO 2010/147621 A1 | 12/2010 |
| WO | WO 2013/006631 A1 | 1/2013 |
| WO | WO 2016/187353 A1 | 11/2016 |

OTHER PUBLICATIONS

Cognasse et al., "The role of microparticles in inflammation and transfusion: A concise review," *Transfusion and Apheresis Science*, 53(2):159-167 (2015), Previously Submitted in U.S. Appl. No. 16/312,119.

García-Roa et al., "Red Blood cell storage time and transfusion: current practice, concerns and future perspectives," *Blood Transfusion*, 15:222-231 (2017), Previously Submitted in U.S. Appl. No. 16/312,119.

Gevi et al., "Alterations of red blood cell metabolome during cold liquid storage of erythrocyte concentrates in CPD-SAGM," *Journal of Proteomics*, 76:168-180 (2012), Previously Submitted in U.S. Appl. No. 16/312,119.

Henschler et al., "Development of the S-303 Pathogen Inactivation Technology for Red Blood Cell Concentrates," *Transfusion Medicine and Hemotherapy*, 38:33-42 (2011), Previously Submitted in U.S. Appl. No. 16/312,119.

Irsch et al., "Pathogen Inactivation of Platelet and Plasma Blood Components for Transfusion Using the INTERCEPT Blood System™," *Transfusion Medicine and Hemotherapy*, 38:19-31 (2011), Previously Submitted in U.S. Appl. No. 16/312,119.

Kaiser-Guignard et al., "The clinical and biological impact of new pathogen inactivation technologies on platelet concentrates," *Blood Reviews*, 28:235-241 (2014), Previously Submitted in U.S. Appl. No. 16/312,119.

Pidcoke et al., "Primary hemostatic capacity of whole blood: a comprehensive analysis of pathogen reduction and refrigeration effects over time," *Transfusion*, 53:137-149 (2013), Previously Submitted in U.S. Appl. No. 16/312,119.

Picker, S.M., "Current methods for the reduction of blood-borne pathogens: a comprehensive literature review," *Blood Transfusion*, 11:343-348 (2013), Previously Submitted in U.S. Appl. No. 16/312,119.

Poncelet et al., "Tips and tricks for flow cytometry-based analysis and counting of microparticles," *Transfusion and Apheresis Science*, 53(2):110-126 (2015), Previously Submitted in U.S. Appl. No. 16/312,119.

Schubert et al., "Whole blood treated with riboflavin and ultraviolet light: quality assessment of all blood components produced by the buffy coat method," *Transfusion*, 55(4):815-823 (2015), Previously Submitted in U.S. Appl. No. 16/312,119.

Wagner, S.J., "Developing pathogen reduction technologies for RBC suspensions," *Vox Sanguinis*, 100:112-121 (2011), Previously Submitted in U.S. Appl. No. 16/312,119.

Yoshida et al., "Anaerobic storage of red blood cells," *Blood Transfusion*, 8:220-236 (2010), Previously Submitted in U.S. Appl. No. 16/312,119.

Yoshida et al., "The effects of additive solution pH and metabolic rejuvenation on anaerobic storage of red cells," *Transfusion*, 48:2096-2105 (2008), Previously Submitted in U.S. Appl. No. 16/312,119.

Zolla et al., "Classic and alternative red blood cell storage strategies: seven years of '-omics' investigations," *Blood Transfusion*, 13(1):21-31 (2015), Previously Submitted in U.S. Appl. No. 16/312,119.

* cited by examiner

*Primary Examiner* — Ralph J Gitomer
(74) *Attorney, Agent, or Firm* — Arnold & Porter Kaye Scholer LLP

(57) ABSTRACT

Method for transfusion medicine to reduce adverse events in transfusion patient populations based on underlying patient physiology. Methods for reducing the risk of an inflammatory response in a sickle cell patient in need of a blood transfusion.

19 Claims, 20 Drawing Sheets

METHODS AND TREATMENT FOR REDUCING THE RISK OF AN INFLAMMATORY RESPONSE

CROSS-REFERENCE TO RELATED APPLICATIONS

This application is a continuation of U.S. application Ser. No. 16/312,119, filed Dec. 20, 2018, which is a U.S. National Stage of International Application No. PCT/US2017/038859, filed Jun. 22, 2017, which claims benefit of U.S. Provisional Application No. 62/354,041, filed Jun. 23, 2016, each of which are incorporated by reference in their entireties.

FIELD OF THE INVENTION

The present disclosure relates to improvements in the field of transfusion medicine.

BACKGROUND OF THE INVENTION

When stored conventionally, blood undergoes a steady deterioration which is associated with various storage lesions including, among others, hemolysis, hemoglobin degradation, vesiculation, increased oxidative stress, reduced ATP, and 2,3-DPG concentrations. When transfused into a patient, the effects of the steady deterioration during storage manifest, for example, as a reduction in the 24-hour in vivo recovery, increases in extravascular hemolysis and non-transferrin bound iron. The rapid decrease in the hematocrit that results from reduced 24-hour recovery, when severe, can result in delayed hemolytic transfusion reaction (DHTR). Other complications, for example systemic inflammatory response syndrome (SIRS), transfusion related acute lung injury (TRALI), and transfusion related immunomodulation (TRIM) are associated with transfusion of stored blood, though identification of the underlying causes has remained unclear. In certain cases, patients to receive blood transfusions suffer from a variety of underlying conditions, such as diabetes, that are associated with increased oxidative stress and oxidative injury. Patients having sickle cell disease or thalassemia who receive regular transfusions to manage the condition or treat acute complications can develop adverse reactions to transfused blood. Because of these and other medical sequelae of transfusion of stored blood, a variety of approaches have been developed to minimize the effects of storage on blood and to improve medical outcomes. See, for example, Zimring et al., "Established and theoretical factors to consider in assessing the red cell storage lesion" in *Blood,* 125:2185-90 (2015); D'Alessandro et al., "Time-course investigation of SAGM-stored leukocyte-filtered red blood cell concentrates: from metabolism to proteomics" Haematologica 97(1):107-115 (2012); D'Alessandro et al., "Red blood cell metabolism under prolonged anaerobic storage" *Molecular BioSystems* 9(6):1196-209 (2013); D'Alessandro et al., "Red blood cell storage in additive solution-7 preserves energy and redox metabolism: a metabolomics approach," *Transfusion,* 55(12):2955-66 (2015); D'Alessandro et al., "Routine storage of red blood cell (RBC) units in additive solution-3: a comprehensive investigation of the RBC metabolome," *Transfusion,* 55(6):1155-68 (2015); D'Alessandro et al., "Citrate metabolism in red blood cells stored in additive solution-3," *Transfusion,* 57(2): 325-336 (2016) (hereby incorporated by reference in its entirety).

A number of approaches have been developed aimed at minimizing storage lesions and improving transfusion outcomes. Approaches include additive solutions (For example, U.S. Pat. No. 4,769,318 to Hamasaki et al. and U.S. Pat. No. 4,880,786 to Sasakawa et al. U.S. Pat. No. 6,447,987 to Hess et al.), frozen storage (see U.S. Pat. No. 6,413,713 to Serebrennikov Chaplin et al., "Blood Cells for Transfusion," *Blood,* 59: 1118-20 (1982), and Valeri et al., "The survival, function, and hemolysis of human RBCs stored at 4 degrees C. in additive solution (AS-1, AS-3, or AS-5) for 42 days and then biochemically modified, frozen, thawed, washed, and stored at 4 degrees C. in sodium chloride and glucose solution for 24 hours," *Transfusion,* 40:1341-5 (2000) ("Valeri 2000"); D'Alessandro, et al., "An update on red blood cell storage lesions, as gleaned through biochemistry and omics technologies," *Transfusion,* 55(1): 205-219 (epub 2014); D'Alessandro, et al., "Red blood cell metabolic responses to refrigerated storage, rejuvenation, and frozen storage," *Transfusion,* 57(4):1019-1030 (2017); and D'Alessandro, et al., "Red blood cell storage lesion," *International Society of Blood Transfusion, ISBT Science Series,* 12:207-213 (2017), hereby incorporated by reference in their entireties), and rejuvenation (see Valeri 2000).

One approach that has proven successful in improving blood quality and extending its utility is through the depletion of oxygen and storage under anaerobic conditions. Among the benefits of storing blood under oxygen depleted conditions are improved levels of ATP and 2,3-DPG, and reduced hemolysis. U.S. Pat. No. 5,624,794 to Bitensky et al., U.S. Pat. No. 6,162,396 to Bitensky et al., and U.S. Pat. No. 5,476,764 to Bitensky (hereby incorporated by reference in their entireties) are directed to the storage of red blood cells under oxygen-depleted conditions. U.S. Pat. No. 5,789,151 to Bitensky et al. is directed to blood storage additive solutions. U.S. Pat. No. 6,162,396 to Bitensky et al. (the '396 patent) (hereby incorporated by reference in their entireties) discloses anaerobic storage bags for blood storage that comprise an oxygen impermeable outer layer, a red blood cell (RBC) compatible inner layer that is permeable to oxygen, and having an oxygen scrubber placed between the inner and outer layers.

Storing blood under oxygen depleted conditions can also result in reduced microparticle levels (see Yoshida et al., "The effects of additive solution pH and metabolic rejuvenation on anaerobic storage of red cells," Transfusion 48:2096-2105 (2008) and Yoshida, T., et al. Reduction of microparticle generation during anaerobic storage of red blood cells. Transfusion, 52, 83A (2012), hereby incorporated by reference in their entireties)), reductions in the loss of deformability, reduced lipid and protein oxidation and higher post transfusion survival when compared to blood stored under conventional conditions (see D'Alessandro et al. "Red blood cell metabolism under prolonged anaerobic storage," *Mol Biosystems* 6:1196-1209 (2013); Pallotta et al., "Storing red blood cells with vitamin C and N-acetylcysteine prevents oxidative stress-related lesions: a metabolomics overview," *Blood Transfusion,* 12: 376-387 (2014); Zolla and D'Alessandro, "Response to 'platelets proteomics in transfusion medicine: a reality with challenging but promising future'," *Blood Transfusion,* 11: 316 (2013); Blasi et al., "Red blood cell storage and cell morphology," Transfusion Medicine, 22: 90-96 (2012); Longo et al., "Deoxygenation of leucofiltered erythrocyte concentrates preserves proteome stability during storage in the blood bank," *Blood Transfus* 12(4): 599-604 (2014) ("Longo 2014"); and Reisz, et al., "Oxidative modifications of glyceraldehyde 3-phosphate dehydrogenase regulate metabolic reprogramming of stored red blood cells," *Blood*, (2016) ("Reisz 2016") (hereby incorporated by reference in their entireties)).

Oxidative damage during storage has been implicated as a major contributor to packed red blood cell (pRBC) membrane damage, as suggested by the accumulation of markers of lipid peroxidation, such as isoprostane, and oxidized structural and functional proteins, such as band 3, glyceraldehyde 3-phosphate dehydrogenase and hemoglobins (see Wither et al., "Hemoglobin oxidation at functional amino acid residues during routine storage of red blood cells," *Transfusion*, (56)2: 421-426, (2016) ("Wither 2016"); and Reisz 2016). Increasing amounts of cytokines during storage duration can also play a role in storage lesion development with potential clinical implications for a negative transfusion outcome.

Certain patient populations are more susceptible to storage lesions than others. Without limiting patient populations, these patient population include massively or chronically-transfused recipients, such as trauma or cancer patients, or patients suffering from hemoglobinopathies (e.g., sickle cell disease). Among these more sensitive populations are, as non-limiting examples, trauma patients and cancer patients. Associated with the adverse clinical outcomes is the accumulation of biologic response modifiers (BRMs) that include cytokines that mediate inflammation, regulate cell growth, regulate angiogenesis and modulate t-helper cell function. Among these BRMs are interleukin 17 (IL-17), eotaxin (CCL11), basic FGF (bFGF), macrophage inflammatory protein 1a (MIP-1a), monocyte chemotactic protein 1 (MCP-1), platelet-derived growth factor (PDGF), tumor necrosis factor alpha (TNF-$\alpha$), vascular endothelial growth factor (VEGF), hydroxyeicosatetraenoic acid (HETEs), leukotrienes, and thromboxanes. See Behrens et al., "Accumulation of biologic response modifiers during red blood cell cold storage," *Transfusion* 49(Suppl3):10A (2009) (hereby incorporated by reference in its entirety). It has also been observed that cytokines accumulate during blood storage and these accumulated cytokines can be associated with negative outcomes when given perioperatively to cancer patients. See Benson et al., "Accumulation of Pro-Cancer Cytokines in the Plasma Fraction of Stored Packed Red Cells,"*J Gastrointest Surg.* 16:460-468 (2012) (hereby incorporated by reference in its entirety).

While methods to reduce storage lesions have been advancing, an understanding of what changes are occurring during storage has been lacking. Recent molecular, genomic and metabolic studies have begun to identify specific changes that occur in red blood cells during the storage process. See D'Alessandro et al., "Red blood cell metabolism under prolonged anaerobic storage," Mol. Biosyst. 9(6):1196-209 (2013) (D'Alessandro 2013); D'Alessandro et al., "Time-course investigation of SAGM-stored leukocyte-filtered red blood cell concentrates: from metabolism to proteomics" Haematologica 97(1):107-115 (2012); and Roback et al., "Metabolomics of AS-I RBC storage," Transfus Med Rev. 28(2): 41-55 (2014) (hereby incorporated by reference in their entireties). While D'Alessandro 2013 intended to compare metabolism of red blood cells stored under aerobic and oxygen reduced conditions, only steady state metabolic parameters were measured with preliminary metabolomics methods far from current state of the art analytical workflows. Results therein collected were therefore preliminary in nature and limited the interpretation of the metabolic benefits associated with anaerobic storage of packed RBCs, owing to the lack of mechanistic evidence related to the actual metabolic fluxes through glycolysis and the pentose phosphate pathway of hypoxically stored erythrocytes. Accordingly the results did not correctly reveal the improved characteristics of oxygen reduced stored blood. Due to these deficiencies, D'Alessandro 2013 concluded that oxygen reduced storage elevated oxidative stress may impair the RBC antioxidant capacity by limiting glucose metabolism through the Pentose Phosphate Pathway, which in turn generates reducing equivalents (NADPH) necessary to modulate the redox poise (e.g. recycling of oxidized glutathione). However, these steady state observations did not provide any actual direct measurements of metabolic fluxes. which were not directly tested in that study. In contrast to the results of D'Alessandro 2013, results of the present disclosure correctly reveal, among other beneficial properties, decreased oxidative stress and activation of the PPP.

Storage tests to ascertain the effects of anaerobic storage on overall blood health in various storage solutions as identified improvements including reduced hemolysis (mandated by the FDA to remain below 1% for the duration of storage), as well as ATP and 2,3-DPG levels. Although not currently required by any global regulatory board, physiological maintenance of ATP and 2,3-DPG levels throughout storage has the potential of improving the overall general viability and therapeutic effectiveness of transfused blood products.

For the present studies, $^{13}$C-glucose (position 1,2 and 3) is spiked at the beginning of the storage, providing a method to trace and compare the actual fluxes of glucose oxidation through glycolysis (which generates high energy phosphate compounds) and the pentose phosphate pathway (to fuel antioxidant cascades), as determined by calculating isotopologue ratios of lactate +2 and +3, as well as, the energy metabolism in both anaerobic and aerobically stored cells throughout the storage period. Briefly, while not being limited by theory, the non-oxidative portion of the pentose phosphate pathway (PPP) intersects with the Embden-Meyerhof-Parnas Pathway (EMP), 5-carbon sugars re-enters EMP, and end up as lactate. Lactate emerges through oxidative PPP (without back-reaction, gluconeogenesis) and will be lacking $^{13}$C at position 1 (which is released in the form of CO2 when glucose is metabolized through the PPP), while lactate produced directly from glucose via EMP will have either all three carbons with $^{13}$C or none at all. In this manner, flux through PPP can be estimated using a metabolic model. Since ribose-5-P enters Adenine nucleotide pool (AXP) pathway, we are able to deduce further insights into ATP degradation and re-synthesis. See Reisz 2016.

Since the identification of blood groups at the turn of the 20$^{th}$ century, and the development by Rous and Turner of methods to store blood for transfusion in 1916, blood transfusion has become a routine therapy. Transfusion therapy ranges from the treatment of trauma and replacement of blood during surgery, to cancer therapies, and to treatments of genetic diseases like sickle cell anemia and thalassemia. Notably, but for a determination of blood groups and immunologic incompatibilities, little progress has been made in understanding the changes underlying blood storage lesions or identifying patients at risk of complications from transfusion therapies. To date, recommendations for optimal methods and selections of patient populations has received little attention. Recently, practitioners have observed improved outcomes for trauma victims and hemorrhagic patients, when provided whole, unfractionated blood (except for leukocyte reduction to reduce non-hemolytic febrile transfusion reactions (NHFTRs), alloimmunization, and infection) over reconstituted blood when provided at a 1:1:1 ratio of plasma, platelets, and RBC.

While the underlying biochemistry and physiology for the improvements observed for whole blood are not clear, the observations have led to discussions among practitioners of differentiation of patient populations for transfusions.

As an understanding of the biochemical and cellular physiological impacts of reduced oxygen storage on red blood cells has emerged, it has become apparent that heterogeneity in patient pathologies indicates that transfusion therapies need to move beyond a one size fits all approach. Rather, the wide range of chronic and acute pathologies indicates that a finer degree of definition and control over the biochemical and cellular makeup of the blood product can improve patient outcomes. Although some patient populations, particularly the young, relatively healthy patients requiring acute transfusion of only 1-2 units generally tolerate the deleterious effects of red cell storage lesions, patient populations dependent on RBC transfusions for survival are more vulnerable to transfusion associated complications.

Accordingly, there is an increasing need to identify patient populations at risk for treatments using conventional transfusion methodologies and those that can benefit from customized transfusion medicine. In addition to differentiating patients based on blood type, the results presented below suggest an evaluation of the medical status of the patients to receive transfusions and matching patients to the age, storage conditions, additive solutions, and type of blood product (whole, pRBCs, reconstituted, double platelet, etc.) be considered by the physician before prescribing a particular form of transfusion therapy.

SUMMARY OF THE INVENTION

The present disclosure provides for, and includes, a method of reducing the risk of an inflammatory response in a patient and in need of a blood transfusion comprising providing oxygen reduced stored blood having reduced levels of at least one inflammatory factor when compared to non-oxygen reduced stored blood stored for an identical storage period wherein said patient has an increased risk of an inflammatory response.

The present disclosure provides for, and includes, a method for reducing oxidative stress in a human patient in need of a blood transfusion comprising providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has an increased risk of oxidative stress.

The present disclosure provides for, and includes, a method for reducing cardiac, renal and gastrointestinal ischemia reperfusion injury in a patient in need of a blood transfusion comprising providing oxygen reduced stored blood that has an initial oxygen saturation of 20% or less prior to being stored for a storage period for transfusion to a human patient in need of a blood transfusion and having an increased risk for cardiac, renal and gastrointestinal ischemia reperfusion injury.

The present disclosure provides for, and includes, a method for reducing the risk of an adverse event in a hemoglobinopathy patient in need of a blood transfusion comprising providing oxygen reduced stored blood for transfusion into a hemoglobinopathy patient in need of a blood transfusion, wherein the oxygen reduced stored blood has an initial oxygen saturation of 20% or less prior to being stored for a storage period wherein the patient has an increased risk of oxidative stress.

The present disclosure provides for, and includes, a method for reducing delayed hemolytic transfusion reactions in a patient in need of a blood transfusion comprising providing oxygen reduced stored blood that has an initial oxygen saturation of 20% or less prior to being stored for a storage period wherein the patient has an increased risk of a delayed hemolytic transfusion reaction.

BRIEF DESCRIPTION OF THE DRAWINGS

The present disclosure is disclosed with reference to the accompanying drawings, wherein:

FIGS. 1 to 20 present the results of studies of stored blood (in this aspect, packed red blood cells) having an initial oxygen saturation of 20% or less prior to being stored for a storage period (oxygen reduced stored blood) compared to conventionally stored blood (normoxic) and blood that has been fully oxygenated prior to storage (hyperoxygenated or hyperoxic) according to aspects of the present disclosure.

FIG. 1 is a graph presenting the percent $SO_2$ over 42 days of conventionally stored normoxic (solid line) and hyperoxic (----) blood and anaerobically stored blood with an initial percent $SO_2$ of 20, 10, 5, and <3%.

FIG. 2 is a graph presenting the results of an experiment according to the present disclosure, comparing the levels of Leukotriene B4 of conventionally stored normoxic (solid line) and hyperoxic (---) and oxygen reduced stored blood with an initial percent $SO_2$ of 20, 10, 5, and <3%.

FIG. 3 is a graph presenting the results of an experiment according to the present disclosure, comparing the levels of Thromboxane B2 of conventionally stored normoxic (solid line) and hyperoxic (---) and oxygen reduced stored blood with an initial with an initial percent $SO_2$ of 20, 10, 5, and <3%.

FIG. 4A presents the levels of HETE in supernatant over a period of 42 days. FIG. 4B presents the levels of HETE in oxygen reduced stored blood over a period of 42 days.

FIG. 5 is a graph presenting the results of an experiment according to the present disclosure, comparing the levels of NADPH of conventionally stored normoxic (solid line) and hyperoxic (---) and oxygen reduced stored blood with an initial an initial percent $SO_2$ of 20, 10, 5, and <3%.

FIG. 6 is a graph presenting the results of an experiment according to the present disclosure, comparing NADPH/$NADP^+$ of conventionally stored normoxic (solid line) and hyperoxic (---) and oxygen reduced stored blood with an initial an initial percent $SO_2$ of 20, 10, 5, and <3%.

FIG. 7 is a graph presenting the results of an experiment according to the present disclosure, comparing the total NADPH and $NADP^+$ reservoirs of conventionally stored normoxic (solid line) and hyperoxic (---) and oxygen reduced stored blood with an initial an initial percent $SO_2$ of 20, 10, 5, and <3%.

FIG. 8 is a graph presenting the results of an experiment according to the present disclosure, comparing the total NADP and $NAD^+$ reservoirs of conventionally stored normoxic (solid line) and hyperoxic (---) and oxygen reduced stored blood with an initial an initial percent $SO_2$ of 20, 10, 5, and <3%.

FIG. 9 is a graph presenting the results of an experiment according to the present disclosure, comparing the levels of methylenetetrahydrofolate of conventionally stored normoxic (solid line) and hyperoxic (---) and oxygen reduced stored blood with an initial an initial percent $SO_2$ of 20, 10, 5, and <3%.

FIG. 10 is a graph presenting the results of an experiment according to the present disclosure, comparing the levels of glutamate of conventionally stored normoxic (solid line) and hyperoxic (---) and oxygen reduced stored blood with an initial an initial percent $SO_2$ of 20, 10, 5, and <3%.

FIG. 11 is a graph presenting the results of an experiment according to the present disclosure, comparing the levels of reduced glutathione (GSH) of conventionally stored normoxic (solid line) and hyperoxic (---) and oxygen reduced stored blood with an initial an initial percent $SO_2$ of 20, 10, 5, and <3%.

FIG. 12 is a graph presenting the results of an experiment according to the present disclosure, comparing the GSH/GSSG ratio of conventionally stored normoxic (solid line) and hyperoxic (---) and oxygen reduced stored blood with an initial an initial percent $SO_2$ of 20, 10, 5, and <3%.

FIG. 13 is a graph presenting the results of an experiment according to the present disclosure, comparing the levels of cysteine of conventionally stored normoxic (solid line) and hyperoxic (---) and oxygen reduced stored blood with an initial an initial percent $SO_2$ of 20, 10, 5, and <3%.

FIG. 14 is a graph presenting the results of an experiment according to the present disclosure, comparing the levels of urate of conventionally stored normoxic (solid line) and hyperoxic (---) and oxygen reduced stored blood with an initial an initial percent $SO_2$ of 20, 10, 5, and <3%.

FIG. 15 is a graph presenting the results of an experiment according to the present disclosure, comparing the EMP flux of conventionally stored normoxic (solid line) and hyperoxic (---) and oxygen reduced stored blood with an initial an initial percent $SO_2$ of 20, 10, 5, and <3%.

FIG. 16 is a graph presenting the results of an experiment according to the present disclosure, comparing ATP synthesis in conventionally stored normoxic (solid line) and hyperoxic (---) and oxygen reduced stored blood with an initial an initial percent $SO_2$ of 20, 10, 5, and <3%.

FIG. 17 is a graph presenting the results of an experiment according to the present disclosure, comparing Cys152 dioxidation of glyceraldehyde 3-phosphate dehydrogenase in conventionally stored normoxic (solid line) and hyperoxic (---) and oxygen reduced stored blood with an initial percent $SO_2$ of 5%.

FIG. 19 is a graph presenting the results of an experiment according to the present disclosure, comparing histidine 93 of hemoglobin beta subunit oxidation in conventionally stored normoxic (solid line) and hyperoxic (---) and oxygen reduced stored blood with an initial an initial percent $SO_2$ of 20, 10, 5, and <3%.

FIG. 20 is a graph presenting the results of an experiment according to the present disclosure, comparing methemoglobin levels of conventionally stored normoxic (solid line) and hyperoxic (---) and oxygen reduced stored blood with an initial an initial percent $SO_2$ of 20, 10, 5, and <3%.

Corresponding reference characters indicate corresponding parts throughout the several views. The examples set out herein illustrate(s) several embodiment(s) of the present disclosure but should not be construed as limiting the scope of the present disclosure in any manner.

DETAILED DESCRIPTION

In contrast to the advances in personalized medical treatment in a wide variety of medical fields, other than blood group typing, the risks to certain populations when receiving stored blood from blood banks have not been identified and effective strategies and methods have not been developed to reduce or minimize the risks. More specifically, certain populations are at increased risk to complications from transfusion therapies based on underlying or accompanying secondary conditions (e.g., pre-existing conditions). Pre-existing conditions include, but are not limited to diabetes, ischemic heart disease, systemic inflammatory syndrome brought on by trauma or infection, multiple organ failure brought on by trauma or infection, smoke inhalation, and chronic pulmonary obstructive disease such as systemic inflammation due to infection, autoimmune diseases, and diabetes. Yet other populations, such as sickle cell and thalassemia patients, are at increased risk of complications resulting, for example, from multiple transfusions. Oxygen reduced stored blood and methods provided herein, can provide new and unexpected reductions in levels of inflammatory factors, improved protection from oxidative damage, reduced levels of microparticles, and/or other changes during storage thereby providing improvements and safety or other advantages to certain populations of patients in need of transfusion therapy. As provided herein, the present methods include those that provide for, and include, reductions in morbidity and adverse events in certain patients identifiable as having pre-existing conditions associated with increased risk.

While certain benefits of oxygen reduced stored blood have been known in art, relatively little is known regarding the nature of the storage lesion and the changes that occur during conventional storage or during oxygen reduced storage. As provided below in Table 1, changes to stored blood are recognizable as early as 2 days after the initiation of cold storage.

TABLE 1

Improvements and clinical benefits to oxygen reduced stored blood compared to conventional storage

Figure 1:
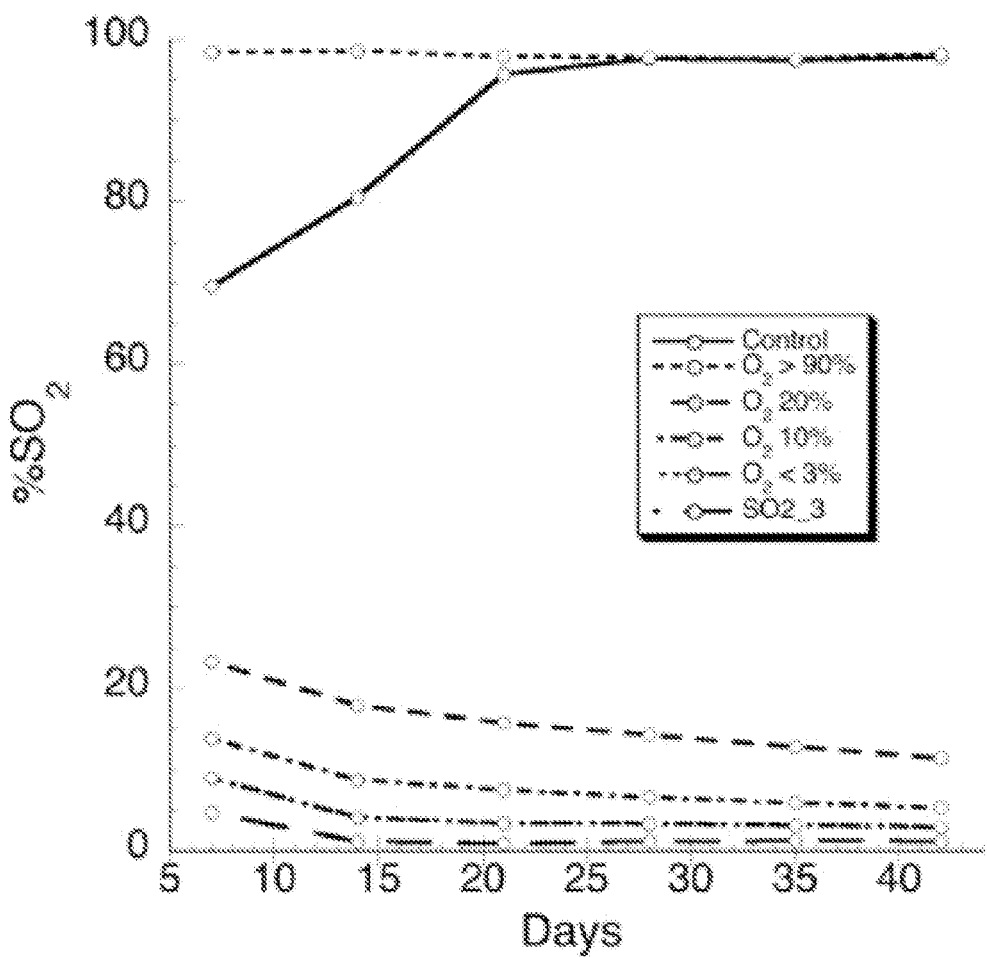

| Changed blood | | | Date of Improvement (day) | | | | | | | |
|---|---|---|---|---|---|---|---|---|---|---|
| Molecule/pathway | SO2 range | Clinical Benefit | 2 | 7 | 14 | 21 | 28 | 35 | 42 | Change† | FIG. |
| 1 SO₂ does not increase during storage | <3-20 | Maintain steady redox environment; prevent increase in oxidative stress | X | X | X | X | X | X | X | N/A | FIG. 1 |

TABLE 1-continued

Improvements and clinical benefits to oxygen reduced stored blood compared to conventional storage

Figure 2:
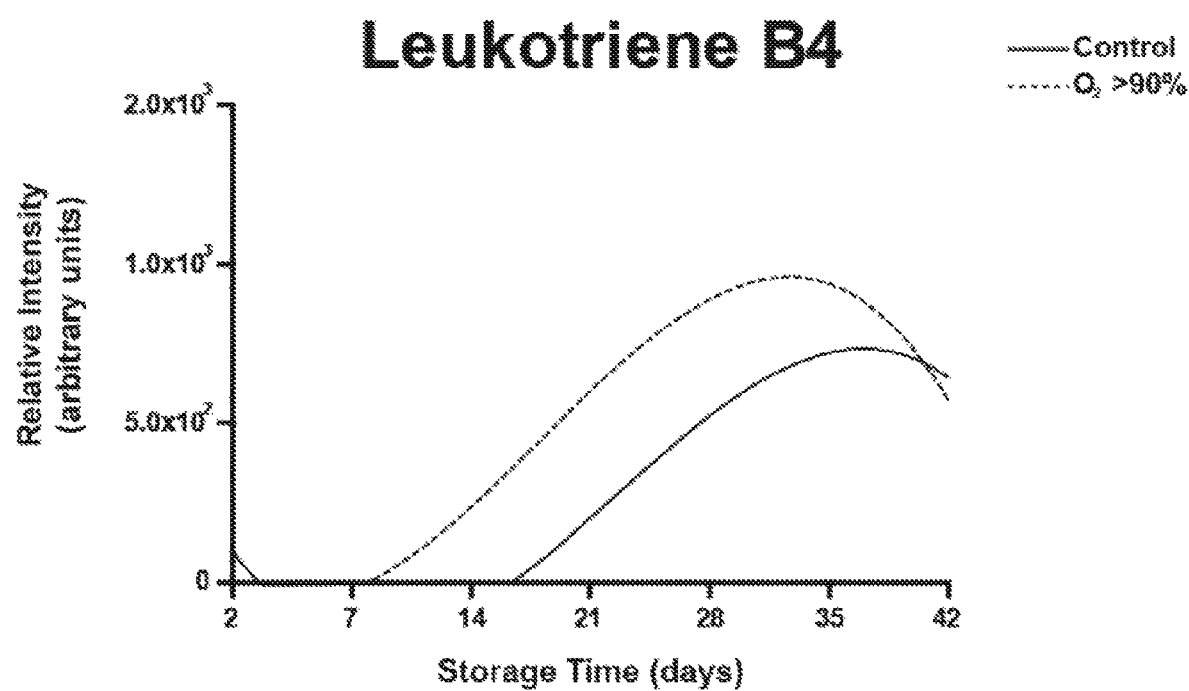

| Changed blood Molecule/pathway | SO2 range | Clinical Benefit | Date of Improvement (day) | | | | | | | Change† | FIG. |
|---|---|---|---|---|---|---|---|---|---|---|---|
| | | | 2 | 7 | 14 | 21 | 28 | 35 | 42 | | |
| | | due to increased O₂ content | | | | | | | | | |
| 2 Reduced Leukotriene B4 | <3-20, | Reduced levels of leukotriene B4, a highly pro-inflammatory BRM | | | X | X | X | X | X | below detection | FIG. 2 |
| 3 Reduced Thromboxane B2 | <3-5 | Reduction in platelet activation and vascular/bronchial smooth-muscle contraction. B2 is an end product, and more stable form of unstable thromboxane A2, and a potent BRM for platelet activator and smooth muscle contraction. | X | X | X | X | X | X | X | 1/2.1 at 7 d; 1/1.6 at 42 d | FIG. 3 |
| 4 Reduced HETE in cells | <3-20 | HETEs are pro-inflammatory BRMs | X | X | X | X | X | X | X | 1/5x 14 d to 1/20x 42 d | FIG. 4 |
| 5 Reduced HETE, supernatants | <3-10 | HETEs are pro-inflammatory BRMs | | | X | X | X | X | X | 1/5 at 14 d, 1/6 at 24 d | FIG. 4 |
| 6 Higher NADPH | <3-20 | Higher rate of NADP/H synthesis; higher anti-oxidant capacity; lower level of oxidative stress despite the reduced PPP flux due to metabolic modulation | | | | | X | X | X | 2.2x at 14 d, 5.9x at 42 d | FIG. 5 |
| 7 Higher NADPH/ NADP+ | <3-20 | Higher rate of NADP/H synthesis; higher anti-oxidant capacity; lower level of oxidative stress despite the reduced PPP flux due to metabolic modulation | | | | | X | X | X | 8.5x at day 42 | FIG. 6 |
| 8 Higher NADPH+ NADP reservoirs | <3-20 | Higher rate of NADP/H synthesis; higher anti-oxidant capacity; lower level of oxidative stress despite reduced PPP flux due to metabolic modulation | X | X | X | X | X | X | X | 1.7x at day 1 and 4.4x at 42 d | FIG. 7 |
| 9 Higher NADH/NAD reservoir | <3-20 | Higher rate of NAD/H synthesis; more reducing environment; higher antioxidant capacity | | | | X | X | X | X | 2.8x at 42 d | FIG. 8 |
| 10 Increased Methylenetetra-hydrofolate | <3-20 | May promote NADPH production | | | X | X | X | X | X | 1.4x at 14 d, 2x at 42 d | FIG. 9 |
| 11 Higher glutamate levels | <3-20 | Higher GSH + GSSG pool; Glutamate is a precursor for GSH synthesis | | | X | X | X | X | X | 1.2x at 2 d, 2.1x at 42 d | FIG. 10 |

TABLE 1-continued

Improvements and clinical benefits to oxygen reduced stored blood compared to conventional storage

Figure 11:
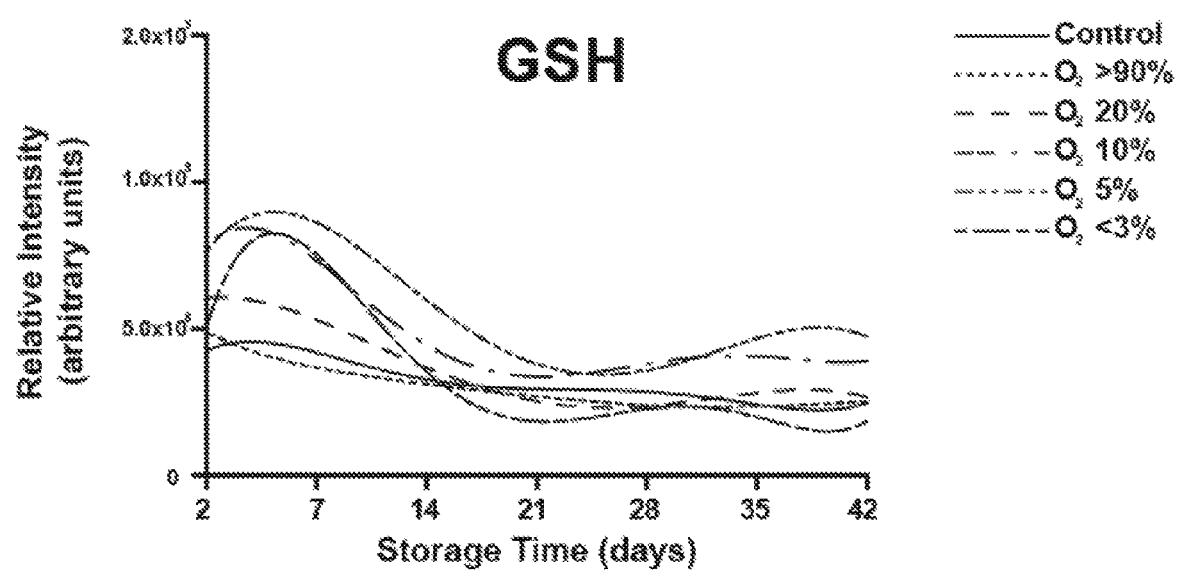
Figure 12:
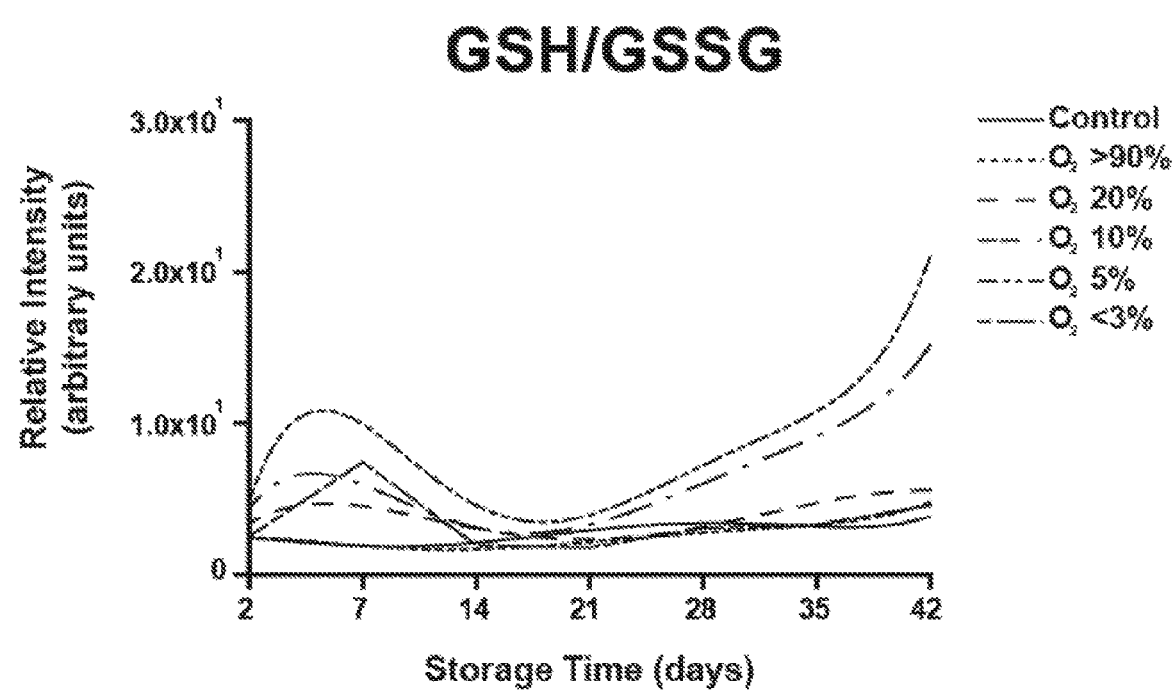
Figure 13:
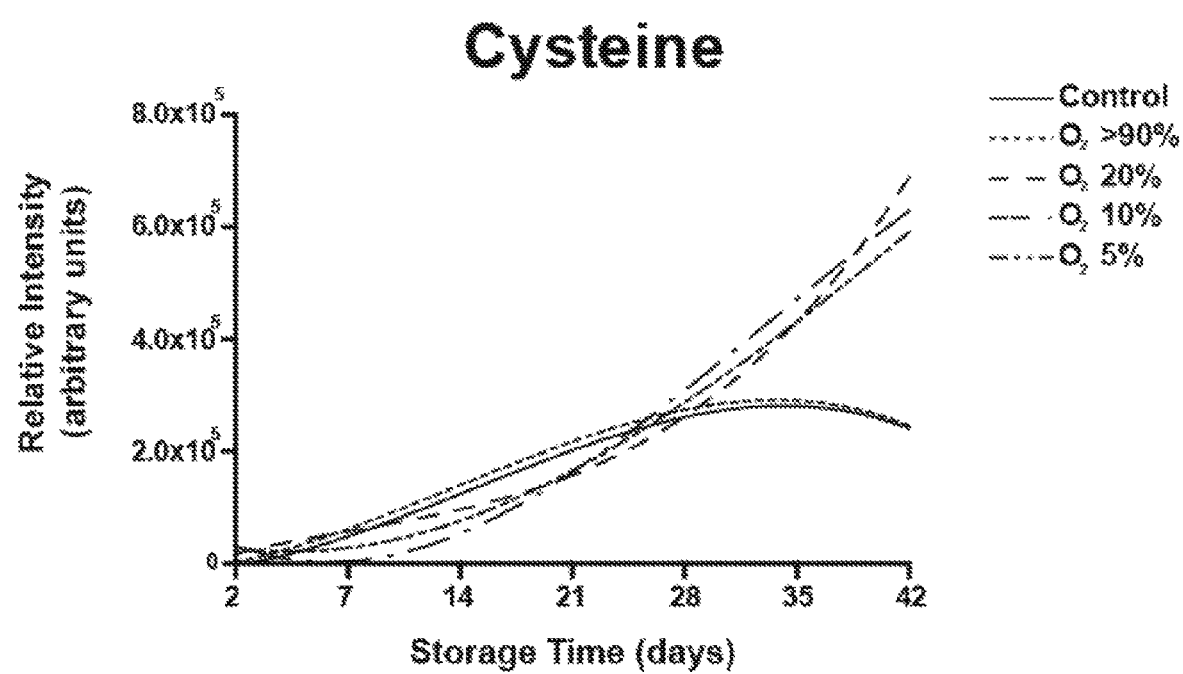
Figure 14:
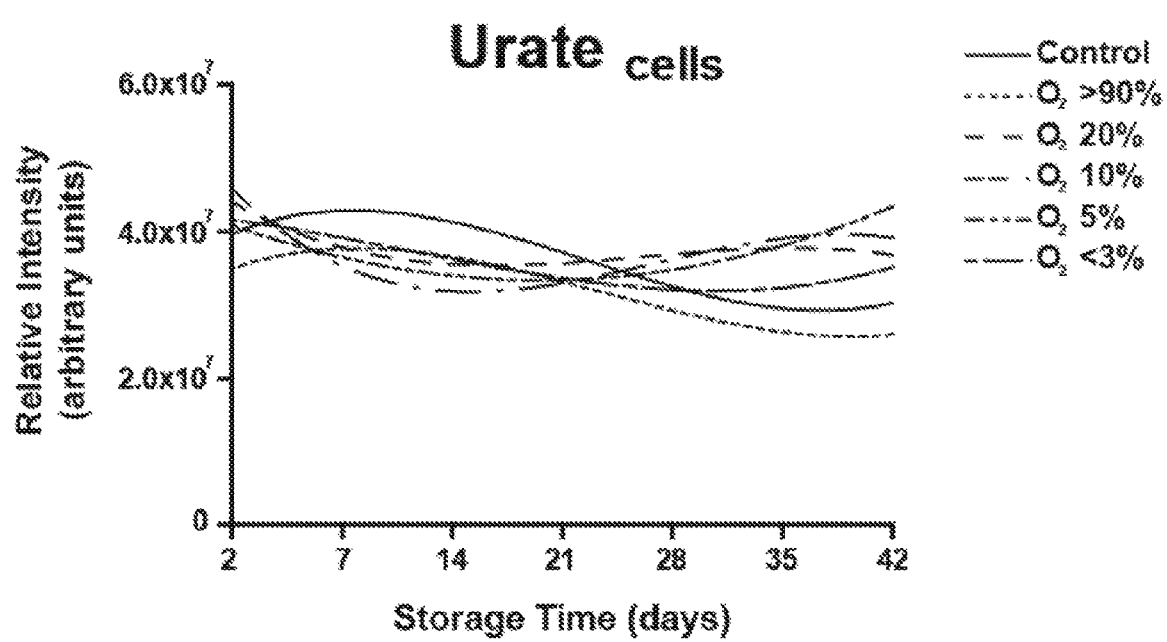
Figure 15:
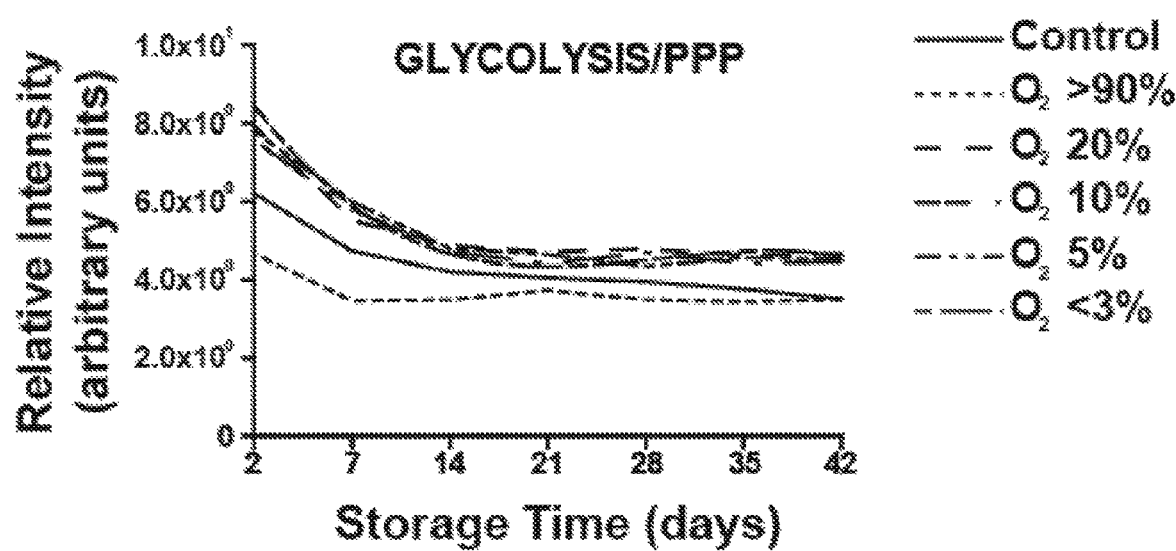
Figure 16:
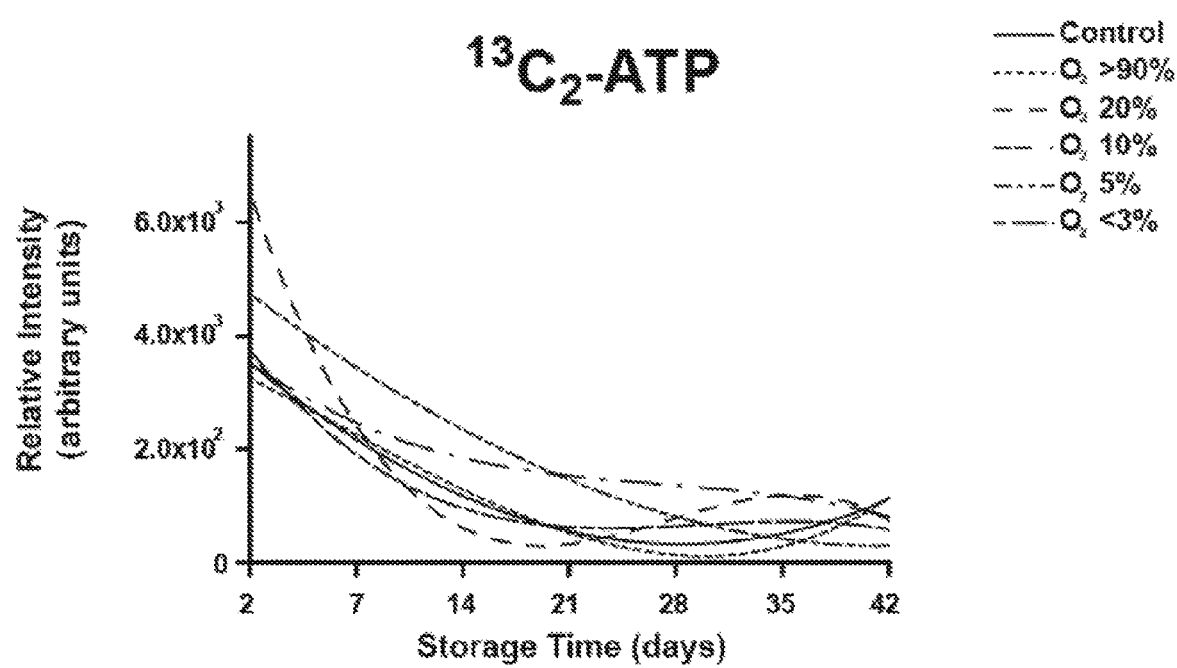
Figure 17:
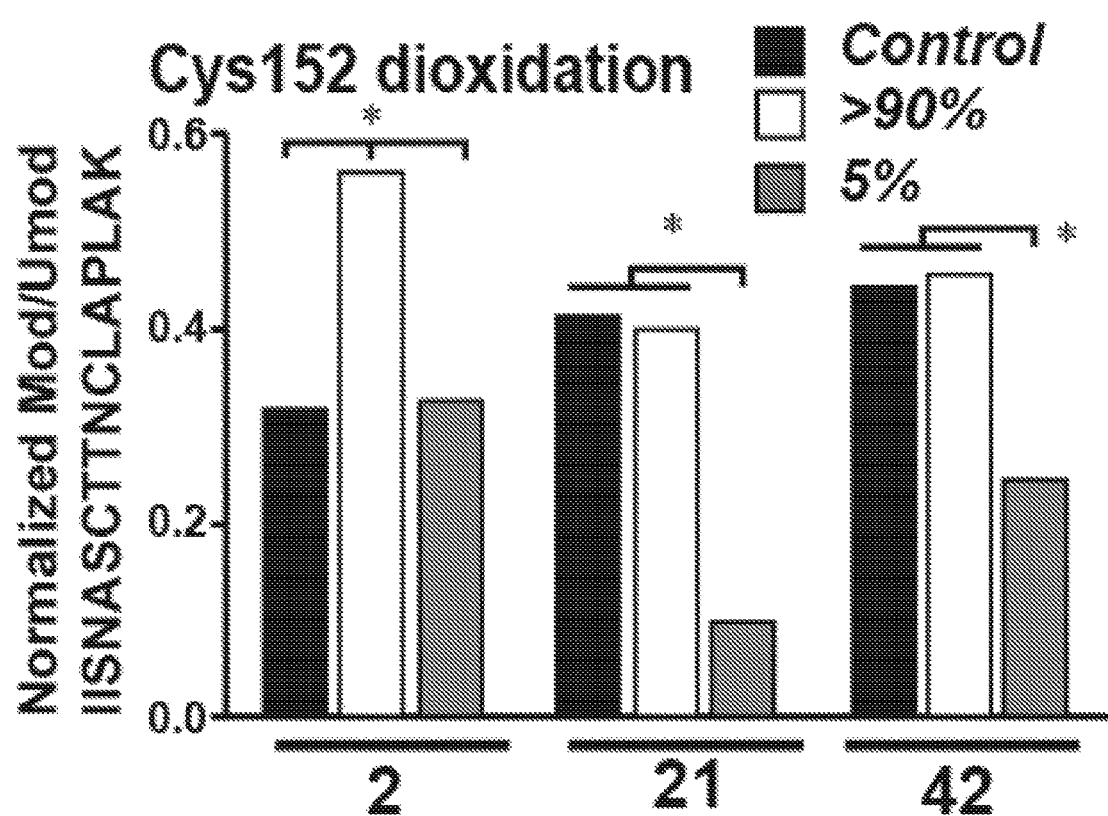
Figure 18A:
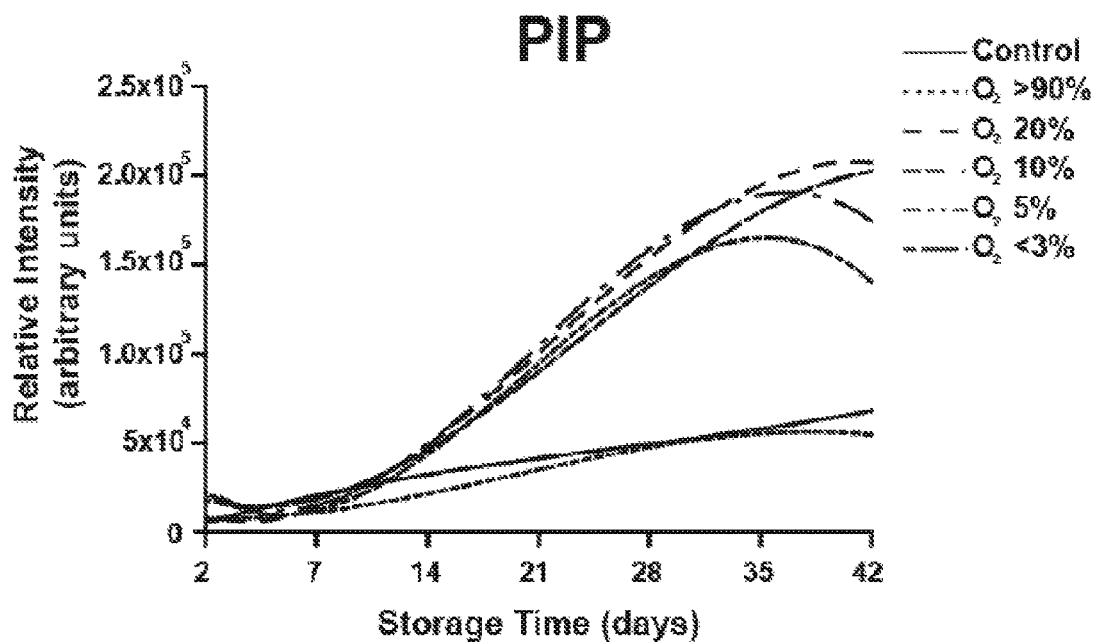
FIGS. 18A and 18B are graphs presenting the results of an experiment according to the present disclosure, comparing the phosphorylation of PIP to PIP3 in conventionally stored normoxic (solid line) and hyperoxic (---) and oxygen reduced stored blood with an initial an initial percent $SO_2$ of 20, 10, 5, and <3%.
Figure 18B:
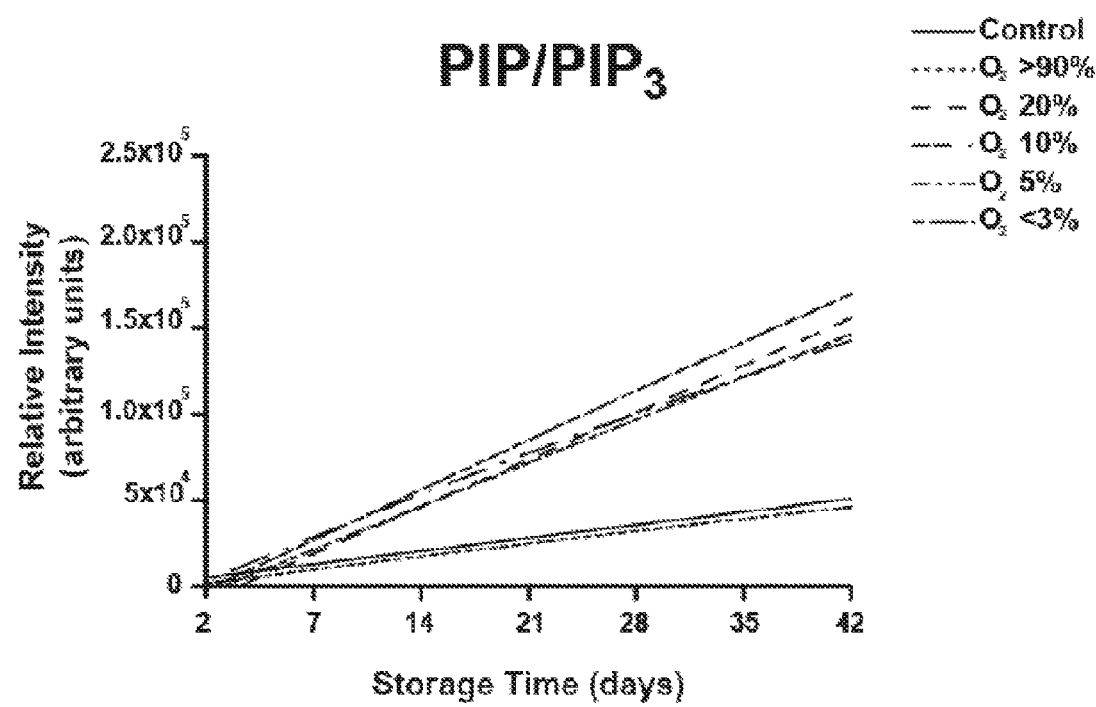
Figure 19:
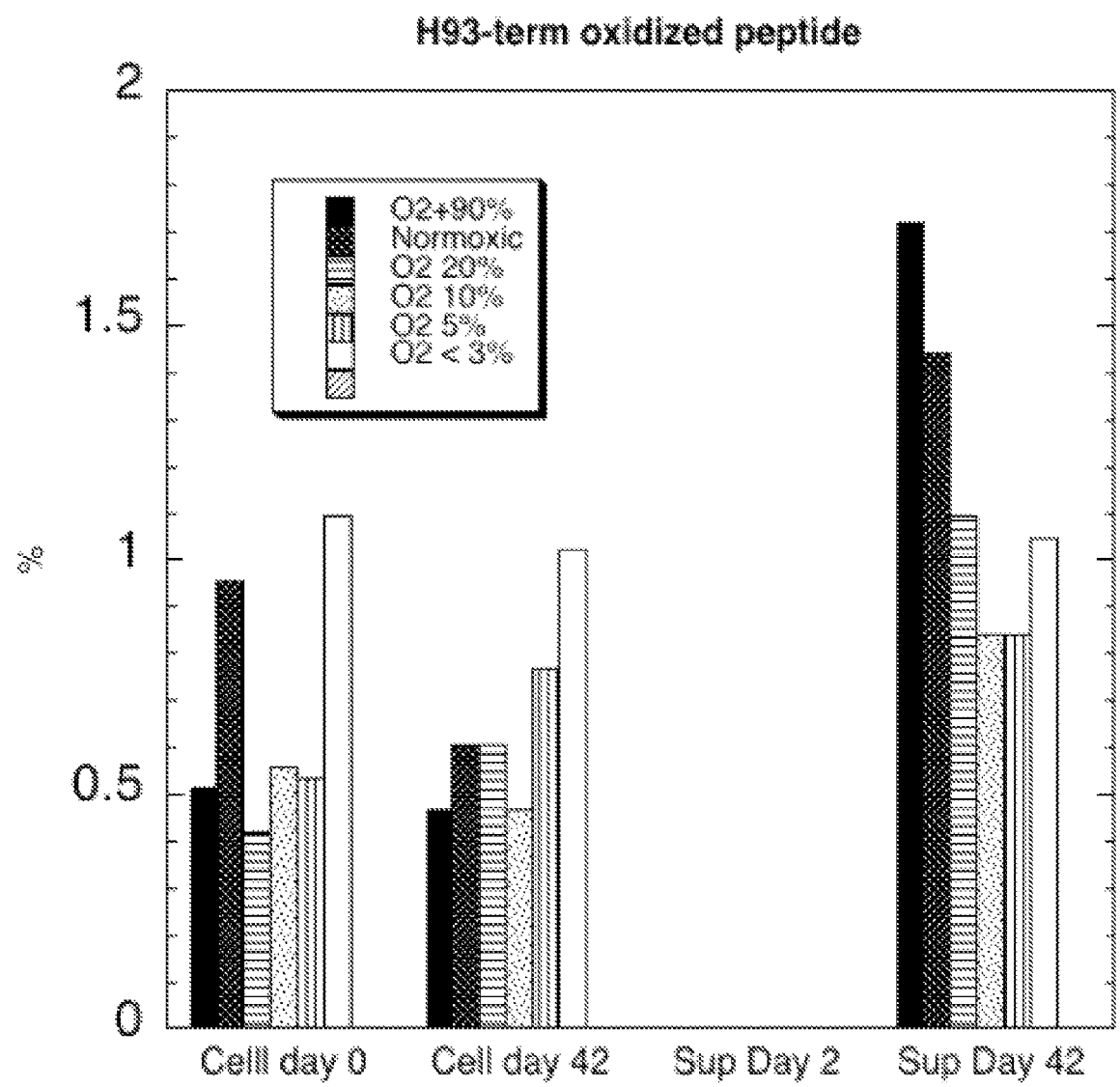
Figure 20:
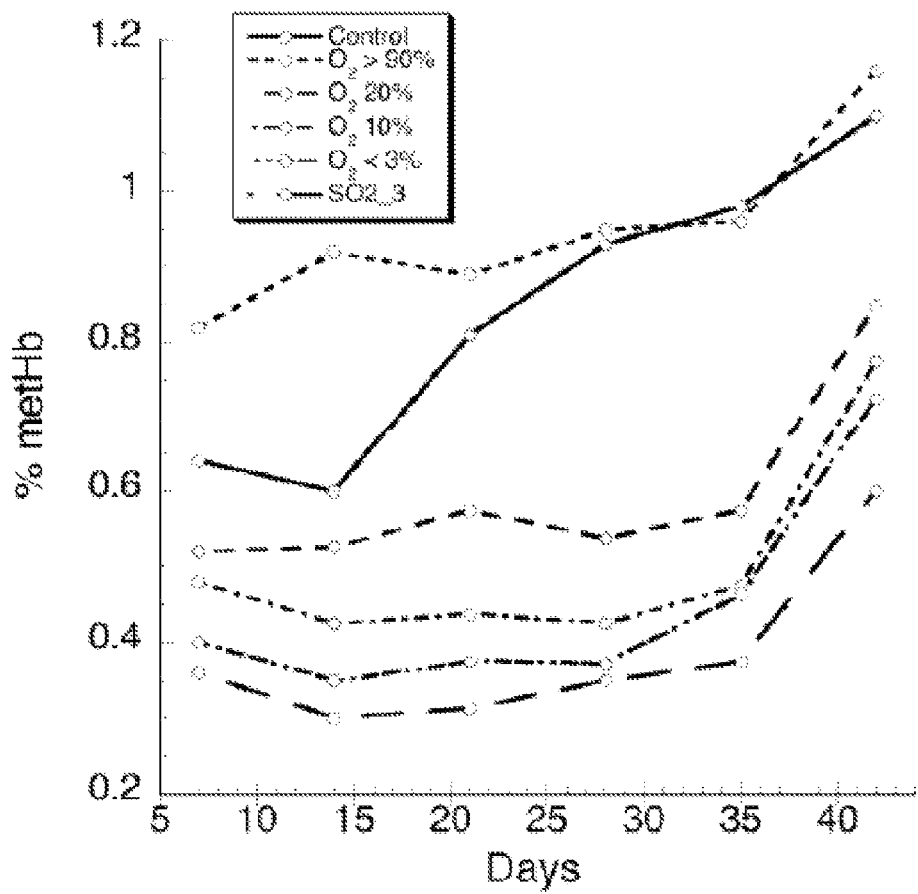

| | Changed blood Molecule/pathway | SO2 range | Clinical Benefit | \multicolumn{7}{c}{Date of Improvement (day)} | Change† | FIG. |
|---|---|---|---|---|---|---|---|---|---|---|---|---|
| | | | | 2 | 7 | 14 | 21 | 28 | 35 | 42 | | |
| 12 | Higher GSH levels | 5-20 | Higher antioxidant capacity; lower level of oxidative stress | X | X | X | X | X | X | X | 2x at day 7, 2.1x at 42 d | FIG. 11 |
| 13 | Higher GSH/GSSG ratio | 5-10 | Higher antioxidant capacity; lower level of oxidative stress | | | | X | X | X | X | 6x at day 7 d and 42 d | FIG. 12 |
| 14 | Increased cysteine | 5-20 | Higher GSH levels (rate limiting substrate for GSH synthesis) | | | | | X | X | X | 2.1x at 7 d, 1.9x at 42 d | FIG. 13 |
| 15 | Reduced depletion of urate | <3-20 | Urate is an antioxidant; higher levels in stored pRBC suggests lower oxidative stress | | | | | X | X | X | 1.4x at 42 d | FIG. 14 |
| 16 | Increased ATP and DPG production | <3-20 | Higher EMP flux generates higher levels of ATP and DPG | X | X | X | X | X | X | X | 1.5x lactate at 28 d | FIG. 15 |
| | Higher de novo ATP synthesis via PPP | | Higher total adenylate pool | X | X | X | X | X | X | | | FIG. 16 |
| 17 | Reduced Cys152 dioxidation level in GAPDH | 5 | Reduction in irreversibly oxidized GAPDH: such GAPDH loses enzymatic activity, loses ability for metabolic modulation, and migrates to membrane, causing vesiculation. | | | | X | X | X | X | 1/4.5 at 21 d; 1/1.7 at 42 d | FIG. 17 |
| 18 | Reduced PIP to PIP3 | 5-20 | Phosphorylation of PIP to the calcium channel agonist PIP3 is reduced under anaerobic conditions, reducing intracellular calcium levels, preventing morphological changes (H) and eryptosis (H). | | X | X | X | X | X | X | 3.3x PIP/PIP3 ratio | FIG. 18 |
| 19 | Reduced Hb betaH93 oxidation (especially in supernatant) | 5-10; <3-20 | Reduction in microparticle formation (H); reduction in unreactive hemoglobin (no O₂ binding); 5-10% SO2 is the most effective | | | | | | X | | 1/1.7 at 42 d | FIG. 19 |
| 20 | Lower methemoglobin levels | <3-20 | Methemoglobin is unstable and denatures into hydrophobic and reactive globin and hemin; they can disrupt RBC membrane, induce vesiculation, induce morphology change and catalyze | X | X | X | X | X | X | X | 1/4.2x at 15 d and 1/4.8x at 42 d | FIG. 20 |

TABLE 1-continued

Improvements and clinical benefits to oxygen reduced stored blood compared to conventional storage

| Changed blood Molecule/pathway | SO2 range | Clinical Benefit | Date of Improvement (day) | | | | | | | FIG. |
|---|---|---|---|---|---|---|---|---|---|---|
| | | | 2 | 7 | 14 | 21 | 28 | 35 | 42 Change† | |
| | | hydroxyl radical generation (highly reactive pro-oxidant molecules). | | | | | | | | |

†Fold change of oxygen reduced stored blood compared to conventional stored normoxic (control) blood having an identical storage period.
N/A = not applicable The present disclosure provides for, and includes, method for reducing the risk of an inflammatory response in a human patient in need of a blood transfusion comprising providing oxygen reduced stored blood that has an initial oxygen saturation of 20% or less prior to being stored for a storage period for transfusion to a human patient in need of a blood transfusion wherein said patient has an increased risk for an inflammatory response (see e.g., Table 1). In aspects according to the present disclosure, the oxygen reduced stored blood has a reduced level of at least one inflammatory factor. As used herein, initial oxygen saturation refers to the oxygen saturation of the blood prior to initiation of storage at 1 to 6° C. For conventional storage, the initial oxygen saturation of venous blood at collection and processing to red cell concentrate is about 50% and during the storage period, due to permeability of conventional storage bags, increases to fully saturated over a period of one to two weeks (see e.g., FIG. 1).

Without being limited to any scientific theory, among other changes, storage of red blood cells in aerobic environments promotes the vesiculation of the membrane, and infusion of microparticles into the circulatory environment, both during storage and after transfusion. However, generation and maintenance of oxygen reduced stored blood products increases overall membrane stability, through activation of the Lands cycle, as well as inhibiting activation of calcium ion channels, which are linked to cellular membrane scrambling and shedding. See FIG. 18. Additionally, oxygen reduced stored blood also has reduced levels of leukotriene B4 (see e.g., FIG. 2) and HETES (see e.g., FIG. 4), potent pro-inflammatory lipids. In one aspect, the use of oxygen reduced stored blood will prevent, or mitigate the pro-inflammatory effect of blood transfusion, especially on patients with pre-existing, inflammatory pathologies. In addition, oxygen reduced stored blood can prevent new pathologies such as transfusion related acute lung injury (TRALI) and systemic inflammatory response syndrome (SIRS)

Methods of the present disclosure provide for, and include, identifying a patient at risk of an inflammatory response, and providing the identified patient oxygen reduced stored blood that has an initial oxygen saturation of 20% or less prior to being stored for a storage period. As used herein, providing oxygen reduced stored blood includes, without limitation, whole blood and red blood cells as provided in the present disclosure.

Oxygen reduced stored blood that has an initial oxygen saturation of 20% or less prior to being stored for a storage period can be prepared with lower levels of oxygen. As provided by the present disclosure, certain improvements are evident beginning at an initial saturation level of 20%.

As used herein, improvements and benefits to the selected patients provided in the present disclosure are relative to (e.g., compared to) non-oxygen reduced stored blood stored for an identical storage period. Importantly, these differences become more pronounced as the storage period increases and as the initial oxygen saturation prior to storage is reduced.

In an aspect of the present disclosure, oxygen reduced stored blood having an initial oxygen saturation of 20% or less as identified in the preceding paragraphs and stored for at least 2 days has reduced leukotriene B4. In another aspect, oxygen reduced stored blood of the present disclosure further includes reduced thromboxane B2. In other aspects, the oxygen reduced stored blood of the present disclosure is oxygen reduced stored blood having reduced leukotriene B4, reduced thromboxane B2, and reduced HETEs. In further aspects, the oxygen reduced stored blood of the present disclosure is oxygen reduced stored blood having reduced leukotriene B4 and reduced HETEs. In other aspects, the oxygen reduced stored blood as identified in the present disclosure, further includes reduced leukotriene B4, thromboxane B2, and HETEs. In an aspect of the present disclosure, oxygen reduced stored blood suitable for reducing risks of an inflammatory response include oxygen reduced stored blood having reduced leukotriene B4, thromboxane B2, and HETEs. In another aspect, the oxygen reduced stored blood suitable for reducing risks of an inflammatory response further includes reduced methemoglobin, reduced oxidation of beta-hemoglobin at residue H93, increased reservoir of reduced nicotinamide adenine dinucleotide phosphate (NADPH), increased GSH, increased ATP, increased DPG, increased NADPH reservoir, reduced PIP to PIP3 ratio, increased methylene THF, increased glutamate, increased ratio of GSH to glutathione disulfide (GSSG) (GSH/GSSG ratio), increased urate, and increased cysteine. In another aspect, the oxygen reduced stored blood suitable for reducing risks of an inflammatory response further includes reduced methemoglobin. In another aspect, the oxygen reduced stored blood suitable for reducing risks of an inflammatory response further includes reduced oxidation of beta-hemoglobin at residue H93. In another aspect, the oxygen reduced stored blood suitable for reducing risks of an inflammatory response further includes increased reservoir of reduced nicotinamide adenine dinucleotide phosphate (NADPH). In another aspect, the oxygen reduced stored blood suitable for reducing risks of an inflammatory response further includes increased GSH. In another aspect, the oxygen reduced stored blood suitable for reducing risks of an inflammatory response further includes increased ATP. In another aspect, the oxygen reduced stored blood suitable for reducing risks of an inflammatory response further includes increased DPG. In another aspect, the oxygen reduced stored blood suitable for reducing risks of an inflammatory response further includes increased NADPH reservoir. In another aspect, the oxygen reduced stored blood suitable for reducing risks of an inflammatory response further includes reduced PIP to PIP3 ratio. In another aspect, the oxygen reduced stored blood suitable for reducing risks of an inflammatory response further includes increased methylene THF. In another aspect, the oxygen reduced stored blood suitable for reducing risks of an inflammatory response further includes increased glutamate. In another aspect, the oxygen reduced stored blood suitable for reducing risks of an inflammatory response further includes increased ratio of GSH to glutathione disulfide (GSSG) (GSH/GSSG ratio). In another aspect, the oxygen reduced stored blood suitable for reducing risks of an inflammatory response further includes increased urate. In another aspect, the oxygen reduced stored blood suitable for reducing risks of an inflammatory response further includes increased cysteine.

In an aspect of the present disclosure, oxygen reduced stored blood having an initial oxygen saturation of 10% and stored for at least 2 days has reduced leukotriene B4. In another aspect, oxygen reduced stored blood of the present disclosure further includes reduced thromboxane B2. In other aspects, the oxygen reduced stored blood of the present disclosure is oxygen reduced stored blood having reduced leukotriene B4, reduced thromboxane B2, and reduced HETEs. In further aspects, the oxygen reduced stored blood of the present disclosure is oxygen reduced stored blood having reduced leukotriene B4 and reduced HETEs. In further aspects, the oxygen reduced stored blood as identified in the present disclosure, further includes reduced leukotriene B4, thromboxane B2, and HETEs. Oxygen reduced stored blood suitable for reducing risks of an inflammatory response include oxygen reduced stored blood having reduced leukotriene B4, thromboxane B2, and HETEs.

In an aspect of the present disclosure, for example, oxygen reduced stored blood having an initial oxygen saturation of 5% or less and stored for at least 2 days has reduced leukotriene B4. In another aspect, oxygen reduced stored blood of the present disclosure further includes reduced thromboxane B2. In other aspects, the oxygen reduced stored blood of the present disclosure is oxygen reduced stored blood having reduced leukotriene B4, reduced thromboxane B2, and reduced HETEs. In further aspects, the oxygen reduced stored blood of the present disclosure is oxygen reduced stored blood having reduced leukotriene B4 and reduced HETEs. In further aspects, the oxygen reduced stored blood further includes reduced leukotriene B4, thromboxane B2, and HETEs. Oxygen reduced stored blood suitable for reducing risks of an inflammatory response include oxygen reduced stored blood having reduced leukotriene B4, thromboxane B2, and HETEs.

In an aspect of the present disclosure, oxygen reduced stored blood having an initial oxygen saturation of 3% or less and stored for at least 2 days has reduced leukotriene B4. In another aspect, oxygen reduced stored blood of the present disclosure further includes reduced thromboxane B2. In other aspects, the oxygen reduced stored blood of the present disclosure is oxygen reduced stored blood having reduced leukotriene B4, reduced thromboxane B2, and reduced HETEs. In further aspects, the oxygen reduced stored blood of the present disclosure is oxygen reduced stored blood having reduced leukotriene B4 and reduced HETEs. In further aspects, the oxygen reduced stored blood further includes reduced leukotriene B4, thromboxane B2, and HETEs. Oxygen reduced stored blood suitable for reducing risks of an inflammatory response include oxygen reduced stored blood having reduced leukotriene B4, thromboxane B2, and HETEs.

Methods of the present disclosure provide for, and include, identifying a patient having an increased risk of an inflammatory response and providing the identified patient oxygen reduced stored blood that has an initial oxygen saturation of 20% or less prior to being stored for a storage period. Methods also provide for providing oxygen reduced stored blood that has an initial oxygen saturation of 20% or less prior to being stored for a storage period for transfusion to a person having an increased risk of an inflammatory response. Also included are methods comprising transfusing oxygen reduced stored blood that has an initial oxygen saturation of 20% or less prior to being stored for a storage period to a patient having an increased risk of an inflammatory response. As discussed, as the storage period is increased, the improvements and benefits to the patients having an increased risk of an inflammatory response of transfusing oxygen reduced stored blood increase relative to blood stored using conventional methods. Accordingly methods providing oxygen reduced stored blood having an initial oxygen saturation of 20% or less include providing oxygen reduced stored blood having an initial oxygen saturation of 10% or less. Methods of providing oxygen reduced stored blood having an initial oxygen saturation of 20% or less further include providing oxygen reduced stored blood having an initial oxygen saturation of 5% or less. Methods of providing oxygen reduced stored blood having an initial oxygen saturation of 20% or less further include providing oxygen reduced stored blood having an initial oxygen saturation of 3% or less.

In some aspects the inflammatory factor is a protein. In an aspect, the inflammatory factor is a cytokine. In some aspects according to the present disclosure, the at least on inflammatory factor is at least one eicosanoid inflammatory mediator. Also provided herein, are reductions in at least one eicosanoid inflammatory mediator and at least one inflammatory cytokine. In an aspect according to the present disclosure, the oxygen reduced stored blood has been stored at least two days and provides for reduced levels of inflammatory factors. In an aspect, the inflammatory factors that are reduced include thromboxane B2 and hydroxyeicosatetraenoic acid (HETE). In a further aspect, the reduced levels of inflammatory factors include a biologic response modifier, such as RANTES, Eoxtaxin 1, soluble CD40-ligand (SCD40L), or combinations thereof.

In an aspect, methods of the present disclosure provide for, and include, providing oxygen reduced stored blood that has an initial oxygen saturation of 20% or less prior to being stored for a storage period to patients having an increased risk of an inflammatory response. In an aspect, a patient having an increased risk of an inflammatory response is a surgery patient requiring a tissue perfusion bypass. In an aspect, a patient having an increased risk of an inflammatory response is a patient having chronic vascular inflammation. In an aspect, a patient having an increased risk of an inflammatory response is a patient having chronic inflammatory bowel disease. In an aspect, a patient having an increased risk of an inflammatory response is a patient having chronic obstructive pulmonary disease (COPD). In an aspect, a patient having an increased risk of an inflammatory response is patient having sickle cell disease. In an aspect, a patient having an increased risk of an inflammatory response is a patient having thalassemia. In an aspect, the patient has α-thalassemia. In another aspect, the patient in need has β-thalassemia. In an aspect, a patient having an increased risk of an inflammatory response is a patient having organ failure. In an aspect, a patient having an increased risk of an inflammatory response is a patient having systemic inflammatory response syndrome (SIRS). In an aspect, a patient having an increased risk of an inflammatory response is a patient having diabetes mellitus. In an aspect, a patient having an increased risk of an inflammatory response is a patient having Behcet's disease. In an aspect, a patient having an increased risk of an inflammatory response is a patient having rheumatoid arthritis. In an aspect, a patient having an increased risk of an inflammatory response is patient having smoke inhalation. In an aspect, a patient having an increased risk of an inflammatory response is patient having ischemic heart disease.

Also provided for, and included are patients having a combination of underlying conditions. In an aspect, a patient having an increased risk of an inflammatory response has sickle cell and β-thalassemia. In an aspect, a patient having an increased risk of an inflammatory response has diabetes and COPD. In an aspect, a patient having an increased risk of an inflammatory response has sickle cell disease and SIRS. In an aspect, a patient having an increased risk of an inflammatory response has diabetes and ischemic heart disease. In an aspect, a patient having an increased risk of an inflammatory response has MODS and SIRS. In an aspect, a patient having an increased risk of an inflammatory response has COPD and ischemic heart disease. In an aspect, a patient having an increased risk of an inflammatory response is a trauma victim with an autoimmune disease. It will be appreciated by one of ordinary skill in the art that individual patients are evaluated for each of the risks separately. That is, the methods provided for refer to each individual risk, not as a list of risks for selection of a risk factor therefrom.

In certain aspects, methods of the present disclosure provide greater benefit to patients having more than one underlying condition that are aggravated by transfused blood having increased levels of inflammatory factors. In an aspect, a patient having an increased risk aggravating a preexisting condition has sickle cell and β-thalassemia. In an aspect, a patient having an increased risk of aggravating a preexisting condition has diabetes and COPD. In an aspect, a patient having an increased risk of aggravating a preexisting condition has sickle cell disease and SIRS. In an aspect, a patient having an increased risk of aggravating a preexisting condition has diabetes and ischemic heart disease. In an aspect, a patient having an increased risk of aggravating a preexisting condition has MODS and SIRS. In an aspect, a patient having an increased risk of aggravating a preexisting condition COPD and ischemic heart disease. In other aspects, a patient at risk of an underlying condition that is aggravated by transfused blood having increased levels of inflammatory factors is a patient with chronic inflammation due to sickle cell disease has inflammatory response worsened after chronic transfusion therapy. In an another aspect, a patient at risk of aggravating an underlying condition is a patient with hemolytic anemia from sickle cell and/or thalassemia has anemia worsened by DHTR after therapeutic transfusion. In yet another aspect, a patient at risk of aggravating an underlying condition is a patient with systemic inflammation resulting from obesity and diabetes has increased inflammatory response worsened after blood transfusion. In another aspect, a patient at risk of aggravating an underlying condition is a patient suffering from SIRS due to trauma or infection, has worsened inflammatory response after receiving transfusion. In an aspect, a patient at risk of aggravating an underlying condition is a patient with ischemic heart disease who receives a transfusion during surgery can have increased tissue damage as the result of transfusion of reactive oxygen species and inflammatory biomolecules. As provided herein, oxygen reduced stored blood of the present disclosure provides for reduced levels of inflammatory factors beginning at least as early as day two of a storage period. As used herein, "aggravated" refers to increased inflammation of a pre-existing inflammatory condition. In an aspect of the present disclosure, a patient having aggravated response is a patient having an underlying low grade inflammatory condition arising from diabetes, an autoimmune disease, or trauma.

Methods of the present disclosure provide for, and include, for providing oxygen reduced stored blood to a patient having chronic vascular inflammation. Without being limited to any scientific theory, chronic vascular inflammation is a co-morbidity associated with several degenerative disorders such as sickle cell disease, hematological cancers, diabetes, and heart disease. In these pro-inflammatory conditions, it has been shown that red blood cells can initiate or propagate pro-inflammatory signals through release of membrane microparticles containing bioactive kinases and other signaling molecules. These microparticles can be taken up by circulating monocytes, stimulating release of TNF-α, IL-1β, and IL-6; furthermore, uptake of RBC secreted microparticles also promotes monocyte-endothelial adhesion. See Awojoodu et al., "Acid sphingomyelinase is activated in sickle cell erythrocytes and contributes to inflammatory microparticle generation in SCD," Blood 124 (12):1941-50 (2014) (hereby incorporated by reference in its entirety). However, chronic inflammatory disorders can be further aggravated by transfusion of conventional red blood cell products through the course of normal therapy paradigms, or surgical intervention. In addition, phosphatidylserine (PS)-exposing microparticles produced as consequences of RBC storage or eryptosis can be responsible for increased inflammation in recipients. See Saas et al., "Phosphatidylserine-expressing cell by-products in transfusion: A pro-inflammatory or an anti-inflammatory effect?" Transfusion Clinique et Biologique 19(3):90-97 (2012) (hereby incorporated by reference in its entirety).

Methods of the present disclosure provide for, and include, for providing oxygen reduced stored blood to a patient having chronic inflammatory bowel disease. A patient with chronic inflammatory bowel disease, such as ulcerative colitis and Crohn's disease, is characterized by chronically activated intestinal inflammation as the result of elevated recruitment of neutrophils from the circulatory environment to the intestinal lumen. See Nielsen et al., "Activation of neutrophil chemotaxis by leukotriene B4 and 5-hydroxyeicosatetraenoic acid in chronic inflammatory bowel disease," Scandinavian Journal of Clinical and Laboratory Investigation 47(6):605-611 (1987) (Nielsen et al. (1987) (hereby incorporated by reference in its entirety)). Upon recruitment, neutrophils secrete inflammatory cytokines and chemokines that promote recruitment of additional immune cells, further exacerbating the inflammatory response. Without being limited by theory, initial and continued activation and recruitment of neutrophils in IBD is, in part, the result of hydroxyeicosatetraenoic acids (HETE). See Nielsen et al. (1987) and Nielsen et al., "Release of leukotriene B4 and 5-hydroxyeicosatetraenoic acid during phagocytosis of artificial immune complexes by peripheral neutrophils in chronic inflammatory bowel disease," Clin.

Exp. Immunol 65(2):465-471 (1986) (hereby incorporated by reference in their entireties). As shown in the present disclosure, oxygen reduced stored blood contains lower concentrations of HETE acids (see e.g., FIG. 4). In addition, oxygen reduced stored blood has reduced levels of leukotriene B4 (see e.g., FIG. 2), which has been shown to be elevated in patients suffering from ulcerative colitis. Patients with a chronic IBD, such as ulcerative colitis and Crohn's disease that received a transfusion of oxygen reduced stored blood have a reduced exposure to HETE acids and leukotriene B4, decreasing activation and recruitment of neutrophils into the circulatory environment, and potentially decreasing the risk of secondary inflammation of the intestinal wall.

Methods of the present disclosure provide for, and include, for providing oxygen reduced stored blood to a patient having chronic obstructive pulmonary disease (COPD). People who suffer from chronic obstructive pulmonary disease (COPD) develop persistent bacterial colonization of the airways (termed chronic colonization). See Monso et al., "Bacterial infection in chronic obstructive pulmonary disease. A study of stable and exacerbated outpatients using the protected specimen brush," American Journal of Respiratory and Critical Care Medicine 152(4): 1316-1320 (1995) and Crooks et al., "Bronchial inflammation in acute bacterial exacerbations of chronic bronchitis: the role of leukotriene B4," European Respiratory Journal 15(2):274-280 (2000) (Crooks et al. (2000) (hereby incorporated by reference in their entireties)). This chronic colonization contributes to the morbidity associated with COPD through chronic airway inflammation leading to decreased lung function. Studies have shown COPD patients with chronic bacterial infections have measurably higher levels of leukotriene B4 in the sputum (mixture of saliva and mucus coughed up from the respiratory tract during infection), which is a potent pro-inflammatory cytokine associated with activation of primary immune cells. See Crooks et al. (2000). Rapid progression of COPD may require surgical intervention necessitating blood transfusion to the patient; the present disclosure provides that oxygen reduced stored blood has reduced levels of leukotriene B4 (see e.g., FIG. 2) relative to conventionally stored blood. Provided herein is transfusion using oxygen reduced stored blood during interventional surgeries can decrease the risk of exacerbating pulmonary obstruction and promoting superior lung function.

Methods of the present disclosure provide for, and include, for providing oxygen reduced stored blood to a patient having sickle cell disease. Development of vascular occlusive events, which are the main cause of the morbidity and mortality in sickle cell disease, results from the chronically inflamed vascular environment characterized by elevated levels of inflammatory cytokines, such as TNFα, as well as increased numbers of circulating white blood cells, such as neutrophils and monocytes. See Setty et al., "Sickle red blood cells stimulate endothelial cell production of eicosanoids and diacylglycerol," Journal of Laboratory and Clinical Medicine 128(3):313-321 (1996); Lum et al., "Inflammatory potential of neutrophils detected in sickle cell disease," American Journal of Hematology 76(2):126-33 (2004); Pathare et al., "Cytokine profile of sickle cell disease in Oman," American Journal of Hematology 77(4):323-8 (2004); Finnegan et al., "Adherent leukocytes capture sickle erythrocytes in an in vitro flow model of vaso-occlusion," American Journal of Hematology 82(4):266-75 (2007); and Montes et al., "Sickle erythrocyte adherence to endothelium at low shear: Role of shear stress in propagation of vaso-occlusion," American Journal of Hematology 70(3):216-27 (2002) (hereby incorporated by reference in their entireties). Additionally, without being limited by theory, circulating neutrophils are activated due to exposure to hydroxyeicosatetraenoic (HETEs) acids, as well as leukotriene B4. Administration of blood transfusion is a common therapeutic for the treatment and resolution of vaso-occlusive crises in sickle cell disease. The present disclosure provides that oxygen reduced stored blood has reduced levels of HETE acids and leukotriene B4 (see e.g., FIG. 4 and FIG. 2) relative to conventionally stored blood. Transfusion of oxygen reduced stored blood can be more efficacious at resolving the vascular crises, as well as further preventing the development of later crises, by decreasing the patient exposure to pro-immune activating molecules.

Methods of the present disclosure provide for, and include, for providing oxygen reduced stored blood to a patient having thalassemia. A patient with α- or β-thalassemia major is unable to produce functional hemoglobin molecules, resulting in severe anemia and necessitating transfusion of red blood cells (RBCs). A result of requiring regular (i.e., chronic) transfusions, people with thalassemia can suffer from delayed hemolytic transfusion reaction (DHTR) which is characterized by a rapid decrease in hematocrit following therapeutic transfusion. In one aspect, DHTR can be initiated as a response to sudden eryptosis, leading to rapid removal of the circulating red cells by macrophages and monocytes.

Without being limited by theory, it is thought that one trigger for eryptosis is accrued oxidative damage, a known consequence of conventional red blood cell storage. See Bhaysar et al., "Janus Kinase 3 is Expressed in Erythrocytes, Phosphorylated Upon Energy Depletion and Involved in the Regulation of Suicidal Erythrocyte Death," Cellular Physiology and Biochemistry 27(5): 547-556 (2011) (hereby incorporated by reference in its entirety). Reduced oxygen stored blood cells have superior anti-oxidative protection, as evidenced by increased NADPH reservoirs (see e.g., FIG. 5, FIG. 6, and FIG. 7), elevated levels of cysteine (see e.g., FIG. 13), elevated ratios of GSH to GSSG (see e.g., FIG. 12).

Furthermore, without being limited to theory, eryptosis is also promoted when red cells no longer have sufficient levels of ATP, which also occurs during conventional storage. See Gürer et al. "Arachidonic acid metabolites and colchicine in Behcet's disease (BD)" *Prostaglandins, leukotrienes, and essential fatty acids* 43(4):257-9 (1991) (hereby incorporated by reference in its entirety). However, oxygen reduced stored blood has improved overall ATP levels (see e.g., FIG. 16), and improved metabolic activity by sustaining glycolysis through the pentose phosphate pathway (see e.g., FIG. 15).

Use of anaerobic stored blood products for chronic therapeutic transfusions for people with α- or β-thalassemia can have a decreased risk of developing DHTR due to the increased protection from oxidative damage, and superior preservation of intracellular energy (ATP), and a further potential benefit of decreasing the frequency at which transfusions are required.

Methods of the present disclosure provide for, and include, providing oxygen reduced stored blood to a patient having systemic inflammatory response syndrome (SIRS). A patient is deemed to have systemic inflammatory response syndrome (SIRS) if two of the following criteria are met: body temperature higher than 38° C. or lower than 36° C., heart rate faster than 90 beats per minute (BPM), respiratory rate greater than 20 breaths per minute, arterial $CO_2$ tension of less than 32 mmHg, and abnormal white cell (either above 12,000 cells/4 or below 4,000 cells/4. See Lang, E. et al., "Killing me softly—suicidal erythrocyte death," The International *Journal of Biochemistry & Cell Biology,* 44(8): 1236-43 (2012) and Di Gennaro et al., "Targeting leukotriene B4 in inflammation," *Expert opinion on therapeutic targets.* 18(1) 79-93 (2014) (hereby incorporated by reference in their entireties). SIRS can develop as the result of an infectious agent such as bacterial infections, influenza, infective endocarditis, as well as non-infectious sources, such as severe burns, autoimmune disorders, hemorrhagic shock, hematologic malignancy, and chemical exposure. A patient currently suffering from SIRS can have the condition exacerbated if the patient also receives a blood transfusion, due to the presence of inflammatory biomolecules and cytokines within the blood unit. As provided by the present specification, oxygen reduced stored blood has decreased levels of inflammatory factors, such as hydroxyeicosatetraenoic acids (HETEs), and leukotriene B4 (see e.g., FIG. 2 and FIG. 4). Accordingly, a patient with SIRS can be provided with a transfusion of oxygen reduced stored blood can provide a reduced exposure to HETE acids and leukotriene B4, decreasing activation and recruitment of circulating neutrophils into the circulatory environment, and decreasing the risk of long-term organ system damage.

Additionally, since conventionally stored blood contains detectable levels of pro-inflammatory cytokines and biomolecules, a transfusion of conventionally stored blood can result in the development of SIRS. Use of oxygen reduced stored blood, with markedly reduced inflammatory biomolecules, has a considerably lower risk for the de novo initiation of SIRS in a hospitalized patient. This is a considerable advantage as previous studies have indicated that development of SIRS results in an approximately 7 day higher mortality, compared to non-SIRS patients. See Gürer, M. A. et al., "Arachidonic acid metabolites and colchicine in Behçet's disease (BD)," Prostaglandins, leukotrienes, and essential fatty acids. 43(4) 257-259 (1991) (hereby incorporated by reference in its entirety).

Methods of the present disclosure provide for, and include, for providing oxygen reduced stored blood to a patient having Behcet's disease. Behcet's Disease, also known as Behcet's syndrome, is a rare, chronic, autoinflammatory disorder of unknown origin. Its manifestations are thought to be caused by vasculitis resulting in damage to blood vessels throughout the body, and is characterized by oral or skin lesions, ocular inflammation, arthritis, and gastrointestinal lesions. Current research suggests viral, bacterial, genetic and environmental factors may play a role in the development of Behcet's Disease, but no specific cause has been established and no triggers have been identified. As a result of the chronic inflammation, people with Behcet's disease have increased serum levels of leukotrienes which are potent activators of circulating white blood cells, such as neutorphils. See Lang. et al., "Oxidative Stress and Suicidal Erythrocyte Death," Antioxidants Redox Signaling 21(1): 138-153 (2014). As provided by the present disclosure, oxygen reduced stored blood contains lower concentrations leukotriene B4 and HETEs (see e.g., FIG. 2 and FIG. 4). Therefore, a patient with Behcet's disease that received a transfusion of oxygen reduced stored blood can have a reduced exposure to HETE acids and leukotriene B4, decreasing activation and recruitment of circulating neutrophils into the circulatory environment, and potentially decreasing the risk of complications and secondary morbidities associated with chronic systemic inflammation.

Methods of the present disclosure provide for, and include, providing oxygen reduced stored blood to a patient having rheumatoid arthritis. Rheumatoid arthritis is a chronic autoimmune disease that characteristically involves the small joints of the hands and feet. As the disease progresses, a patients' cartilage and bone will begin to degrade in the synovial space of the joint, characterized by hyperplastic, invasive tissue containing large amounts of immunocompetent cells, such as T lymphocytes, memory B lymphocytes, and macrophages. Leukotrienes are inflammatory lipids that are among the most potent endogenous chemotactic agents for leukocytes yet identified, and are strongly implicated in the recruitment of immune cells to the synovial tissue in rheumatoid arthritis. See Wellen, K. E. et al., "Inflammation, stress, and diabetes," The Journal of clinical investigation. 115(5): 1111-1119 (2005) (hereby incorporated by reference in its entirety). For a patient with rheumatoid arthritis, a transfusion of blood has the potential to exacerbate their condition as a result of transfusing the accumulation of inflammatory biomolecules and cytokines within conventionally stored blood units. However, as provided in the present disclosure, oxygen reduced stored blood has lower concentrations of inflammatory factors, such as leukotriene B4 and HETEs (see e.g., FIG. 2 and FIG. 4). Therefore, patients with rheumatoid arthritis can be provided a transfusion of oxygen reduced stored blood that will avoid being exposed to powerful, exogenous pro-inflammatory molecules, thereby allowing for a reduced risk of aggravating or worsening the severity of the arthritic condition.

Methods of the present disclosure provide for, and include, providing oxygen reduced stored blood to a patient having smoke inhalation. Damage to the lungs and respiratory tract is one of the leading causes of death associated with fires. The lung injury process is activated by toxins in the smoke's gas and particle components and perpetuated by a resulting lung inflammation. This inflammatory process becomes self-perpetuating through the activation of a large number of inflammatory cascades, and increased plasma levels of inflammatory cytokines. See Park, G. Y. et al. "Prolonged airway and systemic inflammatory reactions after smoke inhalation," Chest. 123(2):475-480 (2003) (hereby incorporated by reference in its entirety). In addition, smoke injury leads to significant systemic abnormalities injuring other organs and accentuating the burn injury process and subsequently leading to mediator-induced cellular injury and further leading potentially to multisystem organ failure. After severe trauma, such as a smoke inhalation, the patient can require blood transfusion; however, the measurable increases in inflammatory molecules in conventionally stored blood can have a negative impact on patient outcomes and morbidity. Moreover, increases in the levels of metabolites correlate with poorer post-transfusion recoveries in a mouse model of red blood cell storage (de Wolski et al. "Metabolic pathways that correlate with post-transfusion circulation of stored murine red blood cells," *Haematologica,* 101(5): 578-586 (2016) (hereby incorporated by reference in its entirety). However, use of oxygen reduced stored blood can introduce decreased levels of inflammatory molecules, such as HETE and leukotriene B4 (see e.g., FIG. 2 and FIG. 4). As provided in the present disclosure, oxygen reduced stored blood can be used to prevent further exacerbation of the elevated inflammatory response from smoke inhalation, and provide superior patient outcomes and recoveries.

Methods of the present disclosure provide for, and include, a method of reducing the risk of an inflammatory response in a human patient in need of multiple blood units (e.g., more than 4) or massive transfusion (10 or more units). In an aspect, the selected patients requiring a massive transfusion with oxygen reduced stored blood reduces or does not aggravate a pre-existing inflammatory state. In an aspect, a trauma patient requiring multiple units or a massive transfusion is a patient with pre-existing disease who is pre-disposed to low-grade chronic systemic inflammation. In an aspect, the human patient has diabetes mellitus, Behcet's disease, rheumatoid arthritis, COPD, smoke inhalation and atherosclerosis. Patients with these conditions can have existing primed inflammatory leukocytes prior to the event requiring RBC transfusion. Infusion of HETEs, leukotrienes and thromboxanes in transfused RBC on already primed immune system will increase risk of morbidities such as multiple organ dysfunction (MODS), SIRS, and TRALI. Further, higher transfusion volume proportionally increases the dose and exaggerates the effects. Thus, patients can be provided with oxygen reduced stored RBC as a transfusion, having reduced infusion of HETEs, leukotrienes and thromboxanes and reduce the probability of morbidity.

As used herein, a patient having an increased risk of an inflammatory response is a patient having one or more conditions that are aggravated by increased levels of inflammatory factors. In an aspect, a patient having an increased risk of aggravating an existing inflammatory response is a patient having chronic vascular inflammation. In an aspect, a patient having an increased risk aggravating an inflammatory response is a patient having chronic inflammatory bowel disease. Also provided for, and included, are patients having a combination of underlying conditions. In certain aspects, methods of the present disclosure provide greater benefit to patients having more than one underlying condition that are aggravated by transfused blood having increased levels of inflammatory factors.

The present disclosure provides for, and include, reductions in adverse events following transfusion of oxygen reduced stored blood to a patient at risk of an inflammatory response. In an aspect, the patient receiving a transfusion of oxygen reduced stored blood has a reduced risk of a delayed hemolytic reaction.

The present disclosure provides for, and includes, reductions in adverse events following transfusion of oxygen reduced stored blood to a patient at risk of an inflammatory response having a reduced risk of transfusion related acute lung injury (TRALI). TRALI presents clinically with rapid onset of dyspnea (labored breathing) and tachypnea (abnormally rapid breathing). Additionally, patients can also present with fever, cyanosis, and hypotension. Clinical examination of the patients can reveal pulmonary crackles (auditory "crackling" when the patient is breathing) independent of signs of congestive heart failure. Chest X-Rays can reveal evidence of bilateral pulmonary edema not associated with heart failure, and bilateral patchy infiltrates which can progress to Acute Respiratory Distress Syndrome (ARDS). The present methods provide for a reduction of risk through at least the presentation of reduced levels of inflammatory factors, including, but not limited to leukotriene, 8-isoprostane, thromboxane, hydroxyeicosatetraenoic acid (HETE), and combinations thereof. In certain aspects, the present methods include reduced or ameliorated (not increased) levels of cytokines. As discussed, increases in the storage period provide further improvements of methods of the present disclosure when compared to conventionally stored blood.

The present disclosure provides for, and includes, a reduction in adverse events following transfusion by providing oxygen reduced stored blood to a patient at risk of an inflammatory response. In an aspect, methods of the present disclosure provides for a reduced incidence of systemic inflammatory response syndrome (SIRS). In an aspect, a patient is deemed to have SIRS if two of the following criteria are met: body temperature higher than 38° C. or lower than 36° C., heart rate faster than 90 BPM, respiratory rate greater than 20 breaths per minute, arterial $CO_2$ tension of less than 32 mmHg, and abnormal white cell (either above 12,000 cells/4 or below 4,000 cells/4. See Lang et al., "Killing me softly—suicidal erythrocyte death," International journal of biochemistry & cell biology 44(8):1236-43 (2012) (hereby incorporated by reference in its entirety). SIRS can develop as the result of an infectious agent such as bacterial infection, influenza, infective endocarditis, as well as non-infectious sources, such as severe burns, autoimmune disorders, hemorrhagic shock, hematologic malignancy, and chemical exposure. A patient currently suffering from SIRS can have the condition aggravated if the patient also receives a blood transfusion, due to the presence of inflammatory biomolecules and cytokines within the blood unit. As provided in the present disclosure, oxygen reduced stored blood can be provided that has decreased levels of inflammatory factors, such as hydroxyeicosatetraenoic acid (HETE), and leukotriene B4 (see e.g., FIG. 2 and FIG. 4). Therefore, a patient with SIRS that receives a transfusion of oxygen reduced stored blood will have a reduced exposure to HETEs and leukotriene B4, decreasing activation and recruitment of circulating neutrophils into the circulatory environment, and potentially decreasing the risk of long-term organ system damage.

The present disclosure provides for, and includes, reductions in adverse events following transfusion of oxygen reduced stored blood to a patient at risk of an inflammatory response having a reduced risk of multiple organ dysfunction syndrome (MODS). As used herein, MODS refers to the development of potentially reversible physiologic derangement involving two or more organ systems not involved in the primary insult that resulted in the patient's hospitalization. Clinically, MODS is scored based on physiological measurements made from 6 key organ systems, with higher scores indicating a lower level of organ function. See Table 2.

TABLE 2

The Multiple Organ Dysfunction (MOD) Score

| Organ system | 0 | 1 | 2 | 3 | 4 |
|---|---|---|---|---|---|
| Respiratory[a] | | | | | |
| ($PO_2$/$FOP_2$ Ratio) | >300 | 226-300 | 151-225 | 76-150 | ≤75 |
| Renal[b] | | | | | |
| (Serum Creatinine) | ≤100 | 101-200 | 201-350 | 351-500 | >500 |
| Hepatic[c] | | | | | |
| (Serum Bilirubin) | ≤20 | 21-60 | 61-120 | 121-240 | >240 |
| Cardiovascular[d] | | | | | |
| (R/P Ratio) | ≤10.0 | 10.1-15.0 | 15.1-20.0 | 20.1-30.0 | >30.0 |
| Hematologic[e] | | | | | |
| (Platelet count) | >120 | 81-120 | 51-80 | 21-50 | ≤20 |
| Neurologic[f] | | | | | |

From John C. Marshall, M.D., The multiple organ dysfunction syndrome from Surgical Treatment: Evidence-Based and Problem Oriented (Holzheimer and Mannie ed., W. Zuckschwerdt Verlag GmbH. 2001). Available from at www.ncbi.nlm.nih.gov/books/NBK6868/.

Although there is no specific etiology, severe, chronic inflammation has been associated with MODS development in patients in the intensive care unit. Systemic inflammation can develop as the result of an infectious agent such as bacterial infections, influenza, infective endocarditis, as well as non-infectious sources, such as severe burns, autoimmune disorders, hemorrhagic shock, hematologic malignancy, and chemical exposure. Like SIRS, a patient with MODS originating from systemic inflammation can benefit from a transfusion of oxygen reduced stored blood by having a reduced exposure to HETE acids and leukotriene B4, decreasing activation and recruitment of circulating neutrophils into the circulatory environment, and potentially decreasing the risk of long-term organ system damage.

Oxidative stress is associated with a wide range of disease states resulting from the reaction of oxygen and metal catalysts as described by the Fenton or Haber-Weiss reactions. One pervasive source of oxidative stress is the combination of oxygen and metals in our bodies, generally iron, that allow the generation of hydroxyl radical and superoxide followed by a series of oxidation products. To counteract the stress and damage caused by oxidation, the body has a series of controls in place. For example, the presence of reducing thiols such as cysteine or glutathione provides a reversible means to reduce oxidizing compounds. The oxidized forms of these thiols are reduced enzymatically to maintain a defense against oxidative damage. Under extreme stress or conditions of chronic oxidative stress the ability of the body to regenerate the thiols becomes compromised.

Thalassemia and sickle cell disease are chronic diseases during which the patients are exposed to oxidative damage due to the instability of the hemoglobin in their red blood cells. The degrading hemoglobin allows iron to react freely with oxygen generating the reactive species mentioned. Resulting degradation of the antioxidant pool is significant; for example, the glutathione levels in β-thalassemia patients has been documented to be only 35% of the level of normal subjects. See Kalpravidh, et al., "Glutathione Redox System in β-Thalassemia/Hb E Patients," The Scientific World Journal 2013, article ID 543973 (2013) (hereby incorporated by reference in its entirety). Chronic transfusion is the primary treatment for patients with sickle cell disease and thalassemia and as shown in the present disclosure, over the course of the cold-storage of red blood cells, the defense against oxidative stress is degraded. Oxidative stress is a major cause of vasculopathy which has been implicated in stroke, pulmonary hypotension and leg ulcers.

Methods of the present disclosure provide for, and include, for providing oxygen reduced stored blood to a patient having ischemic heart disease. Ischemic heart disease is characterized by a narrowing of the blood vessels that provide blood, oxygen, and nutrients to the heart muscle. As the disease progresses, the heart muscle can begin to die, leading to loss of cardiac function and, ultimately, a myocardial infarction. Surgical intervention to re-establish blood flow, either through angioplasty and stent deployment, or through a vascular bypass graft. In both cases, the return of blood flow to the site of injury can result ischemia/reperfusion (I/R) injury leading to new myocardial damage. Specifically, I/R injury can result in the exposure of cells to reactive oxygen species which can stimulate cellular autophagy. See Xia, Y. et al., "Activation of volume-sensitive Cl– channel mediates autophagy-related cell death in myocardial ischaemia/reperfusion injury," Oncotarget (2016) and Yousefi, B. et al., "The role of leukotrienes in immunopathogenesis of rheumatoid arthritis," Modern rheumatology/the Japan Rheumatism Association 24(2): 225-235 (2014) (hereby incorporated by reference in their entireties). Without being limited by theory, it is thought that red blood cells stored conventionally undergo oxidative damage during storage, which can pose a significant health risk to ischemic heart disease patients undergoing surgical interventions. Transfusion of red blood cells with oxidative damage can exacerbate the UR injury, leading to further damage to the heart tissue. Providing oxygen reduced stored blood provides superior anti-oxidative protection, as evidenced by increased NADPH reservoirs (see e.g., FIG. 5, FIG. 6, and FIG. 7), elevated levels of cysteine (see e.g., FIG. 13), elevated ratios of GSH to GSSG (see e.g., FIG. 12). As a result, these red blood cells have a decreased risk for inducing UR injury to patients with already weakened or deteriorated cardiac function.

Methods of the present disclosure provide for, and include, for providing oxygen reduced stored blood to a patient having diabetes. A patient with diabetes is at severe risk for long-term vascular complications as the result of prolonged hyperglycemia. Reactive oxygen species have been shown to be generated as the result of glucose autooxidation, polyol pathway activation, prostanoid synthesis, and protein glycation, leading to dysregulation of intracellular regulatory pathways that maintain vascular homeostasis. See Baynes et al., "Role of oxidative stress in diabetic complications: a new perspective on an old paradigm," Diabetes. 48(1):1-9 (1991) (hereby incorporated by reference in its entirety). If untreated, hyperglycemia can result in permanent damage and necrosis of tissue of the lower extremities, often necessitating amputation. Because of the link between oxidative stress and free radicals, the accumulation of oxidizing agents within conventionally stored blood can exacerbate the comorbidities associated with diabetes. Providing oxygen reduced stored blood cells provides superior anti-oxidative protection, as evidenced, for example, by increased NADPH reservoirs (see e.g., FIG. 5, FIG. 6, and FIG. 7), elevated levels of cysteine (see e.g., FIG. 13), elevated ratios of GSH to GSSG (see e.g., FIG. 12; see Yoshida, et al., "Enhancing Uniformity and Overall Quality of Red Cell Concentrate with Anaerobic Storage," Blood Transfusion, 15(2): 172-181 (2017); and Reisz 2016 (hereby incorporated by reference in their entireties)). As a result, these red cells will avoid introducing or aggravating oxidative injury in a patient with diabetes, and thereby reduce the risk of aggravating diabetic co-morbidities post-transfusion.

The present disclosure provides for, and includes, a method for reducing oxidative stress in a human patient in need of a blood transfusion comprising providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has an increased risk of oxidative stress.

Storage of oxygen reduced stored blood results in higher cysteine, GSH, NADH, NADPH and higher ratios of GSH/GSSG, NADPH/NADP, and NADH/NAD (See Table 1). These results show that oxygen reduced stored blood has a lower oxidation/reduction potential and thus provide a higher antioxidant capacity after transfusion. Thus oxygen reduced stored blood of the present disclosure provides superior defensive capability against oxidative damage. In the chronically transfused sickle cell disease or thalassemia patient replacing conventionally stored blood with oxygen reduced stored blood will avoid additional oxidative stress from the conventionally stored red blood cells and provide additional defense against oxidative damage.

The present disclosure provides for methods to reduce oxidative stress by providing a transfusion of oxygen reduced stored blood to a patient that further comprises reduced levels of inflammatory factors.

Methods of the present disclosure provide for, and include, identifying a patient at risk that will benefit from reducing oxidative stress when the patient requires a blood transfusion and providing the identified patient oxygen reduced stored blood that has an initial oxygen saturation of 20% or less prior to being stored for a storage period. As used herein, providing oxygen reduced stored blood includes whole blood and red blood cells as provided in the present disclosure.

Oxygen reduced stored blood that has an initial oxygen saturation of 20% or less prior to being stored for a storage period can be prepared with improved resistance to oxidative stress (see e.g., Table 1 and examples). As provided by the present disclosure, certain improvements are evident beginning at an initial saturation level of 20%. As used herein, improvements and benefits to the selected patients provided in the present disclosure are relative to (e.g., compared to) non-oxygen reduced stored blood stored for an identical storage period. Importantly, these differences become more pronounced as the storage period increases and as the initial oxygen saturation prior to storage is reduced.

In an aspect of the present disclosure, oxygen reduced stored blood suitable for reducing risks of oxidative stress includes oxygen reduced stored blood having one or more of reduced methemoglobin, reduced oxidation of beta-hemoglobin at residue H93, increased reservoir of reduced nicotinamide adenine dinucleotide phosphate (NADPH), increased GSH, increased ATP, increased DPG, increased NADPH reservoir, reduced PIP to PIP3 ratio, increased methylene THF, increased glutamate, increased ratio of GSH to glutathione disulfide (GSSG) (GSH/GSSG ratio), increased urate, or increased cysteine.

In an aspect of the present disclosure, oxygen reduced stored blood having an initial oxygen saturation of 20% or less and stored for at least 2 days has reduced methemoglobin. In an aspect, the oxygen reduced stored blood of the present disclosure is oxygen reduced stored blood having reduced oxidation of beta-hemoglobin at residue H93. See Wither 2016; and Reisz 2016, (hereby incorporated by reference in their entireties). In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased of GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased of methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 20% or less and stored for at least 2 days has reduced methemoglobin, reduced oxidation of beta-hemoglobin at residue H93, increased reservoir of reduced nicotinamide adenine dinucleotide phosphate+hydrogen (NADPH), increased GSH, increased ATP, increased DPG, increased NADPH reservoir, reduced PIP to PIP3 ratio, increased methylene THF, increased glutamate, increased ratio of GSH to glutathione disulfide (GSSG) (GSH/GSSG ratio), increased urate, and increased cysteine.

In an aspect of the present disclosure, oxygen reduced stored blood having an initial oxygen saturation of 10% or less and stored for at least 2 days has reduced methemoglobin. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having increased reservoir of reduced nicotinamide adenine dinucleotide phosphate+hydrogen (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 5% or less and stored for at least 2 days has reduced methemoglobin. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having reduced dioxidation of Cys152 in Glyceraldehyde-3-Phosphate Dehydrogenase. In an aspect, the oxygen reduced stored blood of the present disclosure is oxygen reduced stored blood having increased reservoir of reduced nicotinamide adenine dinucleotide phosphate+hydrogen (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 3% or less and stored for at least 2 days has reduced methemoglobin. In an aspect, the oxygen reduced stored blood of the present disclosure is oxygen reduced stored blood having reduced dioxidation of Cys152 in Glyceraldehyde-3-Phosphate Dehydrogenase. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIPS ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

Methods of the present disclosure provide for, and include, identifying a patient at risk that will benefit from reducing oxidative stress when the patient requires a blood transfusion and providing the identified patient oxygen reduced stored blood that has an initial oxygen saturation of 20% or less prior to being stored for a storage period. Methods also provide for providing oxygen reduced stored blood that has an initial oxygen saturation of 20% or less prior to being stored for a storage period for transfusion to a patient at risk of oxidative stress when the patient requires a blood transfusion. Also included are methods comprising transfusing oxygen reduced stored blood that has an initial oxygen saturation of 20% or less prior to being stored for a storage period to a patient at risk of oxidative stress. As discussed, as the storage period is increased, the improvements and benefits to the patients having an increased risk of oxidative damage increase relative to blood stored using conventional methods. Accordingly methods providing oxygen reduced stored blood having an initial oxygen saturation of 20% or less include providing oxygen reduced stored blood having an initial oxygen saturation of 10% or less. Methods of providing oxygen reduced stored blood having an initial oxygen saturation of 20% or less further include providing oxygen reduced stored blood having an initial oxygen saturation of 5% or less. Methods of providing oxygen reduced stored blood having an initial oxygen saturation of 20% or less further include providing oxygen reduced stored blood having an initial oxygen saturation of 3% or less.

As provided by the present disclosure, a patient in need of a blood transfusion having an increased risk of oxidative stress includes a trauma patient requiring four or more units of blood, a trauma patient requiring ten or more units of blood, a patient having sickle cell disease, a patient having thalassemia, and combinations thereof. In an aspect, the methods provide for providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has sickle cell anemia. In an aspect, the methods provide for providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has thalassemia. In an aspect, the thalassemia is α-thalassemia. In another aspect, the thalassemia is β-thalassemia. The disclosure further provides for a method of reducing the risk of oxidative stress to a trauma patient requiring four or more units of blood. In a further aspect, the patient in need of reduced risk of oxidative stress is a trauma patient requiring ten or more units of blood.

Also included and provided by the present disclosure, are methods to reduce oxidative stress in sickle cell and thalassemia patients requiring multiple transfusions. In an aspect, a sickle cell patient is provided a unit of oxygen reduced stored blood having an initial oxygen saturation of 20% or less prior to storage and an additional unit of oxygen reduced stored blood when the hemoglobin concentration below 5 g/dL. In another aspect, a sickle cell patient is provided with an additional unit of oxygen reduced stored blood when the peak, centerline flow velocity of the middle cerebral artery is greater than 200 cm/sec as determined by transcranial Doppler ultrasound (TCD). In a further aspect, an additional unit of blood is provided to a sickle cell patient when sickle hemoglobin levels rise above 30%. In yet further aspects, the sickle cell patient receives periodic transfusions of oxygen reduced stored blood to maintain the level of sickle hemoglobin below 30% of total hemoglobin. In an aspect, a sickle cell patient in need of reduce oxygen stress receives a transfusion about every thirty days. As use herein, about every thirty days means between 25 and 35 days.

The present disclosure provides for, and includes, providing oxygen reduced stored blood to a sickle cell patient having an acute attack to reduce the symptoms and provides for reduced oxidative stress. In an aspect, the sickle cell patient is experiencing a vaso-occlusive crisis.

The present disclosure provides for, and includes, providing oxygen reduced stored blood to a sickle cell patient in need of surgery. In an aspect the sickle cell patient receives one or more pre-operative transfusions to reduce perioperative hypoxia, hypoperfusion or acidosis. In an aspect, the sickle cell patient receives two or more pre-operative transfusions. In another aspect, the sickle cell patient receives three or more pre-operative transfusions. In certain aspect, the sickle cell patient receives four or more pre-operative transfusions.

Due to the effects of anesthesia during surgery, people with sickle cell disease are at an increased risk for developing vaso-occlusive crises resulting from reduced blood flow (hypoperfusion), acidosis, and hypoxia resulting from decreased respiratory rate. To mitigate these complications, people with sickle cell disease can receive peri-operative transfusions of red blood cells. However, conventionally stored red blood cells have measurable levels of inflammatory biomolecules and cytokines, which have been shown to promote vasculopathy and vaso-occlusion. As a result, peri-operative transfusion of conventional red cells can result in an increased risk for pain crises and organ or tissue damage. Oxygen reduced stored blood has reduced levels of HETE acids and leukotriene B4 (FIG. 2 and FIG. 4) relative to conventionally stored blood. Transfusion of oxygen reduced stored blood can reduce the risk of developing transfusion-related vaso-occlusive events during or after surgery.

Figure 8:
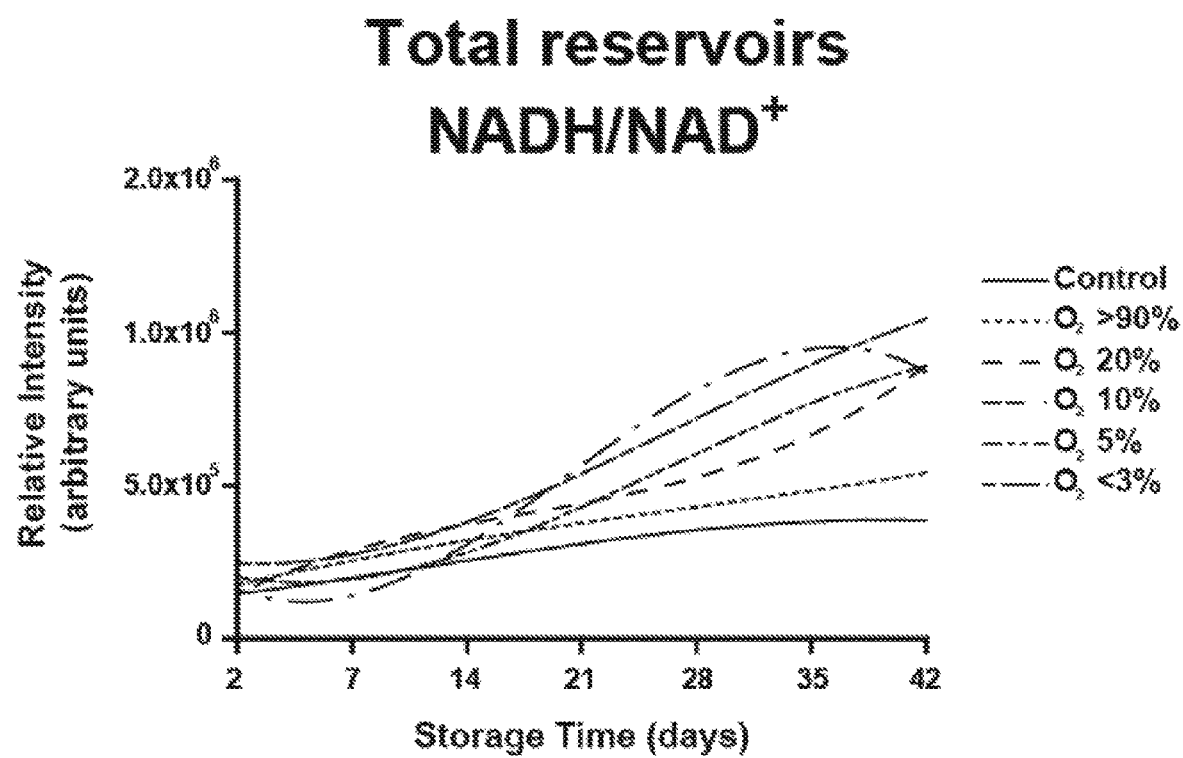

Additionally, it has been shown that conventional blood when transfused into the sickle cell circulatory environment is at risk for rapid removal through eryptosis, leading to the severe complication of delayed hemolytic transfusion reaction (DHTR). For patients recovering from surgery, the rapid drop in hematocrit associated with DHTR can cause severe, even life-threatening, complications. Oxygen reduced stored blood has decreased risk for DHTR via more stable membranes (FIG. 18), and higher intracellular ATP (FIG. 15 and FIG. 8). Use of oxygen reduced blood in peri-operative transfusion for patients with sickle cell disease decreases the risk for DHTR-related complications and improves overall patient outcomes and recovery times.

The present disclosure provides for, and includes, a method for reducing the risk of an adverse event in a hemoglobinopathy patient in need of a blood transfusion comprising providing oxygen reduced stored blood for transfusion into a hemoglobinopathy patient in need of a blood transfusion, wherein oxygen reduced stored blood has an initial oxygen saturation of 20% or less prior to being stored for a storage period wherein said patient has an increased risk of an adverse event. In an aspect, the methods of the present disclosure provide for a reduction in delayed hemolytic transfusion reactions following transfusion to treat sickle cell disease or thalassemia by providing blood having a higher phosphatidylinositol 4-phosphate to phosphatidylinositol (3,4,5)-triphosphate ratio. In another aspect, the methods of the present disclosure provide for an improved red blood cell membrane wherein the membrane after storage is more physiological membrane.

In an aspect, the hemoglobinopathy patient in need of blood transfusion is a sickle cell patient. In an aspect, methods of the present disclosure provide for reducing delayed hemolytic transfusion reactions following transfusion to treat sickle cell disease or thalassemia by providing blood having a higher phosphatidylinositol 4-phosphate to phosphatidylinositol (3,4,5)-triphosphate ratio. In an aspect, the present disclosure provides for, and includes, a method for reducing delayed hemolytic transfusion reactions following transfusion to treat sickle cell disease or thalassemia by providing blood which maintains a more physiologic membrane over the course of cold storage. As used herein, a more physiological membrane refers to a membrane having one or more of the following characteristics:

a membrane that has decreased activity of Ca' ion channels along the cell membrane;
prevention of membrane hyperpolarization as indicated by a loss of chloride ions through channels activated by oxidative stress;
reduced calcium ion influx through calcium channels activated by membrane and cytoskeletal oxidation; and
a membrane that maintains asymmetrical distribution of phosphatidylserine along the cytosolic surface of the cell membrane.

Oxygen reduced stored blood provides for a more physiological membrane through a variety of mechanisms. For example, decreased activity of $Ca^{2+}$ ion channels is indicated by the high PIP:PIP3 ratio, and lower intracellular $Ca^{2+}$ can be measured directly with fluorescent probe such as Fura-2 (Thermo-Fisher Scientific) using flow cytometer. See Mahmud et al., "Suicidal erythrocyte death, eryptosis, as a novel mechanism in heart failure-associated anaemia," Cardiovasc Res 98(1):37-46 (2013) (hereby incorporated by reference in its entirety). As provided in the present disclosure, oxygen reduced stored blood can provide low oxidative stress as evidenced by high NADPH, NADP, and GSH ratios resulting in reduced membrane hyperpolarization. Oxygen reduced stored blood further provides reduced dehydration and retained deformability by providing reduced calcium ion flux, where oxidation results in activation of calcium ion channels. Cell membrane scrambling is promoted by activation of JAK3 kinase, which is phosphorylated as the result of energy depletion (ATP loss) within the cell. Oxygen reduced stored blood retains high ATP production as evidenced by stimulation of the PPP and EMP pathways. Membrane scrambling can be characterized by phosphatidylserine expression that can be measured through labeling cell membrane with fluorescent annexin-V and quantifying with flow cytometry or microscopy. See Yoshida et al., 2008, supra. JAK3 kinase activity can be measured through Western Blot analysis, Luminex technology, and other methods well known in the art. See Chang et al., "Mammalian MAP kinase signaling cascades," Nature 410 (6824):37-40 (2001) (hereby incorporated by reference in its entirety).

Methods of the present disclosure provide for, and include, a method for reducing delayed hemolytic transfusion reactions following transfusion to treat sickle cell disease or thalassemia wherein the oxygen reduced stored blood comprises fewer pre-eryptotic biomarkers. As used herein, pre-eryptotic biomarkers refers the following characteristics:

a membrane that has decreased activity of Ca' ion channels along the cell membrane (evidenced by high PIP:PIP3 ratio, and can be measured directly with fluorescent ionaphores);
a membrane that is not hyperpolarized as defined by loss of chloride ions through channels activated by oxidative stress (oxygen reduced stored blood has low oxidative stress as evidenced by high NADPH, NADP, and GSH ratios); and
a membrane that maintains asymmetrical distribution of phosphatidylserine along the cytosolic surface of the cell membrane; cells that do not have increased intracellular calcium ($Ca^{2+}$) ion concentrations; cells that do not elevated levels of phosphorylated JAK3 kinase; cells that do not have activated caspases such as caspase-3 (measured by methods known in the art); and cells that maintain activity of AMP-activated kinase (AMPKα1) and cGMp-dependent protein kinase type I (cGKI) (as determined using standard methods known to a person skill in the art.

Transfusion of red blood cells is one of the primary treatments people with sickle cell disease and thalassemia. However, high oxidative environment characteristic to these hematological diseases triggers rapid influx of calcium ions into the RBC, resulting in alterations to the cell membrane, leading to redistribution of cytosolic biomarkers to the extracellular leaflet of plasma membrane. Ultimately, the calcium dependent reorganization of the cell membrane leads to rapid clearance of the circulating red blood cell through eryptosis. See Lang et al., "Triggers, Inhibitors, Mechanisms, and Significance of Eryptosis: The Suicidal Erythrocyte Death," BioMed Research International, vol. 2015, Article ID 513518, 16 pages, 2015; Lang et al., "Killing me softly—suicidal erythrocyte death," Int J Biochem Cell Biol. 44(8):1236-43 (2012); Lang et al., "Oxidative Stress and Suicidal Erythrocyte Death," Antioxidants Amp Redox Signal. 21(1):138-153 (2014); and Gatidis et al., "Hemin-induced suicidal erythrocyte death," Ann Hematol. 88(8):721-726 (2009) (hereby incorporated by reference in their entireties). In addition, repeated transfusions of red blood cells carries significant risk for the patient developing delayed hemolytic transfusion reaction, characterized by rapid and extreme anemia within 2-5 days following transfusion. DHTR can be triggered due to induction of eryptosis in the donated cells as a result of a loss of intracellular energy (ATP) inducing kinase signaling pathways (JAK3 activation, AMPKα1 and cGKI inhibition). See Lang et al., "Killing me softly—suicidal erythrocyte death," Int J Biochem Cell Biol 44(8):1236-43 (2012) (hereby incorporated by reference in its entirety).

Without being limited to a particular theory, storage of oxygen reduced blood has been shown to increase cellular concentration of phosphatidylinositol 4-phosphate (PIP), and prevents the formation of phosphatidylinositol (3,4,5)-triphosphate (PIP3). As a result, calcium channels along the red cell membrane remain inactive, thereby preventing or reducing the influx of calcium into the cytosol. Additionally, reduction of oxygen in oxygen reduced stored blood also activates the Lands cycle for maintaining asymmetrical distribution of biomarkers between the extracellular and cytosolic leaflets of the cell membrane. Use of oxygen reduced stored blood in transfusion therapy for sickle cell disease would preserve the native configuration of the red blood cell membrane, thereby preventing the extracellular expression of pro-eryptotic biomarkers, and thus allowing transfused RBCs to survive the sickle cell circulatory environment. Ultimately, this can lead to the ability for clinicians to reduce the therapeutic dose per transfusion and/or decrease the frequency at which the patient requires medical intervention. Storage of oxygen reduced red blood cells has been shown to establish a higher energetic state of the red blood cell during storage. Reduction of oxygen, and subsequent maintenance of low oxygen during storage, promotes higher EMP flux, larger de novo synthesis of ATP via the pentose phosphate pathway, and preservation of GAPDH enzymes thereby maintaining homeostatic metabolism regulation. Ultimately, generation and use of oxygen reduced stored blood for therapeutic transfusions in sickle cell disease and thalassemia mitigates the development of DHTR, allowing for a safer, more effective treatment.

Sickle cell disease is a genetic mutation that primarily afflicts people of Sub-Saharan African, Middle Eastern, and South-East Asian descent. Transfusion of red blood cells is one of the primary treatments for both acute and chronic vaso-occlusive symptoms in people with sickle cell disease (SCD). However, due to the frequency and total volume of RBCs required for therapeutic transfusion per recipient (-15-20 units per visit), recipients of therapeutic blood transfusions often develop alloimmunization against the donated blood cells leading to reduction in efficacy of the treatment or severe, systemic complications. As a result, for blood intended for SCD transfusion more extensive antigen type matching is required compared to traditional clinical arenas requiring blood transfusion. As a result, the most compatible donors are generally from the same ethic background as the patient; unfortunately, the same ethnic groups that are highly compatible donors also have the highest frequency of deficiency of glucose-6-phosphate hydrogenase (G6PD), which has been correlated to a relatively poor storage, resulting in the need to discard the blood before it can be used for therapies. See Cappellini et al., "Glucose-6-phosphate dehydrogenase deficiency," Lancet 371(9606): 64-74 (2008) and Francis et al., "Glucose-6-phosphate dehydrogenase deficiency in transfusion medicine: the unknown risks," *Vox Sang* 105(4):271-82 (2013); and Tzounakas, et al., "Glucose 6-phosphate dehydrogenase deficient subjects may be better 'storers' than donors of red blood cells," *Free Radic Biol Med,* 96: 152-165 (2016).

(hereby incorporated by reference in their entireties). Unfortunately, there is no established protocol for testing for G6PD activity as part of the donor eligibility screening.

G6PD activity is essential for maintaining the energetic molecules, such as NADPH, that fuel the native antioxidative pathways (i.e. glutathione mediated reduction of hydrogen peroxide) essential for maintaining bioactivity of the hemoglobin molecules in the red blood cell; loss or reduction of activity in this enzyme leads to premature hemolysis in storage and poor retention of the cells post-transfusion. However, oxygen reduced stored blood has results in an intracellular reservoir of NADPH, as well as increased concentrations of the reduced form of glutathione (GSH). Furthermore, oxygen reduced stored blood has increased methylenetetrahydrofolate, which can promote overall NADPH production. Low oxygen storage of blood can allow for better survivability, and therefore usability, of blood from G6PD-deficient donors. This will increase the blood supply available for people with sickle cell disease receiving therapeutic transfusions, especially in rural areas where the blood supplies are more limited.

In an aspect of the present disclosure, oxygen reduced stored blood suitable for reducing risks of hemoglobinopathy includes oxygen reduced stored blood having reduced methemoglobin, reduced oxidation of beta-hemoglobin at residue H93, increased reservoir of reduced nicotinamide adenine dinucleotide phosphate (NADPH), increased GSH, increased ATP, increased DPG, increased NADPH reservoir, reduced PIP to PIP3 ratio, increased methylene THF, increased glutamate, increased ratio of GSH to glutathione disulfide (GSSG) (GSH/GSSG ratio), increased urate, and increased cysteine.

A patient with α- or β-thalassemia major is unable to produce functional hemoglobin molecules, resulting in severe anemia and necessitating transfusion of red blood cells (RBCs). A result of requiring regular (i.e. chronic) transfusions, people with thalassemia can suffer from delayed hemolytic transfusion reaction (DHTR) which is characterized by a rapid decrease in hematocrit following therapeutic transfusion. Not to be limited by theory, DHTR can be initiated as a response to sudden eryptosis, leading to rapid removal of the circulating red cells by macrophages and monocytes.

Without being limited by theory, one of the major triggers for eryptosis is accrued oxidative damage, a known consequence of conventional red blood cell storage. See Bhaysar et al., "Janus Kinase 3 is Expressed in Erythrocytes, Phosphorylated Upon Energy Depletion and Involved in the Regulation of Suicidal Erythrocyte Death," *Cellular Physiology and Biochemistry* 27(5):547-556 (2011) (hereby incorporated by reference in its entirety). Oxygen reduced stored blood has superior anti-oxidative protection, as evidenced by increased NADPH reservoirs (see e.g., FIG. 5, FIG. 6, and FIG. 7), elevated levels of cysteine (see e.g., FIG. 13), elevated ratios of GSH to GSSG (see e.g., FIG. 12).

Furthermore, eryptosis is also promoted when red cells no longer have sufficient levels of ATP, which also occurs during conventional storage. Gürer et al., "Arachidonic acid metabolites and colchicine in Behçet's disease (BD)" Prostaglandins, leukotrienes, and essential fatty acids 43(4): 257-9 (1999) (hereby incorporated by reference in its entirety). However, oxygen reduced blood has improved overall ATP levels (see e.g., FIG. 16), and improved metabolic activity by sustaining glycolysis through the pentose phosphate pathway (see e.g., FIG. 15).

Use of anaerobic blood products for chronic therapeutic transfusions for people with α- or β-thalassemia will have a decreased risk of developing DHTR due to the increased protection from oxidative damage, and superior preservation of intracellular energy (ATP), as well as the potential benefit of decreasing the frequency at which transfusions are required.

In an aspect of the present disclosure, oxygen reduced stored blood having an initial oxygen saturation of 20% or less and stored for at least 2 days has reduced methemoglobin. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased of GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased of methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 20% or less and [00106], and stored for at least 2 days has reduced methemoglobin, reduced oxidation of beta-hemoglobin at residue H93, increased reservoir of reduced nicotinamide adenine dinucleotide phosphate (NADPH), increased GSH, increased ATP, increased DPG, increased NADPH reservoir, reduced PIP to PIP3 ratio, increased methylene THF, increased glutamate, increased ratio of GSH to glutathione disulfide (GSSG) (GSH/GSSG ratio), increased urate, and increased cysteine.

In an aspect of the present disclosure, oxygen reduced stored blood having an initial oxygen saturation of 10% or less and [00106], and stored for at least 2 days has reduced methemoglobin. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 5% or less and stored for at least 2 days has reduced methemoglobin. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having reduced dioxidation of Cys152 in Glyceraldehyde-3-Phosphate Dehydrogenase. In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

In an aspect of the present disclosure, oxygen reduced stored blood having an initial oxygen saturation of 3% or less and stored for at least 2 days has reduced methemoglobin. In an aspect, the oxygen reduced stored blood of the present disclosure is oxygen reduced stored blood having reduced dioxidation of Cys152 in Glyceraldehyde-3-Phosphate Dehydrogenase. In an aspect, the oxygen reduced stored blood of the present disclosure is oxygen reduced stored blood having reduced oxidation of beta-hemoglobin at residue H93. In an aspect, the oxygen reduced stored blood of the present disclosure is oxygen reduced stored blood having increased reservoir of reduced nicotinamide adenine dinucleotide phosphate (NADPH). In an aspect, the oxygen reduced stored blood of the present disclosure is oxygen reduced stored blood having increased GSH. In an aspect, the oxygen reduced stored blood of the present disclosure is oxygen reduced stored blood having increased ATP. In an aspect, the oxygen reduced stored blood of the present disclosure is oxygen reduced stored blood having increased ATP and DPG. In a further aspect, oxygen reduced stored blood of the present disclosure further includes increased NADPH reservoir, and increased GSH, ATP, and DPG. In an aspect, the oxygen reduced stored blood of the present disclosure is oxygen reduced stored blood having reduced PIP to PIP3 ratio. In an aspect, the oxygen reduced stored blood of the present disclosure is oxygen reduced stored blood having increased methylene THF. In an aspect, the oxygen reduced stored blood of the present disclosure is oxygen reduced stored blood having increased glutamate. In an aspect, the oxygen reduced stored blood of the present disclosure is oxygen reduced stored blood having increased ratio of GSH to glutathione disulfide (GSSG) (GSH/GSSG ratio). In an aspect, the oxygen reduced stored blood of the present disclosure is oxygen reduced stored blood having increased urate. In an aspect, the oxygen reduced stored blood of the present disclosure is oxygen reduced stored blood having increased cysteine.

Ischemia reperfusion injury occurs when the blood supply is interrupted then re-established and is a significant cause of mortality and morbidity. Surgeries involving interruption of the blood supply, for example cardiac surgery, kidney transplant, liver resection or colectomy all put the patient at risk of ischemia reperfusion injury. Improved methods for providing blood for transfusion during bypass or p surgery is desirable. Here, we provide a method of reducing risks and damage to patients by providing oxygen reduced stored blood that has lower levels of inflammatory factors than found in conventionally stored blood. Accordingly, in addition to the improved ATP, 2,3-DPG, and improved deformability, oxygen reduced stored blood of the present specification provides an unexpected benefit of decreasing the risk of damage, or damage to, tissues during reperfusion.

Not to be limited by theory, it is thought that during ischemia changes in cellular metabolism, ion concentration, and membrane composition make the cells susceptible to damage by reactive oxygen species that are generated in high quantities in response to a sudden restoration of oxygen with the renewed blood flow. See Pell et al., "Moving Forwards by Blocking Back-Flow: The Yin and Yang of MI Therapy," Circ Res 118(5):898-906 (2016) and Hausenloy et al., "Myocardial ischemia-reperfusion injury: a neglected therapeutic target," J Clin Invest 123(1):92-100 (2013) (hereby incorporated by reference in their entireties). Ultimately, the oxidative damage results in cellular death and organ dysfunction as a direct result of re-establishment of oxygenated blood flow. It is further thought that in addition to oxidative damage, reperfusion initiates an inflammatory response that, among other effects, can result in hypercoagulability and further cell damage.

A patient experiencing ischemia/reperfusion injury can present the following clinical manifestations and combinations thereof Lack of blood flow (termed 'no reflow') through the vessel once the obstruction has been removed, such as the release of a hemostat during surgery;

Myocardial stunning which is a transient inability for the heart muscle to effectively contract and restore normal cardiac output (in cardiac surgery patients);

Development of tachycardia, ventricular fibrillation, or accelerated idioventricular rhythm following restoration of blood flow to the heart muscle (in cardiac surgery patients); and Impaired gut motility, nutrient absorption, increased intestinal permeability, and bacterial infection of the portal and systemic circulation (for gastrointestinal surgery patients); and A common consequence of ischemia reperfusion injury is the development of multiple organ dysfunction syndrome (MODS), and other remote organ injury; the most common system is the pulmonary system leading to respiratory failure, followed by hepatic, renal, GI, myocardial, and CNS dysfunction.

Figure 3:
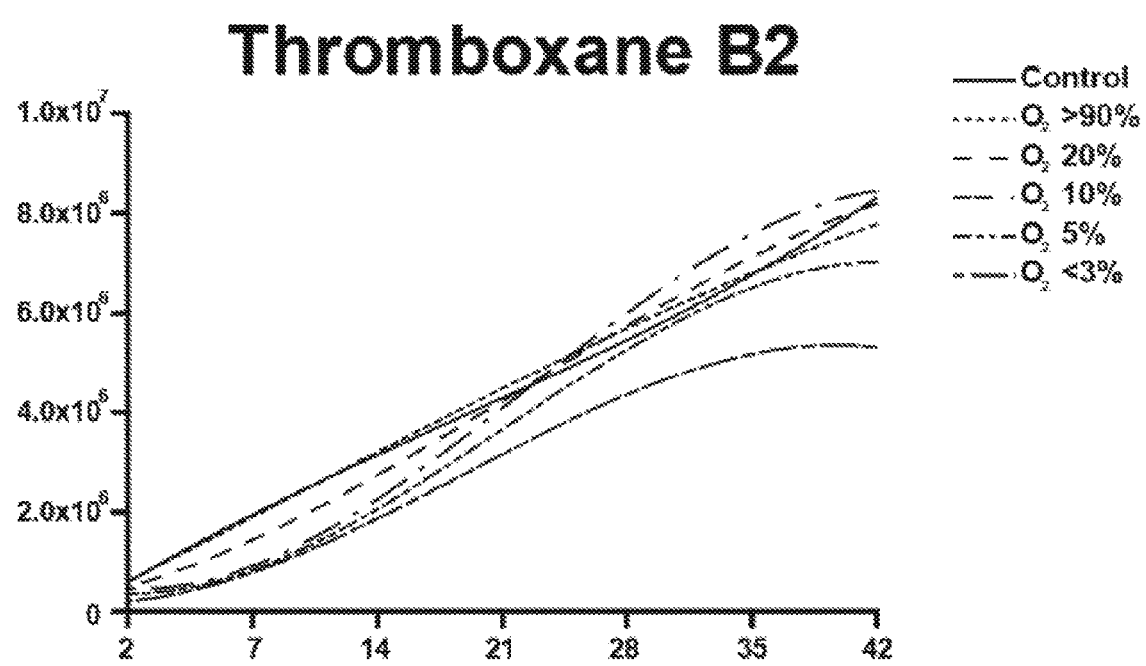

Conventionally stored blood, even after as little as two days has increased levels of Thromboxane B2 when compared to oxygen reduced stored blood (See e.g., FIG. 3). Beginning at seven days, blood having high levels of oxygen begin to express increasing levels of Leukotriene B4. (see e.g., FIG. 2). Extracellular levels of hydroxyeicosatetraenoic acid (HETE) begin to rise in stored blood earlier than oxygen reduced stored blood and increase at a higher rate and to higher levels. Cellular HETE levels are increased as early as two days relative to HETE levels in oxygen reduced stored blood. During further storage, cellular HETE levels remain higher and increase relative to oxygen reduced stored blood. As shown in U.S. Provisional Application No. 62/163,269, oxygen reduced stored blood has reduced levels of BRMs RANTES, Eotaxin 1, cell free hemoglobin, and isoprostane. Oxygen reduced stored blood has generally reduced levels of inflammatory factors when compared to conventionally stored blood. Accordingly, conventionally stored blood containing pro-inflammatory compounds can be a significant risk for mortality and adverse events.

In addition to the changes in levels of pro-inflammatory compounds in early stages of blood storage, conventionally stored red blood cells increasingly lose the ability to defend against oxidative damage as compared to oxygen reduced stored blood. In view of the previously unappreciated changes in blood during storage, transfusion of conventionally stored blood during reperfusion after an ischemic event can contribute to oxidative stress due to reduced levels of cysteine, GSH, NADH, NADPH levels. In contrast, oxygen reduced stored blood maintain higher levels of cysteine, GSH, NADH, NADPH and oxygen reduced stored blood is expected to help protect against oxidative damage.

In an aspect of the present disclosure, a human patient in need of a blood transfusion is a patient in need of a massive transfusion, recurrent transfusions or chronic transfusions.

In an aspect of the present disclosure, a human patient in need of a blood transfusion has sickle cell disease with a hemoglobin concentration below 5 g/dL. In another aspect, a human patient in need of a blood transfusion has sickle cell disease and the peak, centerline flow velocity of the middle cerebral artery is greater than 200 cm/sec as determined by transcranial Doppler ultrasound (TCD). In another aspect, a human patient in need of a blood transfusion has sickle cell disease and receives transfusions to reduce sickle hemoglobin levels to below 30% of total hemoglobin in the body. In another aspect, a human patient in need of a blood transfusion has sickle cell disease and is experiencing acute chest syndrome. In another aspect, a human patient in need of a blood transfusion has sickle cell disease and is experiencing a vaso-occlusive crisis. In a further aspect, a human patient in need of a blood transfusion has sickle cell disease and is in need of surgery, wherein said patient receives one or more pre-operative transfusions to reduce perioperative hypoxia, hypoperfusion, and acidosis.

In an aspect of the present disclosure, a human patient in need of a blood transfusion has thalassemia with a hemoglobin concentration below 5 g/dL.

In another aspect, a human patient in need of a blood transfusion is a surgery patient. In another aspect, a human patient in need of a blood transfusion has systemic inflammatory response syndrome (SIRS). In another aspect, a human patient in need of a blood transfusion has chronic vascular inflammation. In a further aspect, a human patient in need of a blood transfusion has diabetes. In a further aspect, a human patient in need of a blood transfusion having chronic vascular inflammation has diabetes.

In an aspect of the present disclosure, a human patient in need of a blood transfusion has inflammation, endotheliopathy, adhesion to endothelial cell wall, hypercoagulability, vasoconstriction, complement system activation, impaired perfusion, infection, or immunomodulation.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells, and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 4° C. and 6° C.

As used herein, "blood product" includes separated platelets, plasma, or white blood cells.

As used herein, "whole blood" includes white blood cells (WBCs), platelets suspended in plasma, and includes electrolytes, hormones, vitamins, antibodies, etc. In whole blood, white blood cells are normally present in the range of between 4.5 and $11.0 \times 10^9$ cells/L, and the normal RBC range at sea level is $4.6$-$6.2 \times 10^{12}$/L for men and $4.2$-$5.4 \times 10^{12}$/L for women. The normal hematocrit, or percent packed cell volume, is about 40-54% for men and about 38-47% for women. The platelet count is normally 150-$450 \times 10^9$/L for both men and women. Whole blood is collected from a blood donor, and is usually combined with an anticoagulant. Whole blood, when collected is initially at about 37° C. and rapidly cools to about 30° C. during and shortly after collection, but slowly cools to ambient temperature over about 6 hours. Whole blood can be processed according to methods of the present disclosure at collection, beginning at 30-37° C., or at room temperature (typically about 25° C.).

As used herein, "red blood cells" (RBCs), "stored red blood cells", "oxygen reduced stored red blood cells", and "oxygen and carbon dioxide reduced stored red blood cells", include RBCs present in whole blood, leukoreduced RBCs, platelet reduced RBCs, leukocyte and platelet reduced RBCs, and packed red blood cells (pRBCs). Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%. As used herein, oxygen reduced stored RBCs can include oxygen and carbon dioxide reduced stored RBCs.

As used herein, "stored blood" includes oxygen reduced or oxygen and carbon dioxide reduced blood stored from 1 to 6° C. In an aspect, stored blood includes stored red blood cells. As used herein, "stored red blood cells" includes oxygen reduced or oxygen and carbon dioxide reduced red blood cells stored from 1 to 6° C. In an aspect, stored red blood cells include red blood cells (RBC) present in whole blood. In another aspect, stored red blood cells include RBC present in leukoreduced whole blood. In another aspect, stored red blood cells include red blood cells (RBC) present in leukoreduced RBC. In a further aspect, stored red blood cells include red blood cells (RBC) present in platelet reduced RBC. In yet another aspect, stored red blood cells include red blood cells (RBC) present in leukoreduced and platelet reduced RBC.

In an aspect of the present disclosure, oxygen reduced stored red blood cells can be stored for a period of at least 2 days. In another aspect, oxygen reduced stored red blood cells can be stored for a period of at least 7 days. In another aspect, oxygen reduced stored red blood cells can be stored for a period of at least 14 days. In another aspect, oxygen reduced stored red blood cells can be stored for a period of at least 21 days. In another aspect, oxygen reduced stored red blood cells can be stored for a period of at least 28 days. In another aspect, oxygen reduced stored red blood cells can be stored for a period of up to 42 days.

As used herein, a "unit" of blood is about 450-500 ml including anticoagulant. Suitable anticoagulants include CPD, CPDA1, ACD, and ACD-A.

Suitable blood for use in this method comprises oxygen reduced stored blood having an anticoagulant. In an aspect of the present disclosure, oxygen reduced red blood cells is stored for up to 6 weeks to produce oxygen reduced stored blood. In another aspect, oxygen reduced stored blood usually further comprise an additive solution. Suitable additive solutions according to the present disclosure include AS-1, AS-3 (Nutricel®), AS-5, SAGM, PAGG-SM, PAGG- GM, MAP, AS-7, ESOL-5, EAS61, OFAS1, OFAS3, and combinations thereof. In an aspect, the additive solution is added at the time of component separation. In an aspect, the additive solution is AS-1. In another aspect, the additive solution is AS-3. In other aspects, the additive solution is SAGM.

In an aspect of the present disclosure, oxygen reduced stored blood and oxygen and carbon dioxide reduced stored blood have an initial oxygen saturation of 40% or less. In another aspect, oxygen reduced stored blood have an initial oxygen saturation of 20% or less. In another aspect, oxygen reduced stored blood have an initial oxygen saturation of 10% or less. In another aspect, oxygen reduced stored blood have an initial oxygen saturation of 5% or less. In another aspect, oxygen reduced stored blood have an initial oxygen saturation of 3% or less.

In an aspect of the present disclosure, oxygen reduced stored blood has an initial oxygen saturation of 40% or less and is stored for at least 2 days. In an aspect, oxygen reduced stored blood has an initial oxygen saturation of 40% or less is stored for at least 4 days. In another aspect, oxygen reduced stored blood has an initial oxygen saturation of 20% or less is stored for at least 7 days. In another aspect, oxygen reduced stored blood has an initial oxygen saturation of 40% or less is stored for at least 14 days. In another aspect, oxygen reduced stored blood has an initial oxygen saturation of 40% or less is stored for at least 21 days. In another aspect, oxygen reduced stored blood has an initial oxygen saturation of 40% or less is stored for at least 28 days. In another aspect, oxygen reduced stored blood has an initial oxygen saturation of 40% or less is stored for at least 35 days. In another aspect, oxygen reduced stored blood has an initial oxygen saturation of 40% or less is stored for 42 days.

In an aspect of the present disclosure, oxygen reduced stored blood has an initial oxygen saturation of 20% or less and is stored for at least 2 days. In an aspect, oxygen reduced stored blood has an initial oxygen saturation of 20% or less is stored for at least 4 days. In another aspect, oxygen reduced stored blood has an initial oxygen saturation of 20% or less is stored for at least 7 days. In another aspect, oxygen reduced stored blood has an initial oxygen saturation of 20% or less is stored for at least 14 days. In another aspect, oxygen reduced stored blood has an initial oxygen saturation of 20% or less is stored for at least 21 days. In another aspect, oxygen reduced stored blood has an initial oxygen saturation of 20% or less is stored for at least 28 days. In another aspect, oxygen reduced stored blood has an initial oxygen saturation of 20% or less is stored for at least 35 days. In another aspect, oxygen reduced stored blood has an initial oxygen saturation of 20% or less is stored for 42 days.

In an aspect of the present disclosure, oxygen reduced stored blood has an initial oxygen saturation of 10% or less is stored for at least 2 days. In an aspect, oxygen reduced stored blood has an initial oxygen saturation of 10% or less is stored for at least 4 days. In another aspect, oxygen reduced stored blood has an initial oxygen saturation of 10% or less is stored for at least 7 days. In another aspect, oxygen reduced stored blood has an initial oxygen saturation of 10% or less is stored for at least 14 days. In another aspect, oxygen reduced stored blood has an initial oxygen saturation of 10% or less is stored for at least 21 days. In another aspect, oxygen reduced stored blood has an initial oxygen saturation of 10% or less is stored for at least 28 days. In another aspect, oxygen reduced stored blood has an initial oxygen saturation of 10% or less is stored for at least 35 days. In another aspect, oxygen reduced stored blood has an initial oxygen saturation of 20% or less is stored for 42 days.

In an aspect of the present disclosure, oxygen reduced stored blood has an initial oxygen saturation of 5% or less is stored for at least 2 days. In an aspect, oxygen reduced stored blood has an initial oxygen saturation of 5% or less is stored for at least 4 days. In another aspect, oxygen reduced stored blood has an initial oxygen saturation of 5% or less is stored for at least 7 days. In another aspect, oxygen reduced stored blood has an initial oxygen saturation of 5% or less is stored for at least 14 days. In another aspect, oxygen reduced stored blood has an initial oxygen saturation of 5% or less is stored for at least 21 days. In another aspect, oxygen reduced stored blood has an initial oxygen saturation of 5% or less is stored for at least 28 days. In another aspect, oxygen reduced stored blood has an initial oxygen saturation of 5% or less is stored for at least 35 days. In another aspect, oxygen reduced stored blood has an initial oxygen saturation of 5% or less is stored for 42 days.

In an aspect of the present disclosure, oxygen reduced stored blood has an initial oxygen saturation of 3% or less is stored for at least 2 days. In an aspect, oxygen reduced stored blood has an initial oxygen saturation of 20% or less is stored for at least 4 days. In another aspect, oxygen reduced stored blood has an initial oxygen saturation of 3% or less is stored for at least 7 days. In another aspect, oxygen reduced stored blood has an initial oxygen saturation of 3% or less is stored for at least 14 days. In another aspect, oxygen reduced stored blood has an initial oxygen saturation of 3% or less is stored for at least 21 days. In another aspect, oxygen reduced stored blood has an initial oxygen saturation of 3% or less is stored for at least 28 days. In another aspect, oxygen reduced stored blood has an initial oxygen saturation of 3% or less is stored for at least 35 days. In another aspect, oxygen reduced stored blood has an initial oxygen saturation of 3% or less is stored for at least 42 days.

The present disclosure provides for, and includes, a method for improving energy metabolism in a human patient in need of a blood transfusion comprising providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has an increased risk of oxidative stress.

In an aspect of the present disclosure, oxygen reduced stored blood that has an initial oxygen saturation of 20% or less prior to being stored for a storage period, provided to a patient in need of a blood transfusion reduces the total number of units to be transfused. In an aspect the total number of units to be transfused is reduced by at least 1, at least 2, at least 3, at least 4, at least 5, at least 6, at least 7, at least 8, at least 9, and at least 10. In another aspect the total number of units to be transfused is reduced by between 1 and 2, between 2 and 4, between 4 and 6. Between 6 and 8, and between 8 and 10.

The present disclosure provides for, and includes, a method of reducing the risk of adverse transfusion events, including but not limiting to, inflammatory responses in a patient and in need of a blood transfusion comprising providing oxygen reduced stored blood having reduced levels of at least one inflammatory factor when compared to non-oxygen reduced stored blood stored for an identical storage period wherein said patient has an increased risk of an inflammatory response.

The present disclosure provides for, and includes, a method of a method of decreasing the risk of septic complications in critically ill patients, owing to the improved osmotic and mechanical resistance of oxygen controlled RBCs, which in turn decreases the likelihood of in vivo post-transfusion hemolysis and subsequently provides benefits in terms of iron overload and non-transferrin-bound iron (NTBI) burden in septic recipients.

As used herein, the term "greater" or "increased" means that the measured values of oxygen reduced and anaerobically stored blood, when compared to the measured values of otherwise equivalently treated normoxic or hyperoxic conventionally stored blood, are at least 1 standard deviation greater, with a sample size of at least 5 for each compared measured condition.

As used herein, the term "decreased" or "less" means that the measured values of oxygen reduced and anaerobically stored blood when compared to the measured values of otherwise equivalently treated normoxic or hyperoxic conventionally stored blood RBCs, are at least 1 standard deviation lower, with a sample size of at least 5 for each compared measured condition.

As used herein the term "about" refers to ±10%.

As used herein the term "less than" refers to a smaller amount and an amount greater than zero.

The terms "comprises," "comprising," "includes," "including," "having," and their conjugates mean "including but not limited to."

The term "consisting of" means "including and limited to."

The term "consisting essentially of" means that the composition, method or structure can include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" can include a plurality of compounds, including mixtures thereof.

Throughout this application, various aspects of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques, and procedures for accomplishing a given task including, but not limited to, providing a human patient in need of a blood transfusion with oxygen reduced stored blood having an initial oxygen saturation of 20% or less and stored for at least 2 days.

As used herein, the term "equivalent" means that the measured values of oxygen reduced stored blood with 20, 10, 5, and <3% $SO_2$ when compared to the measured values of otherwise equivalently treated normoxic or hyperoxic conventionally stored blood, are within 1 standard deviation of each other with a sample size of at least 4 for each compared measured condition.

In an aspect, the present disclosure provides for the following embodiments:

Embodiment 1: A method of reducing the risk of an inflammatory response in a human patient and in need of a blood transfusion comprising
providing oxygen reduced stored blood for transfusion into a human patient in need of a blood transfusion having an increased risk of an inflammatory response, wherein said oxygen reduced stored blood has an initial oxygen saturation of 20% or less prior to being stored for a storage period and said oxygen reduced stored blood has reduced levels of at least one inflammatory factor when compared to non-oxygen reduced stored blood stored for an identical storage period.

Embodiment 2: The method of embodiment 1, wherein said human patient and in need of a blood transfusion is selected from the group consisting of a surgery patient requiring a tissue perfusion bypass, a patient having chronic vascular inflammation, a patient having chronic inflammatory bowel disease, a patient having chronic obstructive pulmonary disease (COPD), a patient having sickle cell disease, a patient having thalassemia, a patient having organ failure, a patient having systemic inflammatory response syndrome (SIRS), a patient having diabetes mellitus, a patient having Bechet's disease, a patient having rheumatoid arthritis, a patient having smoke inhalation, and a patient having a combination thereof.

Embodiment 3: The method of embodiment 2, wherein said human patient and in need of a blood transfusion has a reduction in the risk of a delayed hemolytic transfusion reaction, an injury from ischemia reperfusion, hypercoagulation, a transfusion related acute lung injury (TRALI), systemic inflammatory response syndrome (SIRS), multiple organ dysfunction syndrome (MODS), or a combination thereof.

Embodiment 4: The method of embodiment 2, wherein said inflammatory response is aggravating an inflammatory response selected from the group consisting of chronic vascular inflammation, chronic inflammatory bowel disease, and combinations thereof.

Embodiment 5: The method of embodiment 1, wherein said at least one inflammatory factor is selected from the group consisting of
leukotriene,
8-isoprostane,
thromboxane,
hydroxyicosatetraenoic acid (HETE), and
combinations thereof.

Embodiment 6: The method of embodiment 5, further comprising an inflammatory cytokine selected from RANTES, eotaxin 1, or soluble CD40-ligand (SCD40L).

Embodiment 7: The method of embodiment 1, wherein said storage period is at least 2 days, 7 days, 14 days, 21 days, 28 days, or longer.

Embodiment 8: The method of embodiment 1, wherein said human patient in need of a blood transfusion is a patient in need of multiple transfusions.

Embodiment 9: The method of embodiment 5, wherein said storage period is two days and oxygen reduced stored blood comprises
- a reduced level of thromboxane B2 when said initial oxygen saturation is 5% or less,
- an increased level of glutathione (GSH),
- a reduced percentage of methemoglobin,
- an increased level of ATP, and
- an increased level of 2,3-diphosphoglycerate (DPG)
- wherein said increase or said reduction in said oxygen reduced stored blood is relative to non-oxygen reduced stored blood stored for an identical storage period.

Embodiment 10: The method of embodiment 9, wherein said storage period is at least 7 days and said oxygen reduced stored blood further comprises an increased ratio of phosphatidylinositol 4-phosphate to phosphatidylinositol (3,4,5)-triphosphate
- wherein said increased ratio in said oxygen reduced stored blood is relative to non-oxygen reduced stored blood stored for an identical storage period.

Embodiment 11: The method of embodiment 10, wherein said storage period is at least 14 days and said oxygen reduced stored blood further comprises
- a reduced level of leukotriene B4,
- a reduced level of hydroxyeicosatetraenoic acid (HETE) when said initial oxygen saturation is 10% or less,
- an increased level of methylenetetrahydrofolate, and
- an increased level of glutamate
- wherein said increase or said reduction in said oxygen reduced stored blood is relative to non-oxygen reduced stored blood stored for an identical storage period.

Embodiment 12: The method of embodiment 11, wherein said storage period is at least 21 days and said oxygen reduced stored blood further comprises
- a higher ratio of GSH to glutathione disulfide (GSSG) (GSH/GSSG ratio) when said oxygen saturation is between 5% and 10%,
- an increased reservoir of nicotinamide adenine dinucleotide (NAD),
- an increased reservoir of nicotinamide adenine dinucleotide+hydrogen (NADH), and
- a reduced level of dioxidation of Cys152 in Glyceraldehyde-3-Phosphate Dehydrogenase (GAPDH) when said initial oxygen saturation is about 5%
- wherein said increase or said reduction in said oxygen reduced stored blood is relative to non-oxygen reduced stored blood stored for an identical storage period.

Embodiment 13: The method of embodiment 12, wherein said storage period is at least 28 days and said oxygen reduced stored blood further comprises
- an increase level of NADPH
- an increased ratio of NADPH/NADP$^+$, and
- an increased level of cysteine
- wherein said increase or said reduction in said oxygen reduced stored blood is relative to non-oxygen reduced stored blood stored for an identical storage period.

Embodiment 14: The method of embodiment 1, further comprising transfusing at least one unit of said oxygen reduced stored blood.

Embodiment 15: The method of embodiment 1, wherein said initial oxygen saturation is 10% or less, 5% or less, or 3% or less.

Embodiment 16: A method for reducing oxidative stress in a human patient in need of a blood transfusion comprising
providing oxygen reduced stored blood for transfusion into a human patient in need of a blood transfusion having an increased risk for transfusion mediated oxidative stress, wherein said oxygen reduced stored blood has an initial oxygen saturation of 20% or less prior to being stored for a storage period wherein said patient has an increased risk of oxidative stress.

Embodiment 17: The method of embodiment 16, wherein said human patient in need of a blood transfusion having an increased risk of oxidative stress is selected from the group consisting of a trauma patient requiring four or more units of blood, a trauma patient requiring ten or more units of blood, a patient having sickle cell disease, a patient having thalassemia, and combinations thereof.

Embodiment 18: The method of embodiment 16, wherein said reduction in oxidative stress is a reduction of oxidizing compounds, increased levels of oxidation protective compounds, and combinations thereof.

Embodiment 19: The method of embodiment 16, wherein said storage period is two days and oxygen reduced stored blood comprises
- a reduced level of thromboxane B2 when said initial oxygen saturation is 5% or less,
- an increased reservoir of nicotinamide adenine dinucleotide phosphate (NADP),
- an increased reservoir of reduced nicotinamide adenine dinucleotide phosphate (NADPH),
- an increased level of glutathione (GSH),
- a reduced percentage of methemoglobin,
- an increased level of ATP, and
- an increased level of 2,3-diphosphoglycerate (DPG)
- wherein said increase or said reduction in said oxygen reduced stored blood is relative to non-oxygen reduced stored blood stored for an identical storage period.

Embodiment 20: The method of embodiment 17, wherein said storage period is at least 7 days and said oxygen reduced stored blood further comprises
- an increased ratio of phosphatidylinositol 4-phosphate to phosphatidylinositol (3,4,5)-triphosphate
- wherein said increase in said oxygen reduced stored blood is relative to non-oxygen reduced stored blood stored for an identical storage period.

Embodiment 21: The method of embodiment 20, wherein said storage period is at least 14 days and said oxygen reduced stored blood further comprises
- a reduced level of leukotriene B4,
- a reduced level of hydroxyeicosatetraenoic acid (HETE) when said initial oxygen saturation is 10% or less,
- an increased level of methylenetetrahydrofolate, and
- an increased level of glutamate
- wherein said increase or said reduction in said oxygen reduced stored blood is relative to non-oxygen reduced stored blood stored for an identical storage period.

Embodiment 22: The method of embodiment 21, wherein said storage period is at least 21 days and said oxygen reduced stored blood further comprises
- a higher ratio of GSH to glutathione disulfide (GSSG) (GSH/GSSG ratio) when said initial oxygen saturation is between 5% and 10%, an increased reservoir of nicotinamide adenine dinucleotide (NAD), an increased reservoir of nicotinamide adenine dinucleotide+hydrogen (NADH), and a reduced level of dioxidation of Cys152 in Glyceraldehyde-3-Phosphate Dehydrogenase (GAPDH) when said initial oxygen saturation is about 5% wherein said increase or said reduction in said oxygen reduced stored blood is relative to non-oxygen reduced stored blood stored for an identical storage period.

Embodiment 23: The method of embodiment 22, wherein said storage period is at least 28 days and said oxygen reduced stored blood further comprises an increase level of NADPH an increased ratio of NADPH/NADP$^+$, an increased level of cysteine, and an increased levels of urate wherein said increase or said reduction in said oxygen reduced stored blood is relative to non-oxygen reduced stored blood stored for an identical storage period.

Embodiment 24: The method of embodiment 23, wherein said storage period is at least 42 days and said oxygen reduced stored blood further comprises a reduced level of oxidation of beta-hemoglobin at residue H93 wherein said reduction in said oxygen reduced stored blood is relative to non-oxygen reduced stored blood stored for an identical storage period.

Embodiment 25: The method of embodiment 16, further comprising transfusing at least one unit of said oxygen reduced stored blood.

Embodiment 26: The method of embodiment 16, wherein said initial oxygen saturation is 10% or less, 5% or less, or 3% or less.

Embodiment 27: The method of embodiment 16, wherein said human patient in need of a blood transfusion is a patient in need of a massive transfusion or chronic transfusions.

Embodiment 28: The method of embodiment 17, wherein said storage period is at least 14 days, 21 days, 28 days, or longer.

Embodiment 29: The method of embodiment 17, wherein said human patient in need of a blood transfusion has sickle cell disease with a hemoglobin concentration below 5 g/dL, thalassemia with a hemoglobin concentration below 7 g/dL.

Embodiment 30: The method of embodiment 29, wherein said human patient has sickle cell disease and the peak, centerline flow velocity of the middle cerebral artery is greater than 200 cm/sec as determined by transcranial Doppler ultrasound (TCD).

Embodiment 31: The method of embodiment 29, wherein said human patient has sickle cell disease and receives transfusions to reduce sickle hemoglobin levels to below 30% of total hemoglobin in the body.

Embodiment 32: The method of embodiment 29, wherein said human patient has sickle cell disease and receives transfusions about every thirty days.

Embodiment 33: The method of embodiment 29, wherein said human patient has sickle cell disease and is experiencing acute chest syndrome.

Embodiment 34: The method of embodiment 29, wherein said human patient has sickle cell disease and is experiencing a vaso-occlusive crisis.

Embodiment 35: The method of embodiment 34, wherein said human patient has sickle cell disease and in is need of surgery, wherein said patient receives one or more pre-operative transfusions to reduce perioperative hypoxia, hypoperfusion, or acidosis.

Embodiment 36: A method for reducing the risk of an adverse event in a hemoglobinopathy patient in need of a blood transfusion comprising providing oxygen reduced stored blood for transfusion into a hemoglobinopathy patient in need of a blood transfusion, wherein said oxygen reduced stored blood has an initial oxygen saturation of 20% or less prior to being stored for a storage period wherein said patient has an increased risk of an adverse event.

Embodiment 37: The method of embodiment 36, wherein said hemoglobinopathy patient in need of a blood transfusion is a sickle cell patient.

Embodiment 38: The method of embodiment 36, wherein said adverse event that is reduced is selected from the group consisting of eryptosis, delayed hemolytic transfusion reaction, defects in red blood asymmetry, severe anemia, reduced frequency of vaso-occlusive crisis, reduced perioperative hypoxia, reduced perioperative hypoperfusion, reduced perioperative acidosis, reticulocytopenia, and combinations thereof.

Embodiment 39: The method of embodiment 37, wherein said hemoglobinopathy patient in need of a blood transfusion is a sickle cell patient having a hemoglobin concentration below 5 g/dL.

Embodiment 40: The method of embodiment 37, wherein said hemoglobinopathy patient has sickle cell disease and the peak, centerline flow velocity of the middle cerebral artery is greater than 200 cm/sec as determined by transcranial Doppler ultrasound (TCD).

Embodiment 41: The method of embodiment 38, wherein said sickle cell patient is further provided oxygen reduced stored blood for transfusion one or more times to lower the total sickle hemoglobin concentration below 30% of total hemoglobin concentration.

Embodiment 42: The method of embodiment 37, wherein said sickle cell patient is experiencing acute chest syndrome.

Embodiment 43: The method of embodiment 37, wherein said sickle cell patient is experiencing a vaso-occlusive crisis.

Embodiment 44: The method of embodiment 38, wherein said providing oxygen reduced stored blood for transfusion comprises providing chronic transfusion therapy wherein said transfusion is provided every three weeks or when hemoglobin concentrations decline below 5 g/dL.

Embodiment 45: The method of embodiment 36, wherein said hemoglobinopathy patient in need of a blood transfusion is a thalassemia patient in need of a blood transfusion.

Embodiment 46: The method of embodiment 45, wherein said thalassemia patient in need of a blood transfusion is a thalassemia patient having a hemoglobin concentration below 7 g/dL.

Embodiment 47: The method of embodiment 45, wherein said providing oxygen reduced stored blood for transfusion comprises providing chronic transfusion therapy wherein said transfusion is provided every two weeks or when hemoglobin concentrations decline below 7 g/dL.

Embodiment 48: The method of embodiment 37, wherein said sickle cell patient is in need of surgery, wherein said patient receives one or more pre-operative transfusions to reduce perioperative hypoxia, hypoperfusion, and acidosis.

Embodiment 49: The method of embodiment 36, wherein said adverse event is a delayed hemolytic transfusion reaction and said hemoglobinopathy patient in need of a blood transfusion is a sickle cell patient.

Embodiment 50: The method of embodiment 36, wherein said adverse event is reticulocytopenia.

Embodiment 51: The method of embodiment 36, wherein said adverse event occurs between 1 and 10 days following said providing oxygen reduced stored blood for transfusion.

Embodiment 52: The method of embodiment 50, wherein said adverse event is severe anemia.

Embodiment 53: The method of embodiment 36, wherein said storage period is two days and oxygen reduced stored blood comprises
a reduced level of thromboxane B2 when said initial oxygen saturation is 5% or less,
an increased reservoir of nicotinamide adenine dinucleotide phosphate (NADP),
an increased reservoir of reduced nicotinamide adenine dinucleotide phosphate (NADPH),
an increased level of glutathione (GSH),
a reduced percentage of methemoglobin,
an increased level of ATP, and
an increased level of 2,3-diphosphoglycerate (DPG)
wherein said increase or said reduction in said oxygen reduced stored blood is relative to non-oxygen reduced stored blood stored for an identical storage period.

Embodiment 54: The method of embodiment 48, wherein said storage period is at least 7 days and said oxygen reduced stored blood further comprises
an increased ratio of phosphatidylinositol 4-phosphate to phosphatidylinositol (3,4,5)-triphosphate
wherein said increase in said oxygen reduced stored blood is relative to non-oxygen reduced stored blood stored for an identical storage period.

Embodiment 55: The method of embodiment 54, wherein said storage period is at least 14 days and said oxygen reduced stored blood further comprises
a reduced level of leukotriene B4,
a reduced level of hydroxyeicosatetraenoic acid (HETE) when said initial oxygen saturation is 10% or less,
an increased level of methylenetetrahydrofolate, and
an increased level of glutamate
wherein said increase or said reduction in said oxygen reduced stored blood is relative to non-oxygen reduced stored blood stored for an identical storage period.

Embodiment 56: The method of embodiment 55, wherein said storage period is at least 21 days and said oxygen reduced stored blood further comprises
a higher ratio of GSH to glutathione disulfide (GSSG) (GSH/GSSG ratio) when said initial oxygen saturation is between 5% and 10%,
an increased reservoir of nicotinamide adenine dinucleotide (NAD),
an increased reservoir of NADH, and
a reduced level of dioxidation of Cys152 in Glyceraldehyde-3-Phosphate Dehydrogenase (GAPDH) when said initial oxygen saturation is about 5%
wherein said increase or said reduction in said oxygen reduced stored blood is relative to non-oxygen reduced stored blood stored for an identical storage period.

Embodiment 57: The method of embodiment 56, wherein said storage period is at least 28 days and said oxygen reduced stored blood further comprises
an increase level of NADPH
an increased ratio of NADPH/NADP$^+$,
an increased level of cysteine, and
an increased levels of urate
wherein said increase or said reduction in said oxygen reduced stored blood is relative to non-oxygen reduced stored blood stored for an identical storage period.

Embodiment 58: The method of embodiment 57, wherein said storage period is at least 42 days and said oxygen reduced stored blood further comprises a reduced level of oxidation of beta-hemoglobin at residue H93 wherein said reduction in said oxygen reduced stored blood is relative to non-oxygen reduced stored blood stored for an identical storage period.

Embodiment 59: The method of embodiment 36, further comprising transfusing at least one unit of said oxygen reduced stored blood.

Embodiment 60: The method of embodiment 36, wherein said initial oxygen saturation is 10% or less, 5% or less, or 3% or less.

Embodiment 61: The method of embodiment 36, wherein said hemoglobinopathy patient in need of a blood transfusion is a patient in need of a massive transfusion or chronic transfusions.

Embodiment 62: The method of embodiment 36, wherein said storage period is at least 14 days, 21 days, 28 days, or longer.

Embodiment 63: A method for reducing cardiac, renal and gastrointestinal ischemia reperfusion injury in a patient in need of a blood transfusion comprising
providing oxygen reduced stored blood that has an initial oxygen saturation of 20% or less prior to being stored for a storage period for transfusion to a human patient in need of a blood transfusion and having an increased risk for cardiac, renal and gastrointestinal ischemia reperfusion injury.

Embodiment 64: The method of embodiment 63, wherein said patient in need of a blood transfusion is a patient selected from the group consisting of a cardiac surgery patient, kidney transplant patient, liver resection patient, or colectomy patient.

Embodiment 65: The method of embodiment 63, wherein said reduced reperfusion injury is reduced hypercoagulability, cell damage, or oxidative damage.

Embodiment 66: The method of embodiment 63, wherein said storage period is at least two days and said oxygen reduced stored blood has
a reduced level of thromboxane B2 when said initial oxygen saturation is 5% or less,
an increased reservoir of nicotinamide adenine dinucleotide phosphate (NADP),
an increased reservoir of reduced nicotinamide adenine dinucleotide phosphate (NADPH),
an increased level of glutathione (GSH),
a reduced percentage of methemoglobin,
an increased level of ATP, and
an increased level of 2,3-diphosphoglycerate (DPG)

wherein said increase or said reduction in said oxygen reduced stored blood is relative to non-oxygen reduced stored blood stored for an identical storage period.

Embodiment 67: The method of embodiment 64, wherein said storage period is at least 14 days and said oxygen reduced stored blood further comprises
a reduced level of leukotriene B4,
a reduced level of hydroxyeicosatetraenoic acid (HETE) when said initial oxygen saturation is 10% or less,
an increased level of methylenetetrahydrofolate, and
an increased level of glutamate.

Embodiment 68: The method of embodiment 67, wherein said storage period is at least 21 days and said oxygen reduced stored blood further comprises
a higher ratio of GSH to glutathione disulfide (GSSG) (GSH/GSSG ratio) when said initial oxygen saturation is between 5% and 10%,
an increased reservoir of nicotinamide adenine dinucleotide (NAD),
an increased reservoir of NADH, and
a reduced level of dioxidation of Cys152 in Glyceraldehyde-3-Phosphate Dehydrogenase (GAPDH) when said initial oxygen saturation is about 5%
wherein said increase or said reduction in said oxygen reduced stored blood is relative to non-oxygen reduced stored blood stored for an identical storage period.

Embodiment 69: The method of embodiment 68, wherein said storage period is at least 28 days and said oxygen reduced stored blood further comprises
an increase level of NADPH
an increased ratio of NADPH/NADP$^+$,
an increased level of cysteine, and
an increased levels of urate
wherein said increase or said reduction in said oxygen reduced stored blood is relative to non-oxygen reduced stored blood stored for an identical storage period.

Embodiment 70: The method of embodiment 69, wherein said storage period is at least 42 days and said oxygen reduced stored blood further comprises a reduced level of oxidation of beta-hemoglobin at residue 1193 wherein said increase or said reduction in said oxygen reduced stored blood is relative to non-oxygen reduced stored blood stored for an identical storage period.

Embodiment 71: The method of embodiment 70, further comprising transfusing at least one unit of said oxygen reduced stored blood.

Embodiment 72: The method of embodiment 63, wherein said initial oxygen saturation is 10% or less, 5% or less, or 3% or less.

Embodiment 73: The method of embodiment 63, wherein said human patient in need of a blood transfusion is a patient in need of a massive transfusion or chronic transfusions.

Embodiment 74: A method for reducing delayed hemolytic transfusion reaction in a patient in need of a blood transfusion comprising providing oxygen reduced stored blood that has an initial oxygen saturation of 20% or less prior to being stored for a storage period wherein said patient has an increased risk of a delayed hemolytic transfusion reaction.

Embodiment 75: The method of embodiment 74, wherein said patient in need of a blood transfusion is a patient selected from the group consisting of a sickle cell patient or a thalassemia patient, a trauma patient receiving massive transfusion, and a patient receiving chronic transfusions.

Embodiment 76: The method of embodiment 74, wherein said storage period is at least 7 days and said oxygen reduced stored blood has
an increased level of glutathione (GSH),
an increased level of ATP, and
an increased ratio of phosphatidylinositol 4-phosphate to phosphatidylinositol (3,4,5)-triphosphate,
wherein said increase in said oxygen reduced stored blood is relative to non-oxygen reduced stored blood stored for an identical storage period.

Embodiment 77: The method of embodiment 76, wherein said storage period is at least 14 days and said oxygen reduced stored blood further comprises
a reduced level of hydroxyeicosatetraenoic acid (HETE) when said initial oxygen saturation is 10% or less
wherein said reduction in said oxygen reduced stored blood is relative to non-oxygen reduced stored blood stored for an identical storage period.

Embodiment 78: The method of embodiment 77, wherein said storage period is at least 21 days and said oxygen reduced stored blood further comprises
a higher ratio of GSH to glutathione disulfide (GSSG) (GSH/GSSG ratio) when said initial oxygen saturation is between 5% and 10%, and
an increased reservoir of nicotinamide adenine dinucleotide+hydrogen (NADH)
wherein said increase in said oxygen reduced stored blood is relative to non-oxygen reduced stored blood stored for an identical storage period.

Embodiment 79: The method of embodiment 78, wherein said storage period is at least 28 days and said oxygen reduced stored blood further comprises
an increase level of NADPH, and
an increased level of cysteine
wherein said increase in said oxygen reduced stored blood is relative to non-oxygen reduced stored blood stored for an identical storage period.

Embodiment 80: The method of embodiment 74, wherein said patient in need of a blood transfusion is a patient having sickle cell disease or thalassemia.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1: Collection of Blood and Sample Preparation

A total of up to 6 double red blood cell (2RBC) units are collected from healthy donors by apheresis, leukoreduced, and stored in CPD2/AS-3. 2RBC units are pooled and split into six samples of hyperoxic, normoxic, or various levels of hypoxia 2RBCs, as described in Table 3. Each 2RBC unit (samples 3 to 6) to be reduced is processed by connecting the collection bag to a Sorin D100 membrane oxygenator (Sorin Group, Arvada, Colo.) and pumped at a flow rate of 700 ml/minute with a mixture of 95% $N_2$ and 5% $CO_2$ gas to achieve pre-storage % $SO_2$, while maintaining pCO2 ~30 mmHg (37° C.). Oxygen-reduced units are stored anaerobically in a canister, and sampling, as well as separation of RBC and supernatant are carried out in N2-filled anaerobic glove box. For hyperoxic units (Sample 2), calculated volume of $O_2$ gas is added sterilely to achieve 90-98% $SO_2$. Hyperoxic (Sample 2) and control (Sample 1) units are stored in ambient air. All units are stored for 6 weeks at 4° C. and sampled at days 0, 2, 7, 14, 21, 28, 35 and 42. As shown in FIG. 1, % $SO_2$ in hypoxic units continue to decrease and hyperoxic units remain unchanged over the 42 days of storage.

On days 1, 21, and 42, cell counts, HCT, FHgB, ATP, 2,3-DPG analysis is performed. RBCs and supernatants are processed as previously described in D'Alessandro, A., et al. *Transfusion*, 55(6), 1155-1168) and analyzed via UHPLC-MS (Vanquish, Q Exactive—Thermo Fisher, San Jose, Calif. and Bremen, Germany). Metabolite assignments and isotopologue distributions are determined against internal standard libraries through Maven (Nemkov, T. et al. Amino Acids 2015; 47(11):2345-2357) (hereby incorporated by reference in its entirety). Technical reproducibility (CVs) is assessed by monitoring heavy labeled standard mixes and the xenometabolite 5-fluorouracil (2.5 µM). Absolute quantitation is performed against spiked in heavy standards (Cambridge Isotope Laboratories).

TABLE 3

List of sample designations and target
$SO_2$/$pCO_2$ levels for LR-pRBC blood volumes

| Sample Designation | Target Parameters $SO_2$ (%)/$pCO_2$ (Torr) (37°) |
|---|---|
| [A1], [B1], [C1], [D1] | Unprocessed Control |
| [A2], [B2], [C2], [D2] | >90%/75 ± 5 Torr |
| [A3], [B3], [C3], [D3] | 20 ± 2%/25 ± 5 Torr |
| [A4], [B4], [C4], [D4] | 10 ± 2%/25 ± 5 Torr |
| [A5], [B5], [C5], [D5] | 5 ± 2%/25 ± 5 Torr |
| [A6], [B6], [C6], [D6] | <3%/25 ± 5 Torr |

Example 2: Reduction of Pro-Inflammatory Molecules in Oxygen Reduced Stored Blood The levels of three potent pro-inflammatory biological response modifiers (BRM)—Leukotriene B4, Thromboxane B2, and hydroxyeicosatetraenoic acid (HETE)—are assessed in the 6 units of blood described in Example 1. Leukotriene B4 is an effective polymorphonuclear neutrophil chemoattractant. As shown in FIG. 2, leukotriene B4 accumulates in conventionally stored normoxic (control; solid line) and hyperoxic RBCs over 42 days of storage, however, leukotriene B4 remains undetectable in hypoxic RBCs.

Thromboxane A2 is an unstable, potent vasoconstrictor which stimulates vessel contraction through vascular smooth muscle thromboxane A2 receptors. Thromboxane B2, a more stable form of thromboxane A2, accumulates less in hypoxic RBCs over 42 days of storage when $SO_2$ is <3%, compared to control (solid line) RBCs (FIG. 3).

Figure 4A:
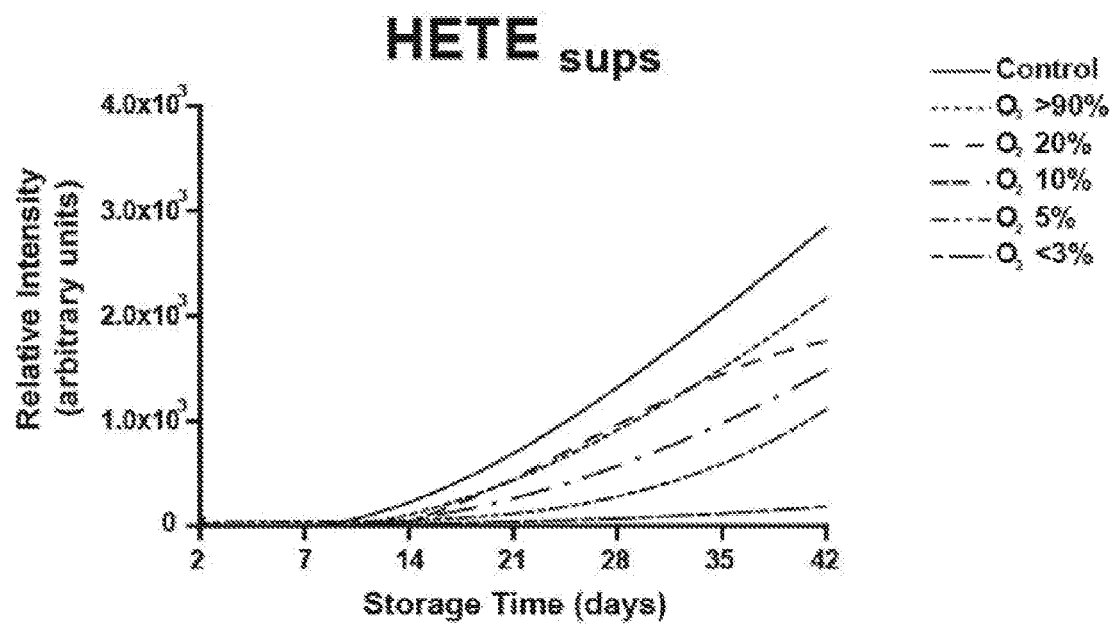
FIGS. 4A and 4B are graphs presenting the results of an experiment according to the present disclosure, comparing the levels of hydroxyeicosatetraenoic acid (HETE) of conventionally stored normoxic (solid line) and hyperoxic (---) and oxygen reduced stored blood with an initial an initial percent $SO_2$ of 20, 10, 5, and <3%.
Figure 4B:
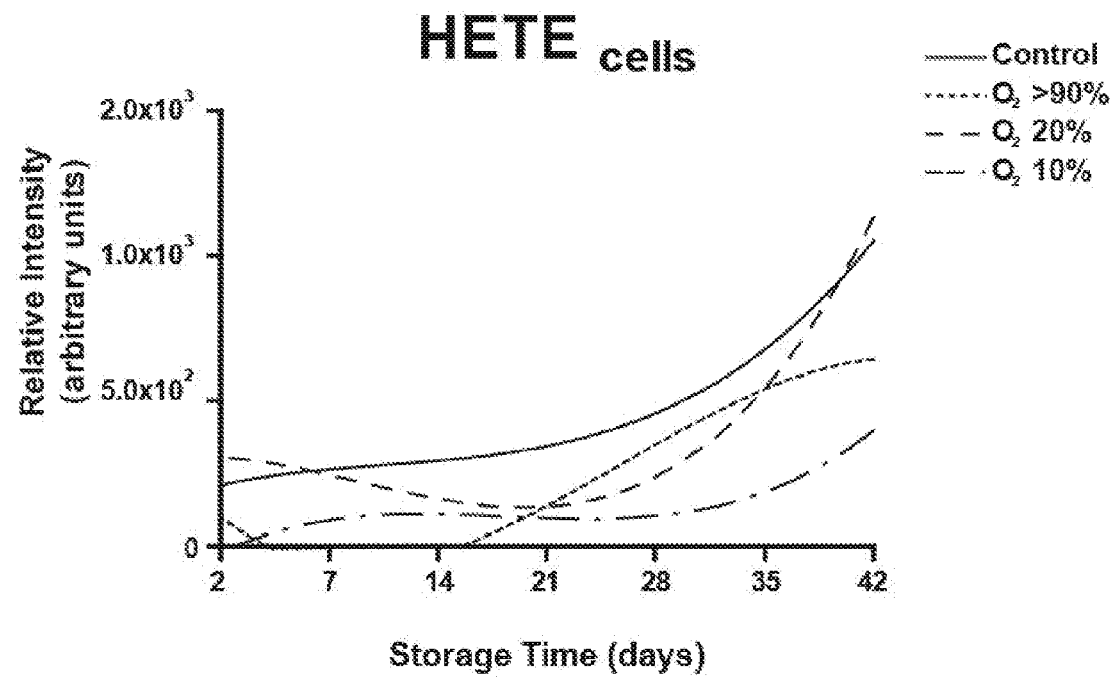

As shown in FIGS. 4A and 4B, oxidized lipid products, like HETEs, accumulate less in hypoxic stored blood compared to normoxic and hyperoxic stored blood in supernatant. This decrease in HETE accumulation in hypoxic RBCs compared to normoxic (solid line) blood is also displayed in the cells.

Example 3: Determination of Glucose Metabolism Using $^{13}C_{1,2,3}$-Glucose

Relative flux of glucose through glycolysis (EMP) and pentose pathway (PPP) can be determined by including $^{13}C_{1,2,3}$-glucose ($^{13}$C-glucose) in the additive solution. $^{13}$C-lactate produced by oxidative PPP does not include $^{13}$C at all, or two ($^{13}C_{2,3}$-lactate), while lactate produced directly from glucose via EMP has either all three carbons with 13C or none at all.

Two grams of $^{13}$C 1,2,3-glucose (anhydrous) is dissolved in 36.4 mL of deionized tissue culture grade water to make ~300 mM glucose solution. The resulting solution is filter sterilized into a 50 mL sterile tube inside laminar flow hood and transferred into a 50 mL sampling PVC bag using sterile technique. Pooled blood as described is injected with 7.2 mL of the 300 mM sterile 13C-glucose solution before being split into oxygenated and oxygen reduced units. The AS-3 described above is calculated to contain approximately 55 mM glucose and the injection of sterile 13C-glucose solution adds an additional approximately 11 mM glucose to the pooled blood.

Example 4: Lower Intracellular Redox Potential

Figure 5:
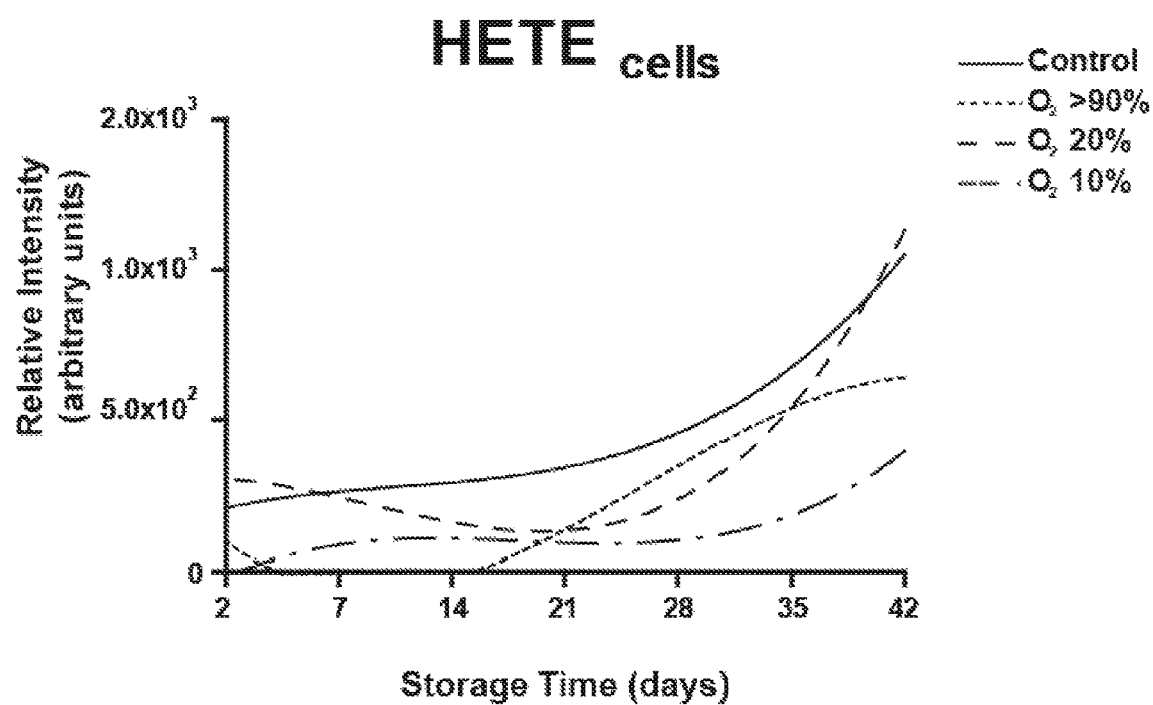
Figure 6:
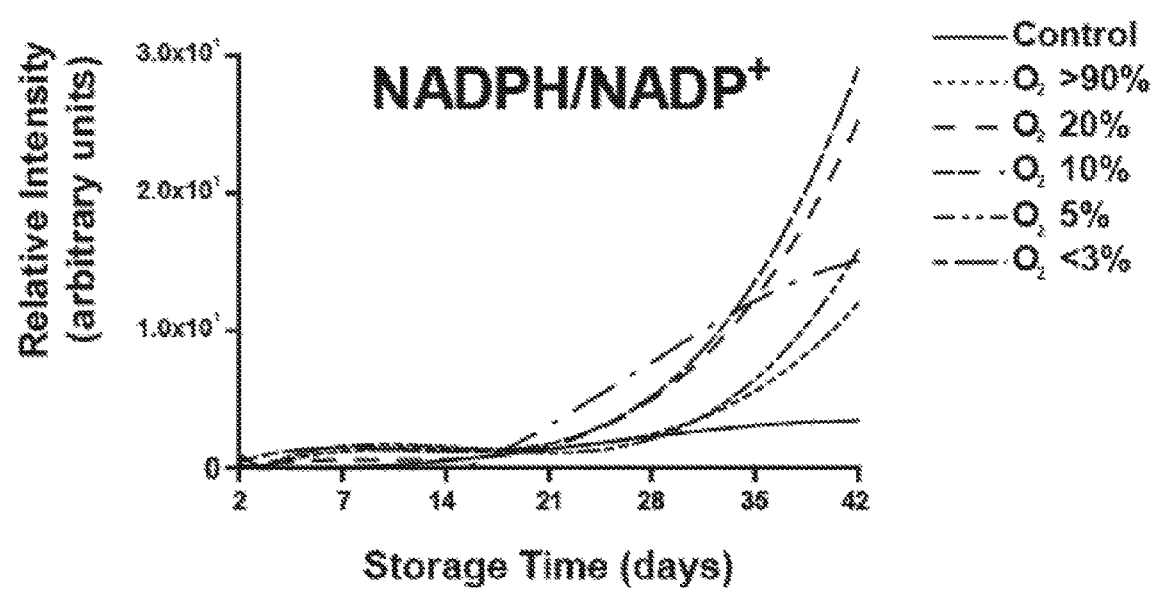
Figure 7:
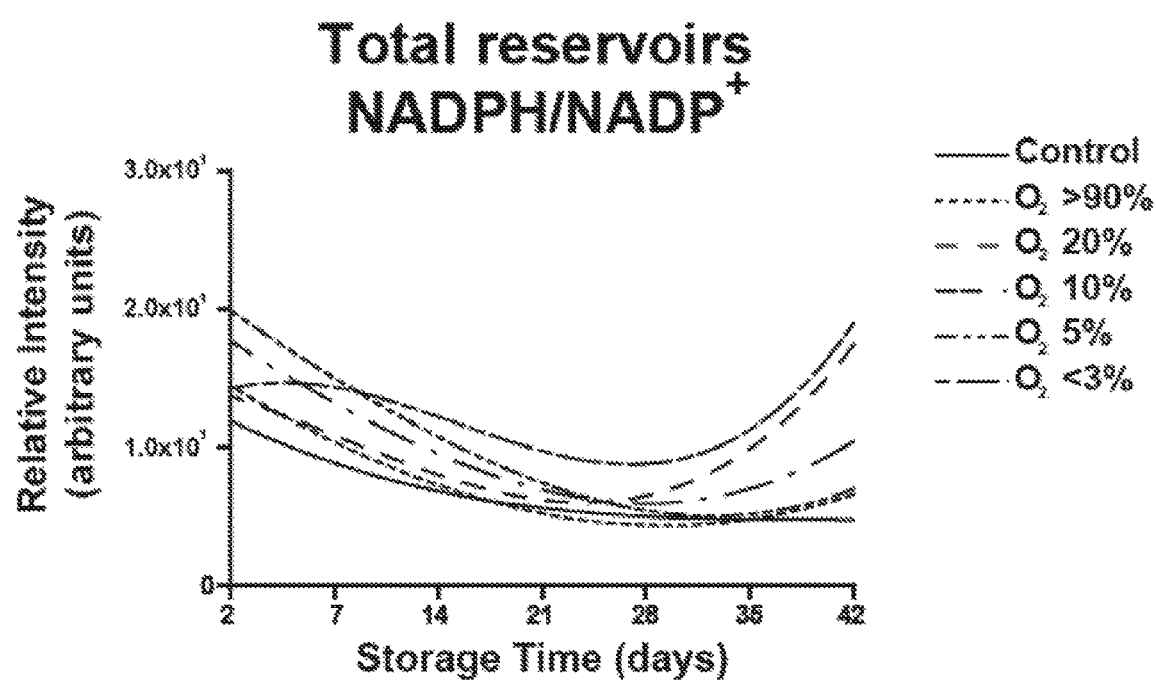

Under normal storage conditions lesions form in RBC. The oxidative lesion can affect oxygen-dependent metabolic modulation, promoting GAPDH binding to the N-terminal or other residues of band 3, promoting a metabolic shift from EMP to the PPP as to generate reducing equivalents (NADPH) and attempt to restore the redox poise. However, as shown in FIG. 5, FIG. 6, and FIG. 7 oxygen reduced stored blood has a higher rate of NADPH and NADPH/NADP$^+$ synthesis compared to control blood (solid line). Thereby the oxygen reduced stored blood that is stored up to 42 days have lower levels of oxidative stress.

Oxygen reduced stored blood further shows a higher rate of NADH+ NAD pool synthesis compared to control and hyperoxic blood (FIG. 8). The beneficial effects of oxygen reduced stored blood is seen between 21 to 42 days of storage.

Figure 9:
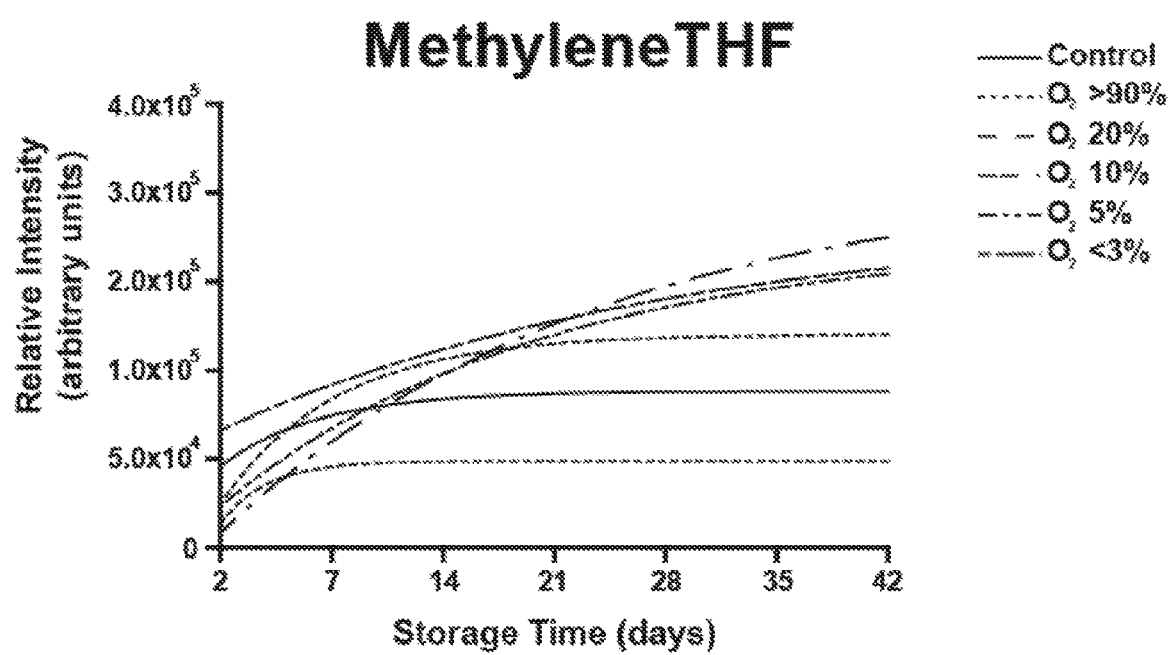

Oxygen reduced stored blood also has increased methylenetetrahydrofolate (methylene THF) levels compared to control (solid line). Methylenetetrahydrofolate promotes the production of NADPH. Specifically, oxygen reduced stored blood shows a 1.4- and 2-fold increase of methylenetetrahydrofolate compared to control blood, at 14 and 42 days, respectively (FIG. 9).

Figure 10:
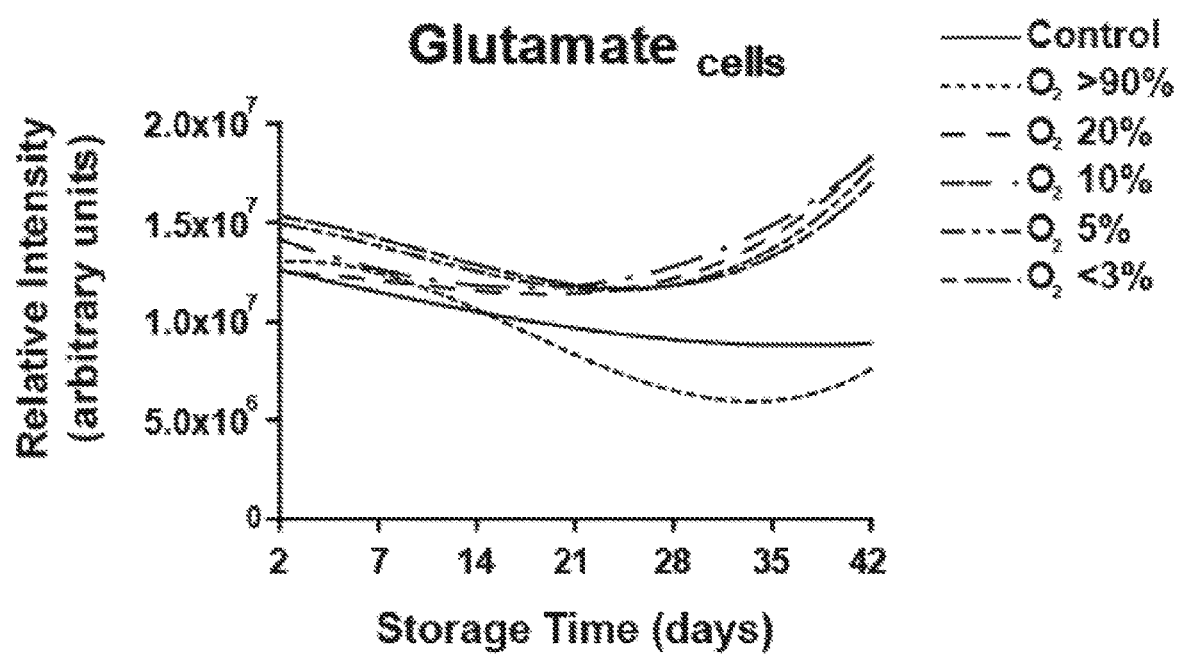

Glutamate, a precursor for glutathione synthesis, is also increased in oxygen reduced stored blood compared to control (solid line) beginning at day 14 (FIG. 10). Specifically, glutamate is increased by approximately 2-fold in oxygen reduced stored blood at day 42 of storage compared to control (solid line). Further, glutathione (GSH) levels are increased in oxygen reduced stored blood in a dose-dependent manner over the 42 day storage period compared to control (solid line). Particularly, oxygen reduced stored blood show a 2-fold increase in glutathione over control at days 7 and 42 (FIG. 11). The high glutamate and reduced glutathione and GSH/GSSG ratios (FIG. 12) are suggestive of decreased oxidative stress in oxygen reduced stored blood.

Cysteine is a rate limiting substrate of GSH synthesis and the cysteine levels are evaluated in control, hyperoxic, and oxygen reduced stored blood. Cysteine synthesis through methionine catabolism via cytosolic one-carbon metabolism reactions is the highest in oxygen reduced stored blood. The increase in cysteine synthesis over control blood is evident after 28 days of storage (FIG. 13).

Another indicator of reduced oxidative stress is the accumulation of the antioxidant urate. As shown in FIG. 14, oxygen reduced stored blood displays increased levels of urate compared to control blood after 28 to 42 days of storage.

Example 5: Higher Energetic State of RBC

As shown in FIG. 15, oxygen reduced stored blood exhibits increased flux through EMP and thereby generate higher levels of ATP and 2, 3-DPG. oxygen reduced stored blood also exhibits increased de novo ATP via the Pentose Phosphate Pathway between 7 to 35 days of storage (FIG. 16).

Oxidation of active site residue Cys152 and His179 compromise membrane binding and catalytic activity of GAPDH. During storage, especially at days 21 and 42, redox-sensitive residue Cys152, is observed to be oxidatively modified in oxygen reduced stored blood (grey bars) compared to control (black bars; FIG. 17). This loss in catalytic activity of results in GAPDH migration to the membrane and removal through vesiculation.

Example 6: Reduction of Eryptosis and Vesculation in Oxygen Reduced Stored Blood Eryptosis can also be responsible for increased inflammation in transfusion recipients. Eryptosis is the suicidal death of RBC which is characterized by reduced phosphatidylserine exposure, cell shrinkage, and membrane blebbing. Reduced phosphatidylserine asymmetry combined with cell surface glycoproteins, mediated by membrane vesiculation, play a role in RBC clearance.

Samples are prepared and sampled as described in example 1. PIP phosphorylation to PIP3 is measured in the 6 normoxic, hyperoxic, and hypoxic stored blood samples. As shown in FIG. 18A and FIG. 18B, phosphorylation of PIP to the calcium channel agonist PIP3 is reduced under anaerobic conditions. Phosphorylation of PIP to PIP3 is reduced in a dose-dependent manner in oxygen reduced stored blood compared to control (solid line), over 42 days of storage. This prevention of PIP phosphorylation to PIP3 in oxygen reduced stored blood prevents the effect of PIP3 on Mg/Ca pumps, that would otherwise result in increased intracellular calcium, inhibition of ATP synthase and compromise RBC morphology and survival through the activation of eryptotic cascades (via calcium-dependent calpains and caspases).

Oxygen reduced stored blood result in a reduction in microparticle formation as consequences of oxidation of beta-hemoglobin at residue H93 compared to control after 42 days of storage (FIG. 19).

Methemoglobin is unstable and denatures into hydrophobic and reactive globin and hemin, which can disrupt RBC membrane, induce vesiculation, induce morphology change and catalyze hydroxyl radical generation. As shown in FIG. 20, oxygen reduced stored blood has reduced Methemoglobin levels at every time point analyzed compared to control (solid line) and hyperoxic stored blood.

Methemoglobin reductase, the enzyme responsible for the reduction of oxidized iron in the prosthetic group of hemoglobin, requires NAD(P)H to function. Increases in NADH/NAD+ ratios are observed in hypoxically or anaerobically stored RBCs, owing to increased glycolytic fluxes (higher lactate/pyruvate ratios) and resulting from alterations of the cytosolic reducing environment owing to the removal of oxygen (consistent with the Nernst equation). These considerations contribute explaining the observed decreases in methemoglobin accumulation in hypoxically stored RBCs.

The invention claimed is:

1. A method of reducing the risk of an inflammatory response in a sickle cell human patient in need of a blood transfusion comprising administering oxygen reduced stored blood for transfusion into a sickle cell human patient in need of a blood transfusion having an increased risk of an inflammatory response, wherein said oxygen reduced stored blood has an initial oxygen saturation of 20% or less prior to being stored for a storage period and a reduced level of at least one inflammatory factor when compared to non-oxygen reduced stored blood stored for an identical storage period.

2. The method of claim 1, wherein said sickle cell patient in need of a blood transfusion has a reduction in the risk of a delayed hemolytic transfusion reaction (DHTR), systemic inflammatory response syndrome (SIRS), perioperative hypoxia, hypoperfusion, or a combination thereof.

3. The method of claim 1, wherein said at least one inflammatory factor is reduced leukotriene and hydroxyicosatetraenoic acid (HETE).

4. The method of claim 1, wherein said at least one inflammatory factor further comprises an inflammatory cytokine selected from RANTES, eotaxin 1, or soluble CD40-ligand (SCD40L).

5. The method of claim 1, wherein said storage period is at least 2 days, 7 days, 14 days, 21 days, or 28 days.

6. The method of claim 1, wherein said sickle cell patient in need of a blood transfusion is a patient in need of multiple transfusions.

7. The method of claim 5, wherein said storage period is two days and oxygen reduced stored blood comprises
   a reduced level of thromboxane B2 when said initial oxygen saturation is 5% or less,
   an increased level of glutathione (GSH),
   a reduced percentage of methemoglobin,
   an increased level of ATP, and
   an increased level of 2,3-diphosphoglycerate (DPG),
   wherein said increase or said reduction in said oxygen reduced stored blood is relative to said non-oxygen reduced stored blood stored for an identical storage period.

8. The method of claim 7, wherein said storage period is at least 7 days and said oxygen reduced stored blood further comprises:
   an increased ratio of phosphatidylinositol 4-phosphate to phosphatidylinositol (3,4,5)-triphosphate,
   wherein said increased ratio in said oxygen reduced stored blood is relative to said non-oxygen reduced stored blood stored for an identical storage period.

9. The method of claim 8, wherein said storage period is at least 14 days and said oxygen reduced stored blood further comprises
   a reduced level of leukotriene B4,
   a reduced level of hydroxyeicosatetraenoic acid (HETE) when said initial oxygen saturation is 10% or less, an increased level of methylenetetrahydrofolate, and
an increased level of glutamate,
wherein said increase or said reduction in said oxygen reduced stored blood is relative to said non-oxygen reduced stored blood stored for an identical storage period.

10. The method of claim 9, wherein said storage period is at least 21 days and said oxygen reduced stored blood further comprises a higher ratio of GSH to glutathione disulfide (GSSG) (GSH/GSSG ratio) when said oxygen saturation is between 5% and 10%,
an increased reservoir of nicotinamide adenine dinucleotide (NAD),
an increased reservoir of nicotinamide adenine dinucleotide+hydrogen (NADH), and
a reduced level of dioxidation of Cys152 in Glyceraldehyde-3-Phosphate Dehydrogenase (GAPDH) when said initial oxygen saturation is about 5%,
wherein said higher ratio, said increased reservoir or said reduced level in said oxygen reduced stored blood is relative to said non-oxygen reduced stored blood, wherein said oxygen reduced stored blood and said non-oxygen reduced stored blood are stored for an identical storage period.

11. The method of claim 10, wherein said storage period is at least 28 days and said oxygen reduced stored blood further comprises
an increase level of NADPH,
an increased ratio of NADPH/NADP$^+$, and
an increased level of cysteine,
wherein said increase level in said oxygen reduced stored blood is relative to said non-oxygen reduced stored blood, wherein said oxygen reduced stored blood and said non-oxygen reduced stored blood are stored for an identical storage period.

12. The method of claim 1, wherein said initial oxygen saturation is 10% or less.

13. The method of claim 1, wherein said oxygen reduced stored blood comprises fewer pre-eryptotic biomarkers compared to non-oxygen reduced stored blood stored for an identical storage period.

14. The method of claim 1, wherein said sickle cell patient has a peak center-flow velocity of greater than 200 cm/sec as determined by transcranial Doppler ultrasound (TCD).

15. The method of claim 1, wherein said sickle cell patient experiencing a vaso-occlusive crisis.

16. The method of claim 1, wherein said sickle cell patient in need of a blood transfusion is a patient in need of multiple transfusions and sickle hemoglobin levels rise above 30%.

17. The method of claim 1, wherein said transfusion is a pen-operative transfusion.

18. The method of claim 1, wherein said initial oxygen saturation is 5% or less.

19. The method of claim 1, wherein said initial oxygen saturation is 3% or less.

* * * * *